United States Patent
Ding et al.

(10) Patent No.: US 9,206,198 B2
(45) Date of Patent: Dec. 8, 2015

(54) INHIBITORS OF THE RENAL OUTER MEDULLARY POTASSIUM CHANNEL

(71) Applicant: Merck Sharp & Dohme Corp., Rahway, NJ (US)

(72) Inventors: Fa-Xiang Ding, Staten Island, NY (US); Shuzhi Dong, Plainsboro, NJ (US); Jessica Frie, Harleysville, PA (US); Xin Gu, Scotch Plains, NJ (US); Jinlong Jiang, Scotch Plains, NJ (US); Alexander Pasternak, Princeton, NJ (US); Haifeng Tang, Metuchen, NJ (US); Zhicai Wu, Montvale, NJ (US); Yang Yu, Edison, NJ (US); Takao Suzuki, Pudong Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/569,858

(22) Filed: Dec. 15, 2014

(65) Prior Publication Data
US 2015/0099729 A1    Apr. 9, 2015

Related U.S. Application Data

(62) Division of application No. 13/951,096, filed on Jul. 25, 2013, now Pat. No. 8,952,166.

(60) Provisional application No. 61/759,040, filed on Jan. 31, 2013, provisional application No. 61/691,390, filed on Aug. 21, 2012.

(51) Int. Cl.
| | |
|---|---|
| *C07D 471/20* | (2006.01) |
| *A61K 31/435* | (2006.01) |
| *A61K 31/46* | (2006.01) |
| *A61K 31/5386* | (2006.01) |
| *C07D 471/10* | (2006.01) |
| *A61K 45/06* | (2006.01) |
| *C07D 498/20* | (2006.01) |
| *A61K 31/4995* | (2006.01) |
| *C07D 451/00* | (2006.01) |
| *C07D 519/00* | (2006.01) |

(52) U.S. Cl.
CPC ............ *C07D 498/20* (2013.01); *A61K 31/435* (2013.01); *A61K 31/46* (2013.01); *A61K 31/4995* (2013.01); *A61K 31/5386* (2013.01); *A61K 45/06* (2013.01); *C07D 451/00* (2013.01); *C07D 471/10* (2013.01); *C07D 471/20* (2013.01); *C07D 519/00* (2013.01)

(58) Field of Classification Search
CPC .. C07D 519/00; C07D 451/00; C07D 471/10; C07D 498/20; A61K 45/06; A61K 31/435; A61K 31/46; A61K 31/4995; A61K 31/5386
USPC ......................................... 514/278; 546/200
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |
| 5,736,546 A | 4/1998 | Kawashima et al. |

(Continued)

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

Felix; Assay and Drug Development Technologies, 2012, 10, 417-431.*
Doggrell; Cardiovascular Research, 1998, 39, 89-105.*
ACCF/AHA Practice Guideline, 2009 Focused update incorporated into the ACC/AHA 2005 guidelines . . . , Circulation, 2009, e391-e436, 119.
Baltzly, R., The preparation of N-mono-substituted and unsymmetrically disubstituted piperazines, J. Am. Chemoc., 1944, 263-266, 66.
Bhave, G., Small-molecule modulators of inward rectifier K+ channels: recent advances and future possibilities, Future Med Chem, 2010, 757-774, 2(5).
Bhave,G., Development of a selective small-molecule inhibitor Kir1.1, the renal outer medullary potassium channel, Mol. Pharmacol., 2011, 42-50, 79.

(Continued)

*Primary Examiner* — Janet L Andres
*Assistant Examiner* — Daniel Carcanague
(74) *Attorney, Agent, or Firm* — Nicole M. Beeler; Catherine D. Fitch

(57) ABSTRACT

The present invention provides compounds of Formula I

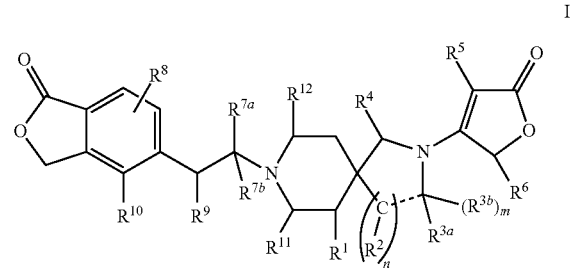

and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and conditions associated with excessive salt and water retention.

12 Claims, No Drawings

(56) References Cited

U.S. PATENT DOCUMENTS

| | | |
|---|---|---|
| 6,258,813 B1 | 7/2001 | Arlt et al. |
| 6,787,543 B2 | 9/2004 | Take et al. |
| 2004/0204404 A1 | 10/2004 | Zelle et al. |
| 2005/0215526 A1 | 9/2005 | Hulme et al. |
| 2005/0267121 A1 | 12/2005 | Li et al. |
| 2006/0183739 A1 | 8/2006 | Tsaklakidis et al. |
| 2006/0183742 A1 | 8/2006 | Mederski et al. |
| 2006/0211692 A1 | 9/2006 | Mederski et al. |
| 2007/0004750 A1 | 1/2007 | Lorsbach et al. |
| 2007/0093472 A1 | 4/2007 | Mederski et al. |
| 2008/0003214 A1 | 1/2008 | Cezanne et al. |
| 2010/0286123 A1 | 11/2010 | Pasternak et al. |

FOREIGN PATENT DOCUMENTS

| | | |
|---|---|---|
| EP | 1094063 A1 | 4/2001 |
| EP | 1939175 A1 | 7/2009 |
| FR | 2673182 | 8/1992 |
| FR | 2673182 A1 | 8/1992 |
| GB | 949088 A | 2/1964 |
| GB | 1575310 A | 9/1980 |
| GB | 2116967 | 7/1986 |
| JP | 10203986 | 8/1998 |
| WO | 9744329 | 11/1997 |
| WO | 0051611 A1 | 9/2000 |
| WO | 0204314 A1 | 6/2002 |
| WO | 0250061 A1 | 6/2002 |
| WO | 2004020422 A1 | 3/2004 |
| WO | 0232874 | 4/2004 |
| WO | 2004037817 A1 | 5/2004 |
| WO | 2004046110 | 6/2004 |
| WO | 2005037843 | 4/2005 |
| WO | 2005044797 | 5/2005 |
| WO | 2006034341 A2 | 3/2006 |
| WO | 2006034769 A1 | 4/2006 |
| WO | 2006098342 A1 | 9/2006 |
| WO | 2006129199 A1 | 12/2006 |
| WO | 2007075629 A2 | 7/2007 |
| WO | 2008147864 | 12/2008 |
| WO | 2008147864 A2 | 12/2008 |
| WO | 2009149508 | 11/2009 |
| WO | 2010129379 A1 | 11/2010 |
| WO | 2012058116 A1 | 5/2012 |
| WO | 2012058134 A1 | 5/2012 |
| WO | 2013028474 A1 | 2/2013 |
| WO | 2013039802 A1 | 3/2013 |
| WO | 2013062892 A1 | 5/2013 |
| WO | 2013062900 A1 | 5/2013 |
| WO | 2013066714 A1 | 5/2013 |
| WO | 2013066717 A1 | 5/2013 |
| WO | 2013066718 A2 | 5/2013 |
| WO | 2013090271 A1 | 6/2013 |

OTHER PUBLICATIONS

Brater et al., Diuretic Therapy, Drug Therapy, 1998, 387-395, 339.
Brewster et al., Antihypertensive 1,4-bis (2-indol-3-ylethyl)piperazines, Chimie Ther., 1973, 169-172 (English trans.), 2.
Cerkvenik-Flajs V, Determination of residues of azaperone in the kidneys by liquid chromatography with fluorescence, Anal. Chim. Acta., 2007, 374-382, 586.
Chemical Abstracts (2004), Abstract No. 697771-49-6, "1,3-Isobenzofurandione 5-[[4-[(5-chloro-2-methoxyphenyl) sulfonyl]-1-...".
Cheymol et al., Increase in the effects of epinephrine and acetylcholine . . . , Comptes Rendus des seances de la Societe de Biologie, 1951, 496-499 (English trans.), 145.
Dorwald, Side reactions in Organic Synthesis: A Guide to Successful Synthesis Design, 2005, Chapter 1.
Fallen, K., The Kir channel immunoglobuling domain is essential for Kir1.1 (ROMK) thermodynamic stability, trafficking and gating, Channels, 2009, 57-66, 3.
Felker et al, Diuretic strategies in patients with acute decompensated heart failure, New Eng. J. Med., 2011, 797-805, 364.
Frank, Managing hypertension using combination therapy, Am. Fam. Physician, 2008, 1279-1286, 77.
International Search Report for PCT/US2013/052079 mailed on Aug. 15, 2013, 8 pages.
Kulkarni, YD, Possible antifertility agents, part III. Synthesis of 4-(substituted aminomethyl)-5,6,7-trimethoxy phthalid . . . (abstract)), Biol. Mem., 1987, 141-144, 13.
Lanyi et al., Piperazine-Derivatives II, Res. Lab. of Chinoin-Fabrik Chemisch-Pharma. Prod., 1968, 1431-1435 (English trans.), 18.
Lewis, L. M., High-throughput screening reveals a small-molecule inhibitor of the Renal Outer Medullary Potassium Channel and Kir7.1, Mol. Pharncol., 2009, 1094-1103, 76.
Lutz, R. E., Antimalarials. Some Piperazine Derivatives, J. Org. Chem., 1947, 771-775, 12, BO.
Miyake et al., Synthesis of 1-substituted isochroman . . . , Takeda Res. Lab., 1982, 24-40 (English trans.), 41.
Sica, D. A., Diuretic use in renal disease, Nature, 2012, 100-109, 8.
Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

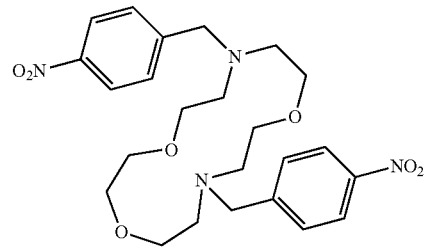

VU590

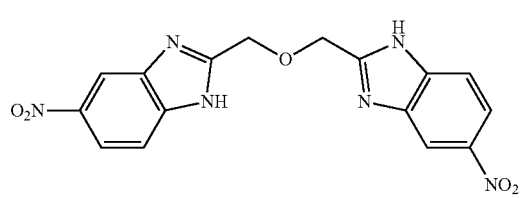

VU591

Patent application publication number WO2010/129379, published Nov. 11, 2010 having common representative Merck Sharp & Dohme Corp., (also published as US2010/0286123 on same date), describes ROMK inhibitors having the generic formula:

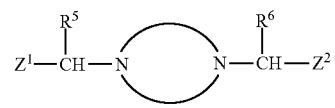

and, e.g., an embodiment

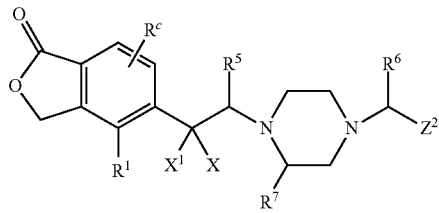

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OC_{1-3}$alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

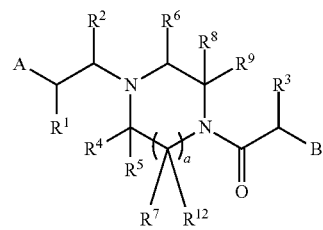

wherein A and B are mono and/or bicyclic aromatic groups; $R^2$ is —H, —$C_{1-6}$ alkyl, —$C_{3-6}$ cycloalkyl, $CF_3$, —$CH_2OH$, or —CO₂R, or R² can be joined to R¹ or R¹⁰ᵃ to form a ring; R³ is —H, —C₁₋₆ alkyl, —C₃₋₆ cycloalkyl, —OH, —F, —OC₁₋₃ alkyl, or —CH₂OH, or R³ can be joined to R¹⁰ᵇ to form a ring.

Patent application publication number WO2012/058116, published May 3, 2012, having common representative Merck Sharp & Dohme Corp., describes ROMK inhibitors having the generic formula:

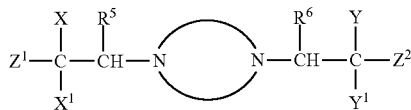

and, e.g., an embodiment

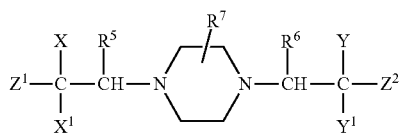

wherein R⁵ and R⁶ are independently —H, —C₁₋₆ alkyl or —C(O)OC₁₋₃alkyl; and X, X¹, Y and Y¹ are independently H or —C₁₋₆alkyl; or Y¹ can be joined together with Z² to form a fused ring system.

However, continuing discovery of selective small molecule inhibitors of ROMK is still needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

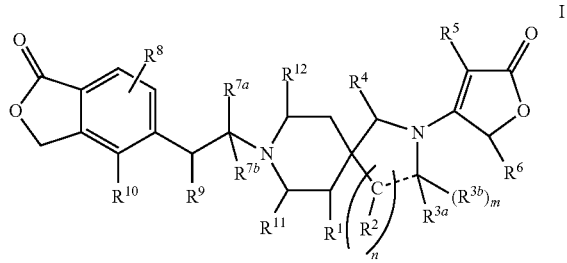

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

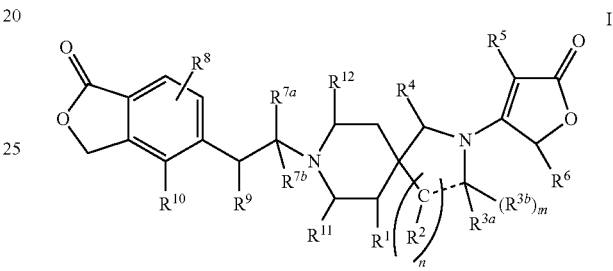

or a pharmaceutically acceptable salt thereof wherein:

R¹— is H, halo particularly —F, —OH, or —OC₁₋₃alkyl particularly —OCH₃;

m is an integer selected from zero (R³ᵇ is absent) and 1 (R³ᵇ is present);

n is an integer selected from 1 or 2;

R² is independently selected at each occurrence from —H, =O (oxo), —OH, —C₁₋₃alkyl or —OC₁₋₃alkyl, provided that when n is 2, then at least one R² is —H;

R³ᵃ is —H, =O, —C₃₋₄cycloalkyl or —C₁₋₃alkyl optionally substituted with —OCH₃ or 1 to 3 of —F, provided that only one of R² or R³ᵃ can be =O, R³ᵇ is H or —C₁₋₃alkyl, or R³ᵇ is absent when R³ᵃ is =O or when the dashed bond is a double bond or an aromatic bond;

or R³ᵃ and R³ᵇ are joined together with the carbon to which they are both attached to form cyclopropyl or cyclobutyl;

or when n is 1, R² and R³ᵃ can be joined together with the carbons to which they are each attached to form (1) a phenyl ring which is fused to the pyrrolidine ring, and m is zero, or (2) a cyclopropyl ring fused to the pyrrolidine ring, and m is 1;

R⁴ is —H or =O;

R⁵ is (a) —H, (b) halo, particularly —Cl or —F, (c) —C₁₋₃ alkyl optionally substituted with —O—C₁₋₃alkyl, (d) —C₃₋₆cycloalkyl or (e) heterocycle optionally substituted with —C₁₋₃alkyl or halo, particularly F or —Cl;

R⁶ is —H or —C₁₋₃alkyl;

R⁷ᵃ is —H or —C₁₋₃alkyl optionally substituted with —OH, —OCH₃ or 1 to 3 of —F;

R⁷ᵇ is —H or —C₁₋₃alkyl;

or R⁷ᵃ and R⁷ᵇ are joined together with the carbon to which they are both attached to form —C₃₋₄cycloalkyl;

R⁸ is —H, halo particularly —F, or —C₁₋₃alkyl;

$R^9$ is —H, —F, —OH, —OC$_{1-3}$alkyl, —CH$_2$OH, —NH—R$^{13}$ or

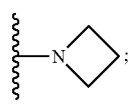

$R^{10}$ is —H, halo, —CN, —C$_{3-4}$cycloalkyl, or —C$_{1-3}$alkyl optionally substituted with 1 to 3 of —F;

or $R^9$ is —O— and is joined together with $R^{10}$ to represent —CH$_2$—CH$_2$—O—;

$R^{11}$ is —H, —CH$_2$OH, —CH$_2$OCH$_3$, or —C$_{1-3}$alkyl optionally substituted with 1 to 3 of —F;

$R^{12}$ is —H, —CH$_2$OH, —CH$_2$OCH$_3$, or —C$_{1-3}$alkyl optionally substituted with 1 to 3 of —F;

or $R^{11}$ and $R^{12}$ are joined together to represent —CH$_2$—CH$_2$, —CH$_2$—N(CH$_3$)—CH$_2$— or —CH$_2$OCH$_2$—;

$R^{13}$ is —H, —(CH$_2$)$_{0-2}$—C$_{3-6}$ cycloalkyl, —(CH$_2$)$_{1-2}$—OC$_{3-6}$cycloalkyl, —(CH$_2$)$_{1-2}$—OC$_{1-3}$alkyl, —(CH$_2$)$_{1-2}$—CN, —C(O)OC$_{1-3}$alkyl, —SO$_2$CH$_3$ or —C$_{1-3}$alkyl optionally substituted with one to three of —F; and the dashed bond ("- - -") represents a single, double or aromatic bond, provided that (A) when n is 2, then the dashed bond is a single bond and m is 1; and (B) when n is 1 and
  (i) m is 1 (which includes but is not limited to compounds wherein $R^2$ and $R^{3a}$ are joined to represent cyclopropyl fused to the pyrrolidine ring), or
  (ii) $R^{3a}$ is =O and m is zero,
  then the dashed bond is a single bond; and (C) when n is 1, m is zero, $R^2$ is not =O and $R^{3a}$ is not =O, then the dashed bond is
  (i) a double bond, or
  (ii) an aromatic bond when $R^2$ and $R^{3a}$ are joined together to form the phenyl ring fused to the pyrrolidine ring.

In an embodiment of this invention are compounds of Formula I having structural Formula II and the pharmaceutically acceptable salts thereof:

II

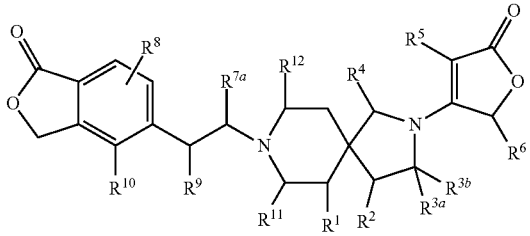

wherein n is 1 and m is 1, and each of the variables $R^1$, $R^2$, $R^{3a}$, $R^{3b}$, $R^4$, $R^5$, $R^6$, $R^{7a}$, $R^8$, $R^9$, $R^{10}$, $R^{11}$, $R^{12}$ and $R^{13}$ and all other variables therein are as defined in Formula I.

In an embodiment of this invention are compounds of Formula I having structural Formula III and the pharmaceutically acceptable salts thereof:

III

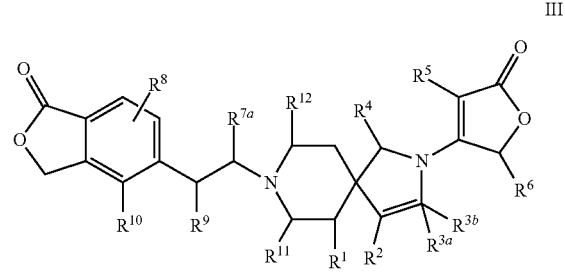

wherein n is 1 and m is zero, and each of the variables $R^1$, $R^2$, $R^{3a}$, $R^4$, $R^5$, $R^6$, $R^{7a}$, $R^8$, $R^9$, $R^{10}$, $R^{11}$, $R^{12}$ and $R^{13}$ and all other variables therein are as defined in Formula I, and wherein the double bond between $R^2$ and $R^{3a}$ represents a non-aromatic double bond, or an aromatic bond when $R^2$ and $R^{3a}$ are joined together with the carbons to which they are each attached to form a phenyl ring.

In an embodiment of this invention are compounds of Formula I having structural Formula IV and the pharmaceutically acceptable salts thereof:

IV

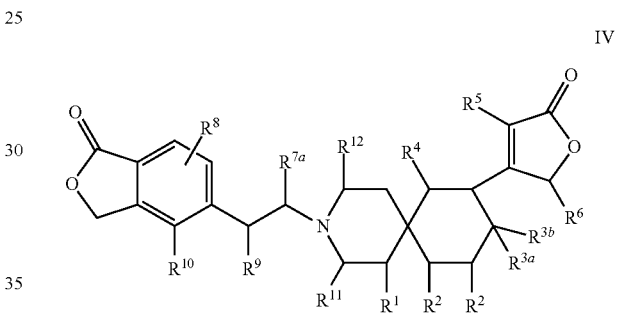

wherein n is 2 and m is 1, and each of the variables $R^1$, $R^2$, $R^{3a}$, $R^{3b}$, $R^4$, $R^5$, $R^6$, $R^{7a}$, $R^8$, $R^9$, $R^{10}$, $R^{11}$, $R^{12}$ and $R^{13}$ and all other variables therein are as defined in Formula I.

In another embodiment of this invention are compounds of Formula I having structural Formula V:

V

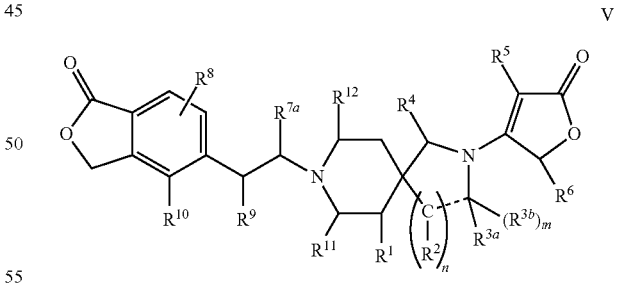

or a pharmaceutically acceptable salt thereof wherein:

$R^1$ is —H, —F, —OH or —OCH$_3$;

m is an integer selected from zero ($R^{3b}$ is absent) and 1 ($R^{3b}$ is present);

n is an integer selected from 1 or 2;

$R^2$ is independently selected at each occurrence from —H, =O (oxo), —OH, —C$_{1-3}$alkyl or —OC$_{1-3}$alkyl, provided that when n is 2, then at least one $R^2$ is —H;

$R^{3a}$ is —H, =O, —C$_{3-4}$cycloalkyl or —C$_{1-3}$alkyl optionally substituted with —OCH$_3$ or 1 to 3 of —F, provided that only one of $R^2$ or $R^{3a}$ can be =O, $R^{3b}$ is —H or —$C_{1-3}$alkyl, or $R^{3b}$ is absent when $R^{3a}$ is =O or when the dashed bond is a double bond or an aromatic bond;

or $R^{3a}$ and $R^{3b}$ are joined together with the carbon to which they are both attached to form cyclopropyl or cyclobutyl;

or when n is 1, $R^2$ and $R^{3a}$ can be joined together with the carbons to which they are each attached to form (1) a phenyl ring which is fused to the pyrrolidine ring, and m is zero, or (2) a cyclopropyl ring fused to the pyrrolidine ring, and m is 1;

$R^4$ is —H or =O;

$R^5$ is —H, —Cl, —F, —$C_{1-3}$alkyl, —$C_{3-6}$cycloalkyl or heterocycle optionally substituted with —F, —Cl or —$C_{1-3}$alkyl;

$R^6$ is —H or —$C_{1-3}$alkyl;

$R^{7a}$ is —H or —$C_{1-3}$alkyl optionally substituted with —OH, —OCH$_3$ or 1 to 3 of —F;

$R^8$ is —H, —F or —$C_{1-3}$alkyl;

$R^9$ is —H, —F, —OH, —O$C_{1-3}$alkyl, —CH$_2$OH, —NH—$R^{13}$ or

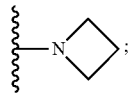

$R^{10}$ is —H, halo, —CN, —$C_{3-4}$cycloalkyl, or —$C_{1-3}$alkyl optionally substituted with 1 to 3 of —F;

or $R^9$ is —O— and is joined together with $R^{10}$ to represent —CH$_2$—CH$_2$—O—;

$R^{11}$ is —H, —CH$_2$OH, —CH$_2$OCH$_3$, or —$C_{1-3}$alkyl optionally substituted with 1 to 3 of —F;

$R^{12}$ is —H, —CH$_2$OH, —CH$_2$OCH$_3$, or —$C_{1-3}$alkyl optionally substituted with 1 to 3 of —F;

or $R^{11}$ and $R^{12}$ are joined together to represent —CH$_2$—CH$_2$—, —CH$_2$—N(CH$_3$)—CH$_2$— or —CH$_2$OCH$_2$—;

$R^{13}$ is —H, —(CH$_2$)$_{0-2}$—$C_{3-6}$ cycloalkyl, —(CH$_2$)$_{1-2}$—O$C_{3-6}$cycloalkyl, —(CH$_2$)$_{1-2}$—O$C_{1-3}$ alkyl, —(CH$_2$)$_{1-2}$—CN, —C(O)O$C_{1-3}$alkyl, —SO$_2$CH$_3$ or —$C_{1-3}$alkyl optionally substituted with one to three of —F; and the dashed bond ("- - -") represents a single, double or aromatic bond, provided that when n is 2, then the dashed bond is a single bond and m is 1, and when n is 1 and m is 1, then the dashed bond is a single bond, and when n is 1 and m is zero, then the dashed bond is
(a) a double bond, or
(b) an aromatic bond when $R^2$ and $R^{3a}$ are joined together to form the phenyl ring.

In another embodiment of this invention are compounds of Formula I wherein: n is 2 and the dashed bond is a single bond and m is 1, or n is 1 and the dashed bond is a single bond and m is 2, or the dashed bond is a double bond and m is 1; $R^1$ is —H, —F, —OH or —$C_{1-3}$alkyl; $R^4$ is =O; $R^5$ is —H or —$C_{1-3}$alkyl; $R^8$ is —H or —$C_{1-3}$alkyl; $R^9$ is —OH, —O$C_{1-3}$alkyl or —NHR$^{13}$; $R^{10}$ is as defined; $R^{11}$ and $R^{12}$ are —H; and all other variables are as defined in Formula I.

In an embodiment of this invention are compounds of Formula I wherein the dashed bond represents a double bond or an aromatic bond. Formulas II and IV depict examples of embodiments wherein the dashed bond is a single bond.

In an embodiment of this invention are compounds of Formula I, II, III, IV or V wherein $R^1$— is H or F, and more particularly it is —H.

In an embodiment of this invention are compounds of Formula I, II, III, IV or V wherein $R^2$ is —H at each occurrence.

In an embodiment of this invention are compounds of Formula I, II, III, IV or V wherein $R^{1a}$ is —H, —$C_{1-3}$alkyl, cyclopropyl, and more particularly it is —H or —CH$_3$.

In an embodiment of this invention are compounds of Formula I, II, IV or V wherein $R^{3b}$ is —H or —$C_{1-3}$alkyl, and more particularly it is —H, or $R^{3b}$ is absent when the dashed bond is a double bond or an aromatic bond.

In an embodiment of this invention are compounds of Formula I, II, III, IV or V wherein $R^4$ is =O.

In an embodiment of this invention are compounds of Formula I, II, III, IV or V wherein $R^5$ is (a) —H, (b) halo, and particularly —Cl or —F, (c) —$C_{1-3}$alkyl (d) —$C_{3-6}$cycloalkyl, and more particularly it is —H or —CH$_3$.

In an embodiment of this invention are compounds of Formula I, II, III, IV or V wherein $R^6$ is —H or —CH$_3$, and more particularly it is —H.

In an embodiment of this invention are compounds of Formula I, II, III or IV wherein $R^{7a}$ is —H or —$C_{1-3}$alkyl optionally substituted with —OH, —OCH$_3$ or 1 to 3 of —F, and more particularly it is —H or —CH$_3$.

In an embodiment of this invention are compounds of Formula I, II, III or IV and wherein $R^{7b}$ is —H or —$C_{1-3}$alkyl, and more particularly it is —H.

In an embodiment of this invention are compounds of Formula I, II, III, IV or V wherein $R^8$ is —H.

In an embodiment of this invention are compounds of Formula I, II, III, IV or V wherein $R^9$ —H, —OH, —OCH$_3$ or —NH$_2$, and particularly it is —OH.

In an embodiment of this invention are compounds of Formula I, II, III, IV or V wherein $R^{10}$ is —H, —$C_{1-3}$ alkyl, —$C_{3-4}$cycloalkyl, —F, and particularly it is —CH$_3$.

In an embodiment of this invention are compounds of Formula I, II, III, IV or V thereof wherein $R^{11}$ is —H or —$C_{1-3}$alkyl, and more particularly it is —H.

In an embodiment of this invention are compounds of Formula I, II, III, IV or V wherein $R^{12}$ is —H or —$C_{1-3}$ alkyl, and more particularly it is —H; or $R^{11}$ and $R^{12}$ are joined together to represent —CH$_2$—CH$_2$, —CH$_2$—N(CH$_3$)—CH$_2$— or —CH$_2$OCH$_2$—.

In an embodiment of this invention are compounds of Formula I, II, III, IV or V wherein $R^{13}$ is —H or —$C_{1-3}$alkyl, and more particularly it is —H.

In Embodiment A of this invention are compounds of Formula I, II, III, IV or V wherein: $R^{3a}$ is —H or —CH$_3$; $R^4$ is =O; $R^5$ is —H or —CH$_3$; $R^{7a}$ is —H or —CH$_3$; $R^9$ is —H, —OH, —OCH$_3$ or —NH$_2$, and particularly it is —OH; and $R^{10}$ is —H or —CH$_3$, and particularly it is —CH$_3$. In a class thereof are compounds of Embodiment A, referred to as Embodiment B, wherein $R^1$ is —H; $R^2$ is —H at each occurrence; $R^{3b}$ is —H (for compounds of Formula I, II or IV); $R^6$ is —H; $R^8$ is —H; $R^{11}$ is —H; and $R^{12}$ is —H.

All structural Formulas and embodiments thereof described herein include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me). "Cycloalkyl" is a cyclized alkyl ring having the indicated number of carbon atoms. Examples of cycloalkyl include cyclopropyl, cyclobutyl, cyclopentyl and cyclohexyl.

"Halo" means —F, —Cl, —Br, or —I.

"Heterocycle" is intended to include pyridyl (all isomers), pyrazinyl, pyridazinyl or pyrimidinyl.

As is well-known in the art, the term "double bond" refers to a covalent bond where two pairs of electrons are shared between two atoms. The concept of aromaticity is likewise well-known in the art, as exemplified by benzene and phenyl which are commonly drawn as having 3 alternating double bonds, but may also be considered as having carbon-carbon bonds which are each a hybrid of a single bond and a double bond. As used herein, an "aromatic bond" refers to the aromatic nature of the double bond between —C($R^2$)— and —C($R^{3a}$)— when $R^2$ and $R^{3a}$ are joined together to form a phenyl ring fused to the pyrrolidinyl ring as defined in Formulas I, III and V.

Unless expressly depicted or described otherwise, variables depicted in a structural formula with a "floating" bond, such as $R^8$, are permitted on any available carbon atom in the ring to which the variable is attached.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cistrans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

Reference to the compounds of Formula I herein encompasses the compounds of Formulas I, II, III, IV and V and all embodiments thereof. Reference to the compounds of this invention as those of a specific formula or embodiment, e.g., Formula I, II, III, IV or V or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diueresis, natriuresis or both. The inhibition of ROMK by the compounds of Formula I can be examined, for example, in the Thallium Flux Assay and/or Electrophysiology Assay described below. Moreover, this invention also relates to the use of the compounds of Formula I or salts thereof to validate in vitro assays, for example but not limited to the Thallium Flux and Electrophysiology Assays described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) Thallium Flux Assay, 2) Electrophysiology Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterfied forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Clalis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" substituents in the Schemes correspond to the substituents defined in Formula I at the same positions on the structures.

Compound IA, which is substituted at the benzylic position with an OH group, can be prepared following the sequence detailed in Scheme 1. Coupling of epoxide 1 to spirocyclic amines 2 at elevated temperatures leads to the formation of alcohols IA (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol and 2-propanol. Spirocyclic amines may be free bases, or they may be salts, in which case a base such as triethylamine or N; N-diisopropylethylamine may be added. Note that when enantiopure chiral epoxides are employed (such as (R)-1 in Scheme 1) epoxide opening occurs with retention of stereochemistry in the benzylic position and individual isomer (R)-IA may be obtained (and if the (S)-epoxide is employed the alcohol produced will have the opposite stereochemistry to that shown). Alternatively, chiral HPLC separation of enantiomers or diastereomers of IA may be performed to provide single enantiomers or diastereomers.

SCHEME 1

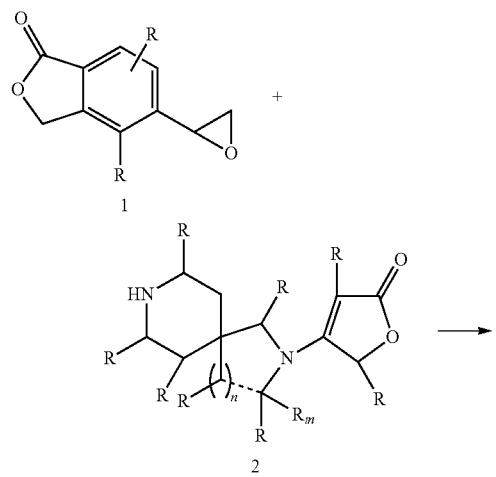

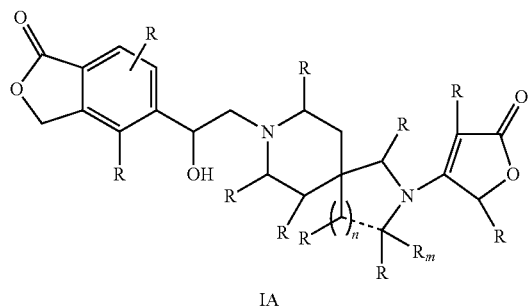

IA

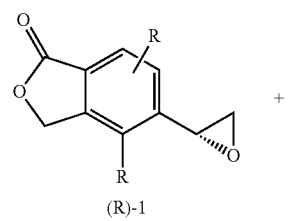

(R)-1

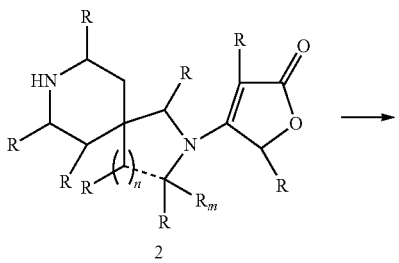

2

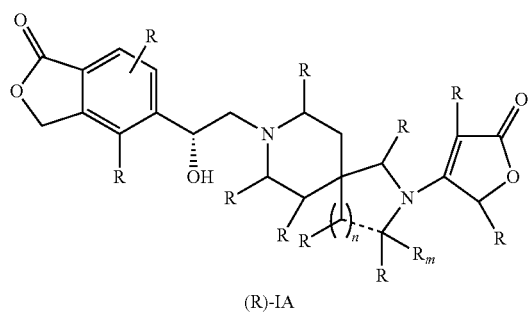

(R)-IA

Compounds of formula IB can be prepared by the sequence detailed in Scheme 2. Aldhehydes or ketones 3 may be used in reductive alkylation reactions of spirocyclic amines 2 to afford ROMK inhibitors of the formula IB by using various reductive amination conditions (for example using sodium cyanoborohydride, sodium triacetoxy borohydride, or titanium tetra-isopropoxide, followed by sodium borohydride or sodium cyanoborohydride).

SCHEME 2

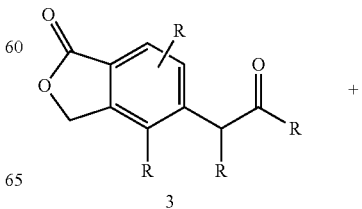

3

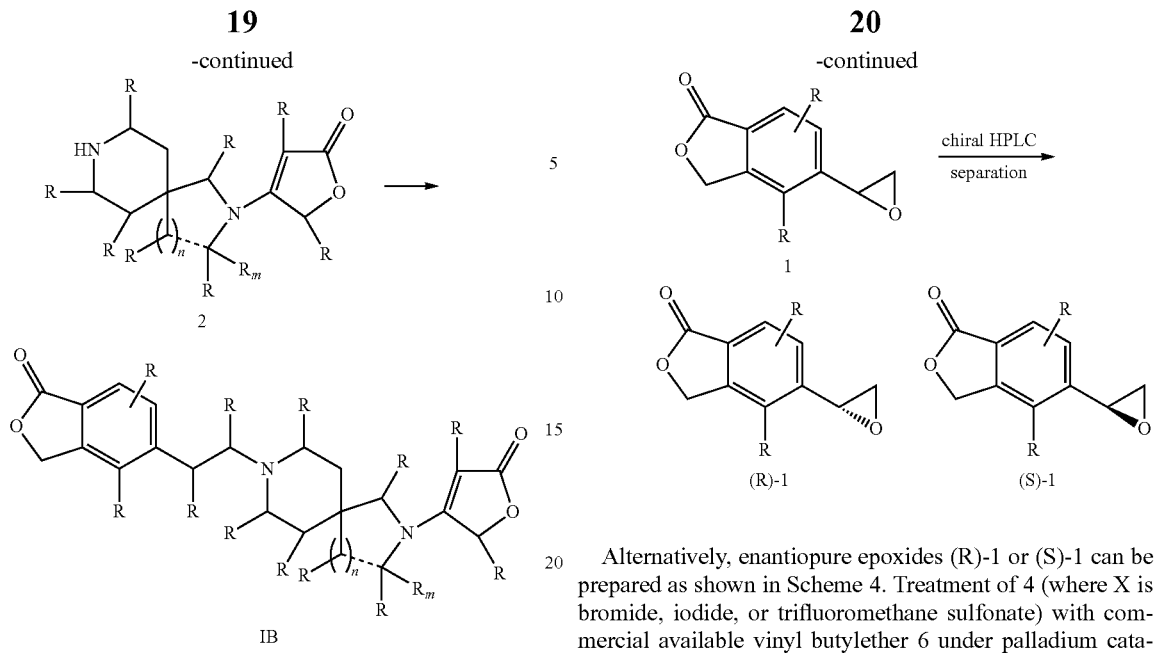

The epoxides 1 (and single enantiomers (R)-1 and (S)-1) can be prepared following the method detailed in Scheme 3. Treatment of 4 (where X is chloride, bromide, iodide, or trifluoromethane sulfonate) with commercially available potassium vinyl trifluoroborate (Molander, G.; Luciana, A. Journal of Organic Chemistry, 2005, 70(10), 3950-3956) under palladium catalyzed coupling conditions with an appropriate phosphine ligand gives rise to styrene 5 (Molander, G.; Brown, A. Journal of Organic Chemistry, 2006, 71(26), 9681-9686). Alternatively, other methods may be employed, for example, using vinylstannane reagents and palladium catalysis. The resulting styrenes 5 can be converted to the corresponding epoxides 1 under various epoxidation conditions, for example, with mCPBA (Fringuelli, F. et al. Organic Preparations and Procedures International, 1989, 21(6), 757-761). The racemic epoxide 1 can be resolved under chiral HPLC chromatography conditions to afford its enantiomers, which can be used in place of 1 according to Scheme 1.

Alternatively, enantiopure epoxides (R)-1 or (S)-1 can be prepared as shown in Scheme 4. Treatment of 4 (where X is bromide, iodide, or trifluoromethane sulfonate) with commercial available vinyl butylether 6 under palladium catalyzed conditions with a suitable ligand (for example Pd(OAc)$_2$, DPPP) can provide the enol ethers 7. Enol ethers may be prepared using other methods known to the chemist. Treatment of the resulting enol ethers 7 with NBS or other similar reagents affords the corresponding bromomethyl ketones 8. These can be subjected to a variety of asymmetric ketone reduction conditions, for example with an enzyme that can affect such a transformation with high enantioselectivity. Subsequent treatment with a base such as triethylamine leads to cyclization, affording the enantioenriched epoxides (R)-1 or (S)-1 (depending upon the asymmetric reducing agent).

SCHEME 4

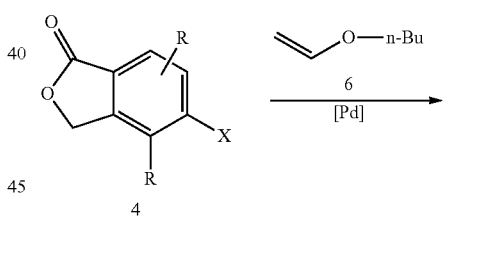

SCHEME 3

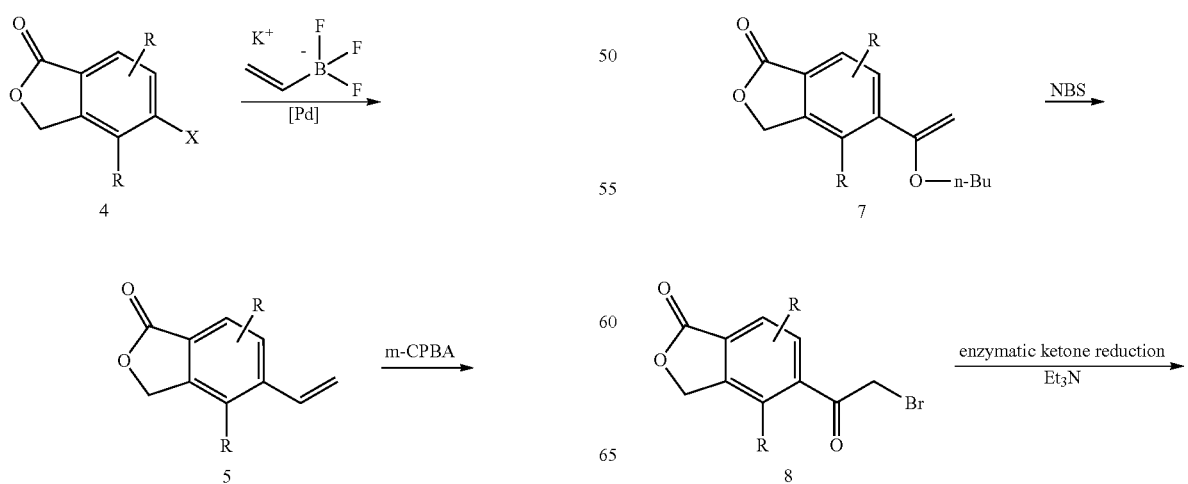

the examples below. Intermediates 13 are converted to spirocyclic aminofuranones 2 by removal of the protective group, for example, tert-butoxycarbonyl can be removed with TFA or HCl.

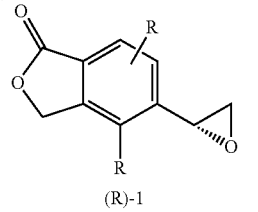
(R)-1

Aldehydes 3A may be prepared in numerous ways, with two approaches described in Scheme 5. Treatment of 4 (where X is bromide, iodide, or trifluoromethane sulfonate) with bromo(1,3-dioxolan-2-ylmethyl)zinc in the presence of an appropriate palladium catalyst and ligand, such as palladium(II) acetate and tri-t-butylphosphine-$BF_4$ complex, provides the corresponding aryl 1,3-dioxolan-2-ylmethyl derivative 9. Then the aldehydes 3A may be obtained by treatment with HCl in the presence of water and an organic solvent. Alternatively, reaction of 4 (where X is bromide, iodide, or trifluoromethane sulfonate) with allyltributylstannane in the presence of palladium catalyst affords the allyl product 10. Oxidation, for example with ozone, followed by dimethyl sulfide, provides aldehydes 3A.

SCHEME 6

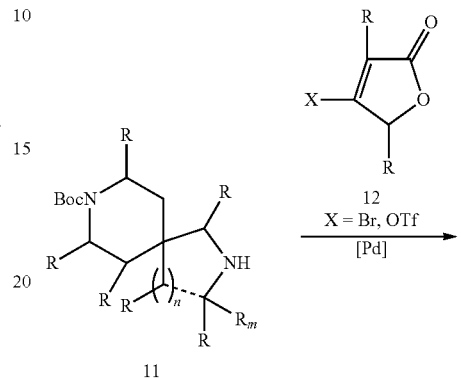

SCHEME 5

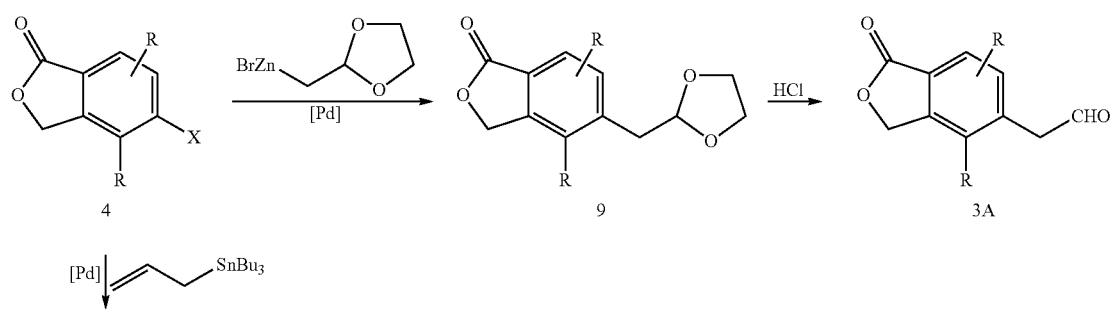

X = Br, OTf

Spirocyclic aminofuranones 2 can be prepared as described in Scheme 6. Spirocyclic diamines or amino lactams (where $R^{11}$ and $R^{12}$ together represent a carbonyl group) 11, protected as appropriate (Greene, T.; Wuts, P. G. M. *protective Groups in Organic Synthesis*, John Wiley and Sons, Inc., New York, N.Y. 1991), can be coupled to furanone triflates or bromides 12 using a palladium catalyst and ligand, for example palladium acetate and 4,5-Bis(diphenylphosphino)-9,9-dimethylxanthene. Some spirocyclic diamines or amino lactams 11 described herein are commercially available; others can prepared as described in the experimental section below. 4-Bromofuran-2(5H)-one is commercially available; other furanones 12 can be prepared as described in

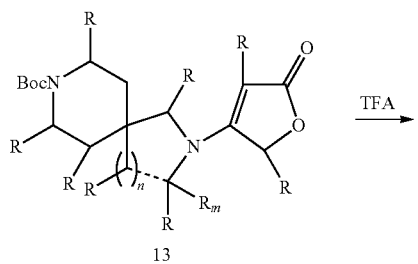

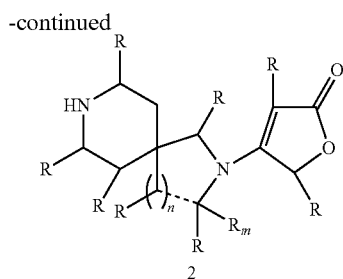

Spirocyclic amino lactams 11A, can be prepared in numerous ways, including those described in Scheme 7. Commercially available aminoesters 14 can be alkylated with bromoacetonitrile 15 using a base such as lithium diisopropylamide to afford nitrile intermediates 16. Reduction, for example using platinum oxide and hydrogen, or Raney Nickel, produces lactams 11A. Alternatively, aminoesters may be alkylated with allyl halides 17 using a base such as lithium diisopropylamide to furnish allyl intermediates 18. Oxidative cleavage, employing, for example, osmium tetroxide and sodium periodate provides ketones and aldehydes 19. Reductive amination with tandem lactam cyclization to 11A can be accomplished in several ways, including by treatment with ammonium acetate and sodium cyanoborohydride in a solvent such as methanol, as shown.

The subject compounds may be prepared by modification of the procedures disclosed in the Examples as appropriate. Starting materials are commercially available or made by known procedures or as illustrated. The following examples are provided for the purpose of further illustration only and are not intended to be limitations on the disclosed invention.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60E-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they

SCHEME 7

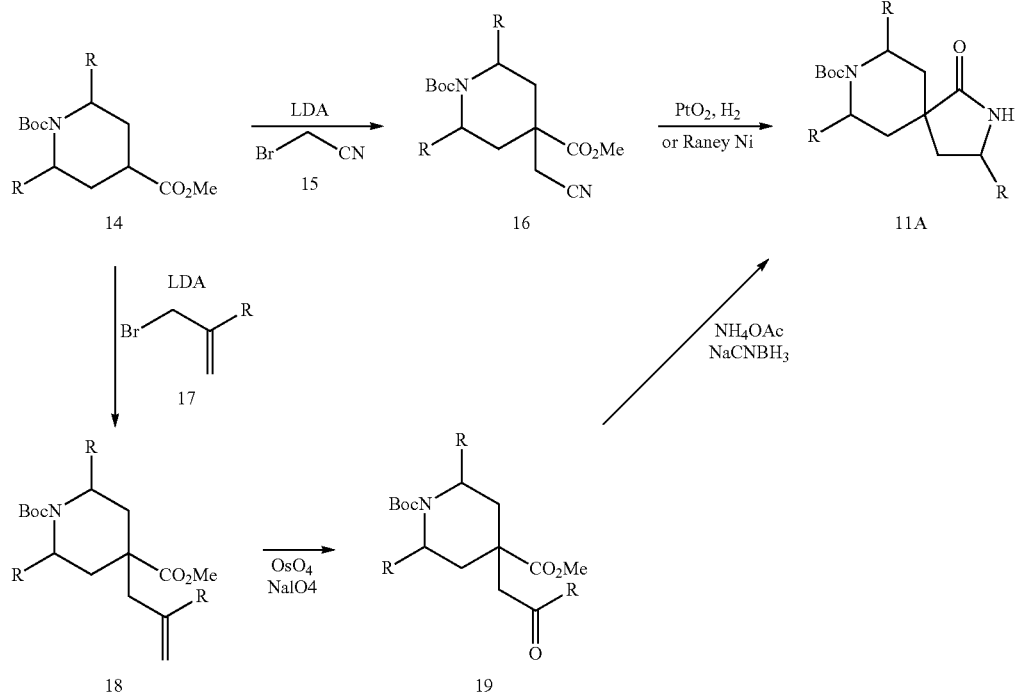

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

were performed on a Waters Chromatography Workstation configured with LC-MS System Consisting of: Waters ZQ single quad MS system with Electrospray Ionization, Waters 2525 Gradient Pump, Waters 2767 Injector Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz).

Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% EtHex) or isopropanol in heptane (% IPAHep) as isocratic solvent systems. Chiral preparative chromatography was sometimes conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was by supercritical fluid (SFC) conditions using one of Chiralpak AS, Chiralpak AD-H, Chiralcel OD-H, Chiralpak IC, or Chiralcel OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Concentration of solutions was generally carried out on a rotary evaporator under reduced pressure. Flash chromatography was carried out on silica gel (230-400 mesh). NMR spectra were obtained in $CDCl_3$ solution unless otherwise noted. Coupling constants (J) are in hertz (Hz).

Abbreviations and acronyms used herein include: —C(O)CH$_3$ (Ac); —OC(O)CH$_3$ (OAc); acetic acid (AcOH; HOAc); 1-chloroethylchloroformate (ACE-Cl); 2,2'-bis(diphenylphosphino)-1,1'-binaphthyl (BINAP); t-butyloxycarbonyl (Boc or BOC); di-t-butyl dicarbonate ((BOC)$_2$O, Boc$_2$O); benzyloxycarbonyl (Cbz); Cyclopentyl methyl ether (CPME); Carbonyldiimidazole (CDI); Diethylaminosulfur trifluoride (DAST); dibenzylideneacetone (dba); 1,8-Diazabicyclo[5.4.0]undec-7-ene (DBU); 1,2-dichloroethane (DCE); dichloromethane (DCM); dimethoxyethane (DME); Diisobutylaluminium hydride (DIBAL-H); N,N-diisopropylethylamine (DIEA, DIPEA, Hunig's base); di-isopropylamine (DIPA); 1,1'-bis(diphenylphosphino)ferrocene (dppf, DPPF); Dess-Martin Periodinane (DMP; 1,1,1-Triacetoxy-1,1-dihydro-1,2-benziodoxol-3(1H)-one); dimethylsulfide (DMS); dimethylsulfoxide (DMSO); N; N-dimethylformamide (DMF); 4-dimethylaminopyridine (DMAP); dimethylacetamide (DMA; DMAC); 1,3-Bis(diphenylphosphino)propane (DPPP); ethyl acetate (EtOAc); diethyl ether (ether or Et$_2$O); 1-ethyl-3-(3-dimethylaminopropyl)carbodiimide (EDC, EDAC or EDCI); 2-(7-Aza-1H-benzotriazole-1-yl)-1,1,3,3-tetramethyluronium hexafluorophosphate (HATU); hexane (Hex); hexamethylphosphoramide (HMPA); 1-Hydroxybenzotriazole hydrate (HOBt); isopropanol (IPA); isopropyl acetate (IPAc); Potassium bis(trimethylsilyl)amide (KHMDS); lithium aluminum hydride (LAH); lithium diisopropylamide (LDA); 3-chloroperoxybenzoic acid (mCPBA); methanol (MeOH); $CH_3SO_2$— (mesyl or Ms); methane sulfonyl chloride or mesyl chloride (MsCl); methanesulfonic acid (MsOH); methyl tert-butyl ether (MTBE); nicotinamide adenine dinucleotide phosphate (NADP); N-bromo succinimide (NBS); N-chlorosuccinimide (NCS); N-iodosuccinimide (NIS); N-methylmorpholine-N-oxide (NMO); N-methyl morpholine (NMP); sodium hoxamethyldisilazide (NaHMDS); sodium triacetoxyborohydride (NaBH(OAc)$_3$); Pyridinium chlorochromate (PCC); phenyl (Ph); petroleum ether (PE or petrol ether); tetrakis(triphenylphosphine)palladium (Pd(PPh$_3$)$_4$); tris(dibenzylidineacetone)dipalladium (Pd$_2$(dba)$_3$); Pd(dppf)Cl$_2$ or PdCl$_2$(dppf) is 1,1'-Bis(diphenylphosphino)ferrocene]dichloropalladium(II) which may be complexed with $CH_2Cl_2$; tetra-n-butylammonium fluoride (TBAF); tert-butyldimethylsilyl chloride (TBS-Cl); triethylamine (TEA); trifluoroacetic acid (TFA); —SO$_2$CF$_3$ (Tf); trifluoromethanesulfonic acid (triflic acid, TfOH); trifluoromethanesulfonic anhydride (triflic anhydride, (Tf)$_2$O); 2-tetrahydrofuran (THF); N,N,N',N'-Tetramethylethylenediamine (TMEDA); p-toluenesulfonic acid (TsOH); Dicyclohexylphosphino-2',4',6'-triisopropylbiphenyl (X-Phos); Diethylaminodifluorosulfinium tetrafluoroborate (XtalFluor-E®); 4,5-Bis(diphenylphosphino)-9,9-dimethylxanthene (Xantphos). Additional abbreviations and acronyms are: starting material (SM); round-bottom flask (RB or RBF); aqueous (aq); saturated aqueous (sat'd); saturated aqueous sodium chloride solution (brine); medium pressure liquid chromatography (MPLC); high pressure liquid chromatography (HPLC); preparative HPLC (prep-HPLC); flash chromatography (FC); liquid chromatography (LC); supercritical fluid chromatography (SFC); thin layer chromatography (TLC); preparative TLC (prep-TLC); mass spectrum (ms or MS); liquid chromatography-mass spectrometry (LC-MS, LCMS or LCMS); column volume (CV); room temperature (rt, r.t. or RT); hour(s) (h or hr); minute(s) (min); retention time (R$_t$); gram(s) (g); milligram(s) (mg); milliliter(s) (mL); microliter(s) (μL); millimole (mmol); volume:volume (V/V). CELITE® is a trademark name for diatomaceous earth, and SOLKA FLOC® is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereoconfigurations, or as a mixture of both. In many of the examples, compounds having a chiral center were separated into single stereoisomers (for example, referred to as Isomer A and Isomer B, or faster/slower eluting isomers), or each was derived synthetically from a single isomer intermediate. Except for a defined chiral center in the parent mixture, absolute stereochemistry (R or S) of each of the separated isomers was not determined, unless specifically noted otherwise.

Intermediate 1

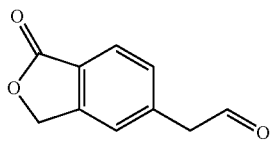 [SMILES: O=CCc1ccc2c(c1)COC2=O]

(1-Oxo-1,3-dihydro-2-benzofuran-5-yl)acetaldehyde

Step A: 5-(1,3-Dioxolan-2-ylmethyl)-2-benzofuran-1 (3H)-one: A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 470 mmol). DMF (1.88 L) was added to the flask, and the mixture was degassed three times by alternating vacuum and nitrogen purge. Commercially available bromo(1,3-dioxolan-2-ylmethyl)zinc solution (1.03 L, 516 mmol) was added via canula and the mixture was again degassed three times. The mixture was then heated at 85° C. for 5 h. Analysis by HPLC-MS indicated the reaction was not complete. The mixture was stirred at 85° C. for 5 more h. The mixture was then allowed to return to room temperature for overnight. 2-methylTHF (2 L) and brine were added, and the mixture was stirred for 5 min. The layers were separated and the aqueous layer was extracted again with 2-methylTHF. The organic layers were combined, washed three times with brine (4 L each), dried over MgSO$_4$, filtered, and concentrated. The crude product was purified by flash chromatography (1.5 kg silica cartridge), eluting with 0-20% ethyl acetate in dichloromethane to afford 5-(1,3-dioxolan-2-ylmethyl)-2-benzofuran-1(3H)-one. LC-MS (IE, m/z): 221 [M+1]$^+$.

Step B: (1-Oxo-1,3-dihydro-2-benzofuran-5-yl)acetaldehyde: 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred overnight at room temperature. The mixture was extracted three times with 2 L of ethyl acetate. The combined organic layers were concentrated to give (1-oxo-1,3-dihydro-2-benzofuran-5-yl)acetaldehyde. LC-MS (IE, m/z): 177 (M+1)$^+$.

Intermediate 2

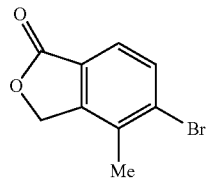 [SMILES: Cc1c(Br)ccc2c1COC2=O]

5-bromo-4-methyl-2-benzofuran-1(3H)-one

Step A: (3-bromo-2-methylphenyl)methanol: To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol. $^1$H NMR (500 MHz, CDCl$_3$) δ 7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one: To a flask charged with (3-bromo-2-methylphenyl)methanol (6.0 g, 30 mmol) was added a 1M TFA solution of thallium trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added palladium(II) chloride (529 mg, 2.98 mmol), lithium chloride (2.53 g, 59.7 mmol), magnesium oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a CELITE® pad, washed with EtOAc, adsorbed onto silica and purified by silica gel chromatography to afford title compound. $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Intermediate 3

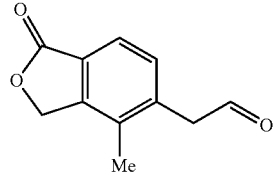 [SMILES: Cc1c(CC=O)ccc2c1COC2=O]

(4-Methyl-1-oxo-1,3-dihydro-2-benzofuran-5-yl) acetaldehyde

Step A: 4-Methyl-5-prop-2-en-1-yl-2-benzofuran-1(3H)-one: To a flask charged with 5-bromo-4-methyl-2-benzofuran-1(3H)-one (320 mg, 1.409 mmol) and a stir bar was added allyl tri-n-butyltin (0.655 mL, 2.11 mmol), Pd(PPh$_3$)$_4$ (244 mg, 0.211 mmol), lithium chloride (179 mg, 4.23 mmol), and toluene (15 mL). The reaction was purged with nitrogen 2 times then was heated at reflux for 4 hours. The product was separated by silica gel chromatography to give 4-methyl-5-prop-2-en-1-yl-2-benzofuran-1(3H)-one.

Step B: (4-Methyl-1-oxo-1,3-dihydro-2-benzofuran-5-yl) acetaldehyde: A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford the title compound. ¹H-NMR (500 MHz, CDCl₃) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

Intermediate 4

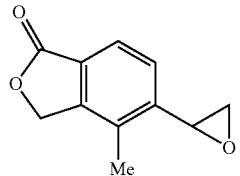 [SMILES: Cc1c(C2CO2)ccc2c1COC2=O]

4-methyl-5-oxiran-2-yl-2-benzofuran-1(3H)-one

Step A: 5-ethenyl-4-methyl-2-benzofuran-1(3H)-one: 5-Bromo-4-methyl-2-benzofuran-1(3H)-one (598 mg, 4.47 mmol), potassium vinyl trifluoroborate (507 mg, 2.23 mmol), PdCl₂(dppf)-CH₂Cl₂Adduct (182 mg, 0.223 mmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% EtOAc/Hexane solvent system to yield 5-ethenyl-4-methyl-2-benzofuran-1(3H)-one. ¹H-NMR (500 MHz, CDCl₃): δ ppm 7.76 (d, J=8 Hz, 1H), 7.03(dd, J=11, 17 Hz, 1H), 5.84 (d, J=17 Hz, 1H), 5.55 (d, J=11 Hz, 1H), 5.29 (s, 2H), 2.34 (s, 3H); LC-MS: M+1=175;

Step B: 4-methyl-5-oxiran-2-yl-2-benzofuran-1(3H)-one: 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na₂S₂O₃, NaHCO₃, and brine. The organic layer was dried over Na₂SO₄, filtered, and evaporated to dryness. The crude material was purified by MPLC chromatography through 120 g Redi-sep column eluting with 0-80% EtOAc/hexane solvent system to yield target 4-methyl-5-oxiran-2-yl-2-benzofuran-1(3H)-one. ¹H-NMR (500 MHz, CDCl₃): δ ppm 7.77 (d, J=8 Hz, 1H), 7.43 (d, J=8 Hz, 1H), 5.30 (s, 2 H), 4.12 (s, 1 H), 3.27 (t, J=4 Hz, 1 H), 2.735 (dd, J=2.2, 5.5 Hz, 1H), 2.43 (s, 3H). LC-MS: M+1=191.

Intermediates 4A and 4B (Method 1)

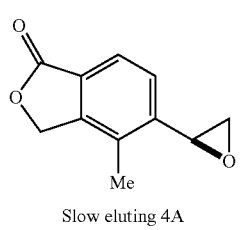

Slow eluting 4A

-continued

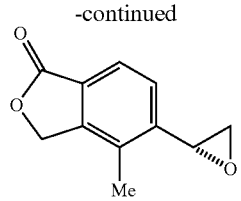

Fast eluting 4B

4A: 4-methyl-5-[(2S)-oxiran-2-yl]-2-benzofuran-1(3H)-one

4B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO₂, flow rate 200 mL/min, 100 bar, 25° C. 500 ul Injections were spaced every 2.12 mins. The fast epoxide (4-methyl-5-[(2R)-oxiran-2-yl]-2-benzofuran-1(3H)-one, 4B) eluted first, and the slow epoxide (4-methyl-5-[(2S)-oxiran-2-yl]-2-benzofuran-1(3H)-one, 4A) eluted second.

Alternatively, the resolution could also be achieved using a mobile phase of 8% MeOH 98% CO₂ with a flow rate of 100 mL/min. In that case the sample was prepared by dissolving in methanol, 20 mg/mL, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 4B and by Mosher ester and Trost ester HNMR analysis of esters made starting from 4B. Both epoxide isomers find utility in the present invention.

Intermediate 4B (Method 2)

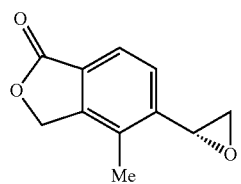 [SMILES: Cc1c([C@@H]2CO2)ccc2c1COC2=O]

4-methyl-5-[(2R)-oxiran-2-yl]-2-benzofuran-1(3H)-one

Step A: 3-hydroxymethyl-2-methyl phenol: To a 5 L 3 neck RB equipped with overhead stirrer was charged NaBH₄ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF₃—OEt₂ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol. $^1$H-NMR (400 MHz, DMSO-$d_6$): δ 9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H), 4.44 (d, J=5.5 Hz, 2H), 2.06 (s, 3H).

Step B: 4-Bromo-3-hydroxymethyl-2-methyl phenol: 3-Hydroxymethyl-2-methyl phenol (113.9 g, 824.0 mmol) was dissolved in a mixture of acetonitrile (850 mL) and trifluoroacetic acid (750.0 mL, 9.735 mmol) in a 3-neck 5-L flask under nitrogen. The reaction mixture was cooled to −3° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5.358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane: MTBE (500 mL), followed by heptane (500 mL). The solid was dried under vacuum, providing 4-bromo-3-hydroxymethyl-2-methyl phenol. $^1$H NMR (400 MHz, DMSO-$d_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C: 5-Hydroxy-4-methyl-3H-isobenzofuran-1-one: To a 2 L 3 neck flask equipped with overhead stirrer, $N_2$ inlet, and condenser were charged 4-bromo-3-hydroxymethyl-2-methyl phenol (100 g, 461 mmol), CuCN (83.0 g, 921 mmol), and DMF (500 mL). The solution was sparged with $N_2$ for 15 min then heated to 145° C. to obtain a homogeneous solution. The solution was aged at 145° C. for 2 h, then the reaction mixture was cooled to 95° C. 41.5 mL water was added (sparged with $N_2$), and the reaction aged for 20 h. The reaction was cooled to RT then the solids filtered through SOLKA FLOC® and the cake washed with 50 mL DMF. To a 3 L flask containing 1 L EtOAc was added the DMF filtrate. A precipitate coating formed in bottom of flask. The DMF/EtOAc suspension was filtered through SOLKA FLOC® and the cake was washed with 250 mL EtOAc. The resulting filtrate was washed with 5% brine solution (3×500 mL). The aqueous layers were extracted with 500 mL EtOAc and the combined organics were dried over $MgSO_4$, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one. $^1$H NMR (400 MHz, DMSO-$d_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D: 4-methyl-1-oxo-1,3-dihydroisobenzofuran-5-yl trifluoromethanesulfonate 5-Hydroxy-4-methyl-3H-isobenzofuran-1-one (46.8 g, 285 mmol) was suspended in dichloromethane (935 mL) in 2-L round bottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over SOLKA FLOC®, washing with additional dichloromethane, and transferred to a reparatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetatehexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydroisobenzofuran-5-yl ester. $^1$H NMR (400 MHz, $CDCl_3$): δ 7.87 (d, J=8.4 Hz, 1H), 7.47 (d, J=8.4 Hz, 1H), 5.32 (s, 2H), 2.41 (s, 3H)

Step E: 5-(1-Butoxy-vinyl)-4-methyl-3H-isobenzofuran-1-one: To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol)) then $Et_3N$ (35.6 mL, 255 mmol). The solution was sparged with $N_2$ for 20 min. To the solution was added $Pd(OAc)_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% $NH_4Cl$ (2×315 mL), 10% brine (2×315 mL), dried over $MgSO_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one. $^1$H NMR (400 MHz, DMSO-$d_6$): δ 7.67 (d, J=7.7 Hz, 1H), 7.48 (d, J=7.7 Hz, 1H), 5.42 (s, 2H), 4.54 (d, J=2.3 Hz, 1H), 4.27 (d, J=2.3 Hz, 1H), 3.85 (t, J=6.4 Hz, 2H), 2.27 (s, 3H), 1.71-1.64 (m, 2H), 1.46-1.37 (m, 2H), 0.92 (t, J=7.4 Hz, 3H)

Step F: 5-(2-Bromo-acetyl)-4-methyl-3H-isobenzofuran-1-one: To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portion-wise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 ml, of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one. $^1$H NMR (400 MHz, DMSO-$d_6$): δ 7.99 (d, J=7.8 Hz, 1H), 7.82 (d, J=7.8 Hz, 1H), 5.49 (s, 2H), 4.92 (s, 2H), 2.33 (s, 3H)

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck round bottom equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 ml, IPAc (thick slurry). Hexanes were added (400 mL) and the suspension aged at RT then filtered and washed w 5:1 Hexanes:IPAc solution (150 mL). The crystalline solids were dried under vacuum at RT to provide 4-methyl-5-[(2R)-oxiran-2-yl]-2-benzofuran-1(3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H).

Intermediate 5

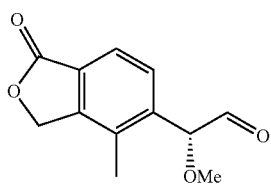 [SMILES: CO[C@@H](C=O)c1ccc2c(c1C)COC2=O]

(R)-2-Methoxy-2-(4-methyl-1-oxo-1,3-dihydroisobenzofuran-5-yl)acetaldehyde

Step A: (R)-5-(2-Hydroxy-1-methoxyethyl)-4-methylisobenzofuran-1(3H)-one: To a solution of (S)-4-methyl-5-(oxiran-2-yl)isobenzofuran-1(3H)-one (2.00 g, 10.5 mmol) in MeOH (20 mL) was added p-toluenesulfonic acid monohydrate (0.100 g, 0.526 mmol). After heating at 80° C. for 48 h, the reaction mixture was cooled to RT and then concentrated. The crude product was purified by column chromatography eluting with 0-45% EtOAc/Hexane. LC-MS (IE, m/z): 223.2 (M+1)$^+$.

Step B: (R)-2-Methoxy-2-(4-methyl-1-oxo-1,3-dihydroisobenzofuran-5-yl)acetaldehyde: (R)-5-(2-Hydroxy-1-methoxyethyl)-4-methylisobenzofuran-1(3H)-one (500 mg, 2.25 mmol) was dissolved in DCM (10 mL) and treated with Dess-Martin periodinane (954 mg, 2.25 mmol). The reaction mixture was stirred at room temperature under nitrogen overnight. The crude product was used directly. LC-MS (IE, m/z): 239.2 (M+H$_2$O+1)$^+$.

Intermediate 6

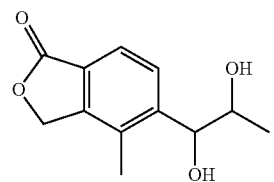 [SMILES: Cc1c(C(O)C(C)O)ccc2c1COC2=O]

5-(1,2-Dihydroxypropyl)-4-methylisobenzofuran-1(3H)-one

Step A: (E)-4-Methyl-5-(prop-1-en-1-yl)isobenzofuran-1(3H)-one: To Pd(dppf)Cl$_2$ (0.220 g, 0.338 mmol), K$_3$PO$_4$ (6.75 mL, 1 M in water, 6.75 mmol) in THF (22 mL) was added potassium (E)-trifluoro(prop-1-en-1-yl)borate (0.749 g, 5.06 mmol) and 4-methyl-1-oxo-1,3-dihydroisobenzofuran-5-yltrifluoromethanesulfonate (I-4B, Method 2, step D, 1.0 g, 3.38 mmol). The reaction mixture was de-gassed for 10 min and the resulting mixture was stirred overnight at 70° C. The reaction mixture was cooled to room temperature and diluted with EtOAc and water. After separation of layers, the aqueous layer was extracted with EtOAc, and combined organic layers were washed with brine, dried over anhydrous MgSO$_4$, filtered, concentrated and purified by silica gel column chromatography using (0-50%) acetone-hexanes as mobile phase to give the title compound. LCMS: [(M+1)]$^+$=189

Step B: 5-(1,2-Dihydroxypropyl)-4-methylisobenzofuran-1(3H)-one: To (E)-4-methyl-5-(prop-1-en-1-yl)isobenzofuran-1(3H)-one (300 mg, 1.59 mmol) in acetonitrile/water (10/1, 18 mL) was added NMO (243 mg, 2.07 mmol) and potassium osmate(VI) dihydrate (29.4 mg, 0.080 mmol) at 0° C. The reaction mixture was allowed to warm to rt and stirred at rt for 2 h. TLC showed the reaction completed. The reaction mixture was filtered through a pad of silica gel, rinsed with 10% MeOH/DCM. The crude product was purified with column chromatography (0-10% MeOH/DCM) to give the title compound. LCMS: [(M+1)]$^+$=223

Intermediate 7

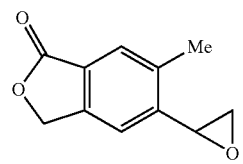 [SMILES: Cc1cc2c(cc1C1CO1)COC2=O]

6-methyl-5-oxiran-2-yl-2-benzofuran-1(3H)-one

Step A: 5-prop-2-en-1-yl-2-benzofuran-1(3H)-one: A mixture of 5-bromo-2-benzofuran-1(3H)-one (15.0 g, 70.4 mmol), allyl-tributyl-stannane (25.6 g, 77.5 mmol), LiCl (11.8 g, 282 mmol) and Pd(PPh$_3$)$_4$ (1.2 g, 1.0 mmol) in 100 mL toluene was heated under N$_2$ at 90~100° C. overnight.

After cooling to r.t., the mixture was diluted with 250 mL EtOAc and filtered. The filtrate was washed with water and brine, dried over anhydrous $Na_2SO_4$ and concentrated to dryness. The residue was purified via column (DCM/Petrol Ether=1:5) to give the title compound.

Step B: 5-(2-hydroxyethyl)-2-benzofuran-1(3H)-one: To a solution of 5-prop-2-en-1-yl-2-benzofuran-1(3H)-one (13.5 g, 45.2 mmol) in 200 mL DCM/MeOH (V/V=1:1) was bubbled $O_3$ at −78° C. for 30 min, and $N_2$ was bubbled for another 15 min at −78° C. Then 20 mL of $Me_2S$ were added, and the mixture was stirred at r.t. overnight before concentrating to dryness. The residue was dissolved in MeOH (100 mL) and then cooled to 0° C. $NaBH_4$ (5.90 g, 155 mmol) was added in portions. The resulting mixture was stirred at 0° C. for 1 h, then quenched with citric acid (aq.) and extracted three times with EtOAc. The combined organic layers were washed with $NaHCO_3$ (aq.) and brine, dried over anhydrous $Na_2SO_4$ and concentrated to dryness. The residue was purified via column chromatography (EtOAc/Petrol Ether=1:5) to give the title compound. $^1$H-NMR (400 MHz, $CDCl_3$) δ ppm 7.86 (d, J=7.8 Hz, 1H), 7.41 (d, J=7.8 Hz, 1H), 7.38 (s, 1H), 5.29 (s, 2H), 3.92-3.98 (m, 2H), 3.01 (t, J=6.4 Hz, 2H).

Step C: 5-(2-hydroxyethyl)-6-iodo-2-benzofuran-1(3H)-one: To a cooled (0° C.) solution of 5-(2-hydroxyethyl)-2-benzofuran-1(3H)-one (9.00 g, 50.6 mmol) in 100 mL of TfOH was added NIS (12.5 g, 55.6 mmol), then the mixture was stirred at 0° C. for 2 hrs and then poured into ice-water (500 mL). The solution was extracted three times with 500 mL of EtOAc and the combined organic layers were washed with saturated $NaHCO_3$ and brine, dried over anhydrous sodium sulfate, filtered and concentrated. The residue was purified by column chromatography (EtOAc Petrol Ether=1:5) to give the desired 5-(2-hydroxyethyl)-6-iodo-2-benzofuran-1(3H)-one and regioisomer by-product 5-(2-hydroxyethyl)-4-iodo-2-benzofuran-1(3H)-one. $^1$H-NMR (400 MHz, $CDCl_3$) δ ppm 7.84 (d, J=7.8 Hz, 1H), 7.46 (d, J=7.8 Hz, 1H), 5.09 (s, 2H), 3.93 (q, J=6.3 Hz, 2H), 3.16 (t, J=6.3 Hz, 2H), 1.45 (t, J=5.5 Hz, 1H).

Step D: 5-(2-hydroxyethyl)-6-methyl-2-benzofuran-1(3H)-one: To a flask charged with 5-(2-hydroxyethyl)-6-iodo-2-benzofuran-1(3H)-one (6.00 g, 19.7 mmol) and a stir bar was added $Pd_2(dba)_3$ (452 mg, 0.493 mmol), $PPh_3$ (1 g, 4 mmol) and NMP (50 mL). The mixture was purged with $N_2$ and heated to 50° C. for 10 min, followed by addition of CuI (375 mg, 1.97 mmol). After the mixture was heated for another 10 min, $Sn(CH_3)_4$ (5.30 g, 29.6 mmol) was added into the reaction, and it was heated to 120° C. for 2 h. After cooling to room temperature, the mixture was diluted with saturated $NH_4Cl$ (200 mL) and extracted with EtOAc (3 times 200 mL). The combined organic layers were washed with water and brine, dried over anhydrous sodium sulfate, filtered and concentrated. The residue was purified by prep-HPLC to give the title compound. $^1$H-NMR (400 MHz, $CDCl_3$) δ ppm 7.72 (s, 1H), 7.33 (s, 1H), 5.27 (s, 2H), 3.93 (t, J=6.3 Hz, 2H), 3.01 (t, J=6.3 Hz, 2H), 2.44 (s, 3H).

Step E: 2-(6-methyl-1-oxo-1,3-dihydro-2-benzofuran-5-yl)ethyl methanesulfonate: To a solution of 5-(2-hydroxyethyl)-6-methyl-2-benzofuran-1(3H)-one (1.20 g, 6.25 mmol) and TEA (2.5 g, 25 mmol) in DCM (100 mL) was added MsCl (1.40 g, 12.5 mmol) at 0° C. The mixture was stirred at ambient temperature overnight, then was washed with water and brine. The organic layer was dried and concentrated to dryness. The collected title compound was used for the next step without any purification.

Step F: 5-ethenyl-6-methyl-2-benzofuran-1(3H)-one: To a mixture of 2-(6-methyl-1-oxo-1,3-dihydro-2-benzofuran-5-yl)ethyl methanesulfonate (2.00 g, 7.41 mmol) and TEA (5 mL) in DCM (50 mL) was added DBU (5 mL) slowly at 0° C. The mixture was stirred at r.t. overnight, and then was diluted with 50 mL of DCM, washed with 2 N HCl in three times and brine. The organic layer was dried and concentrated to dryness. The residue was purified by prep-TLC to give 5-ethenyl-6-methyl-2-benzofuran-1(3H)-one.

Step G: 6-methyl-5-oxiran-2-yl-2-benzofuran-1(3H)-one: To a solution of 5-ethenyl-6-methyl-2-benzofuran-1(3H)-one (1.00 g, 5.75 mmol) in 50 mL of DCM was slowly added mCPBA (3.50 g, 17.4 mmol) in 50 mL of DCM at 0° C. The mixture was warmed to room temperature, and stirred for 2 days. The mixture was washed with aqueous $Na_2SO_3$ until KI indicator paper didn't change color. The organic layer was washed with brine and then concentrated. The residue was purified via silica column to give the title compound. LC-MS M+1 (calc. 191. found 191).

Intermediates 7A and 7B

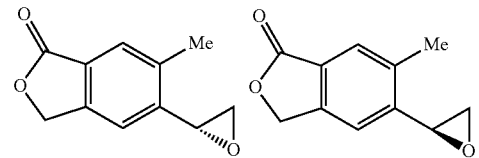

(R)-6-methyl-5-(oxiran-2-yl)isobenzofuran-1(3H)-one and (S)-6-methyl-5-(oxiran-2-yl)isobenzofuran-1(3H)-one: The title compounds were obtained by chiral SFC separation of the racemic 6-methyl-5-oxiran-2-yl-2-benzofuran-1(3H)-one (I-7) using a chiralpak AD column (250 mm×50 mm, 10 um); mobile phase: A: Supercritical $CO_2$, B: MeOH, A:B=85:15 at 250 ml/min. First peak to elute (Isomer 7A): $^1$HNMR 400 MHz $CDCl_3$, δ 7.68 (s, 1H), 7.36 (s, 1H), 5.24 (d, J=3.6 Hz, 2H), 4.05 (dd, J=2.8 Hz, 3.6 Hz, 1H), 3.24 (dd, J=4.0 Hz, 6.4 Hz, 1H), 2.63 (dd, J=2.8 Hz, 6.4 Hz, 1H), 2.50 (s, 3H); second peak to elute (Isomer 7B): 400 MHz $CDCl_3$, δ 7.68 (s, 1H), 7.35 (s, 1H), 5.24 (d, J=3.6 Hz, 2H), 4.05 (dd, J=2.8 Hz, 3.6 Hz, 1H), 3.24 (dd, J=4.0 Hz, 6.4 Hz, 1H), 2.63 (dd, J=2.8 Hz, 6.4 Hz, 1H), 2.50 (s, 3H).

Intermediate 8

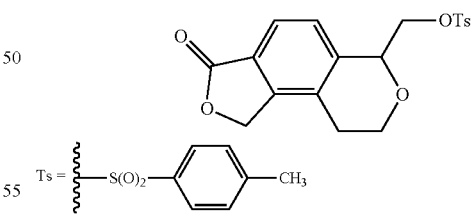

(3-oxo-3,6,8,9-tetrahydro-1H-furo[3,4-f]isochromen-6-yl)methyl-4-methylbenzenesulfonate Step A: 5-bromo-4-iodo-2-benzofuran-1(3H]-one: To a solution of 5-bromo-2-benzofuran-1(3H)-one (5.00 g, 23.5 mmol) at 0° C. in TfOH (100 mL) was added NIS (5.55 g, 24.6 mmol). The mixture was stirred at room temperature overnight; LC analysis of the reaction mixture indicated completion of the reaction. The reaction mixture was then poured slowly into ice-water (1 L) with stirring. To the solution was then added EtOAc (500 mL) and subsequently stirred for 10 min. The mixture was filtered and the organic layer separated. The aqueous layer was extracted with EtOAc (2×200 mL). The combined organic layers were washed with water (500 mL), brine (500 mL), dried over $Na_2SO_4$, filtered, and concentrated to dryness; the resulting material was absorbed onto silica gel and separated with the solvent system of (hexanes/EtOAc=1/1) to yield 5-bromo-4-iodo-2-benzofuran-1(3H]-one.

Step B: 5-bromo-4-prop-2-en-1-yl-2-benzofuran-1(3H]-one: A mixture of 5-bromo-4-iodo-2-benzofuran-1(3H]-one (2.42 g, 7.13 mmol), allyltributyltin (2.36 g, 7.13 mmol), LiCl (1.50 g, 35.7 mmol) and Pd $(PPh_3)_4$ (200 g, 0.173 mmol) in toluene (50 mL) was heated at 90-100° C. under $N_2$ overnight; LC indicated that reaction had gone to completion, to the solution was poured EtOAc (100 mL) and washed with brine. The organic layer was dried over $Na_2SO_4$, filtered and concentrated to dryness, absorbed into silica gel and was then separated over silica gel column to give the title compound.

Step C: 5-bromo-4-(2-hydroxyethyl)-2-benzofuran-1 (3H)-one: To a solution of 5-bromo-4-prop-2-en-1-yl-2-benzofuran-1(3H)-one (1.27 g, 5.02 mmol) in MeOH (50 mL) and DCM (50 mL) was bubbled $O_3$ at −78° C. until the solution turned blue; excess ozone was removed on high vacuum. After the solution's color changed to colorless, $NaBH_4$ (0.8 g, 20 mmol) was added to the reaction mixture and it was subsequently stirred at room temperature for 30 min. LC and TLC indicated that reaction had gone to completion. The solvent was removed on high vacuum; the residue was then re-dissolved in EtOAc and washed with water, dried over $Na_2SO_4$, filtered and concentrated to dryness. The organic residue was absorbed onto silica gel and was separated on silica gel column to give the title compound.

Step D: 5-ethenyl-4-(2-hydroxyethyl)-2-benzofuran-1 (3H)-one: A mixture of 5-bromo-4-(2-hydroxyethyl)-2-benzofuran-1(3H)-one (0.460 g, 1.78 mmol), tributyl(vinyl)tin (0.676 g, 2.13 mmol), LiCl (0.224 g, 5.33 mmol) and Pd $(PPh_3)_4$ (0.10 g, 0.087 mmol) in toluene (50 mL) was heated at 100-110° C. under $N_2$ overnight after which TLC indicated that the reaction had gone to completion. Next, EtOAc (100 mL) was poured into the solution and it was washed with brine, then water, then dried over $Na_2SO_4$, filtered and concentrated to dryness. The residue was then absorbed onto silica gel and separated over silica column to give the title compound.

Step E: 4-(2-hydroxyethyl)-5-oxiran-2-yl-2-benzofuran-1 (3H)-one: 5-Ethenyl-4-(2-hydroxyethyl)-2-benzofuran-1 (3H)-one (1.2 g, 5.9 mmol) was added to a flask containing a stir bar. To the flask was then added dichloromethane (20 mL). The flask was placed in a cool bath of 0° C.; to the flask was poured mCPBA (1.5 g, 8.8 mmol) and the resulting mixture was stirred at room temperature for overnight; LC as well as TLC (hexanes/EtOAc=1/1) indicated that reaction had gone to completion. The solution was treated with dichloromethane and washed with $NaHCO_3$, $Na_2S_2O_3$, and water, the organic layer was then dried over $Na_2SO_4$, filtered and concentrated to dryness, it was then treated with AcOH (20 mL) and stirred overnight; LC indicated formation of cyclized product. The solvent was removed and the resulting residue was absorbed onto silica gel and the title compound was isolated with the solvent system of hexanes/EtOAc (1/1).

Step F: (3-oxo-3,6,8,9-tetrahydro-1H-furo[3,4-f]isochromen-6-yl)methyl-4-methylbenzenesulfonate: 6-(Hydroxymethyl)-8,9-dihydro-1H-furo[3,4-f]isochromen-3 (6H)-one, in DCM (10 mL) was treated with p-Toluenesulfonyl chloride (0.40 g, 2.3 mmol); to the mixture was added pyridine (2 mL) and the resulting mixture stirred at room temperature for 12 h. TLC (hexanes/EtOAc=10.5) and LC indicated the consumption of starting material and formation of the desired product. Dichloromethane was added to the reaction mixture and it was washed with NaCl, water and dried over $Na_2SO_4$, filtered and concentrated to dryness, absorbed onto silica gel and was then subjected to purification over silica gel; the title compound was isolated with the solvent system of hexanes/EtOAc (10.5). $^1$H-NMR (400 MHz, $CDCl_3$) δ ppm 7.781 (d, J=8 Hz, 1H), 7.727 (d, J=8 Hz, 1H), 7.367 (d, J=8 Hz, 1H), 7.257 (d, J=8.5 Hz, 1H), 7.206 (d, J=8 Hz, 1H), 5.253 (s, 2H), 5.110 (s, 1H), 4.481-4.452 (m, 2H), 4.419-4.385 (m, 2H), 4.196-4.153 (m, 2H), 2.495 (s, 3H).

Intermediate 9

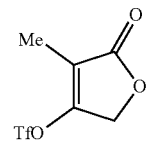

4-methyl-5-oxo-2,5-dihydrofuran-3-yltrifluoromethanesulfonate

Step A: ethyl 4-bromo-2-methyl-3-oxobutanoate: To a solution of ethyl 2-methyl-3-oxobutanoate (5.05 g, 35.0 mmol) in water (10 mL) at 0° C. was added bromine (1.81 mL, 35.0 mmol) dropwise over 2 h. The resulting solution was stirred at rt for 16 h. The reaction mixture was extracted with ethyl acetate, the organic phase was dried over sodium sulfate and concentrated to give ethyl 4-bromo-2-methyl-3-oxobutanoate. $^1$HNMR (500 MHz, $CDCl_3$), δ4.322-4.274 (m, 2H), 2.455 (s, 2H), 1.991 (s, 3H), 1.337-1.309 (t, 3H).

Step B: 4-hydroxy-3-methylfuran-2(5H)-one: Ethyl 4-bromo-2-methyl-3-oxobutanoate (7.81 g, 35 mmol) was treated with hydrogen bromide (0.040 mL, 48%, 0.35 mmol) and the mixture was heated at 100° C. for 6 h. The precipitate was collected by filtration followed by washing with ethyl acetate to give 4-hydroxy-3-methylfuran-2(5H)-one. $^1$HNMR (500 MHz, $CDCl_3$), δ4.595 (s, 2H), 3.314 (s, 1H), 1.668 (s, 3H).

Step C: 4-methyl-5-oxo-2,5-dihydrofuran-3-yltrifluoromethanesulfonate: To a solution of 4-hydroxy-3-methylfuran-2(5H)-one (400 mg, 3.51 mmol) in dichloromethane (10 mL) at −78° C. was added 2,6-lutidine (0.612 mL, 5.26 mmol) and triflic anhydride (0.711 mL, 4.21 mmol) dropwise. The reaction temperature was maintained at −78° C. for 0.5 h before being warmed to rt for 1 h. The mixture was diluted with DCM (100 mL) and washed with 1N hydrogen chloride (3 times 100 mL), then with diluted sodium bicarbonate solution, then dried over sodium sulfate, and concentrated to give the title compound. LCMS: $(M+1)^+$: 247.0.

Intermediate 10

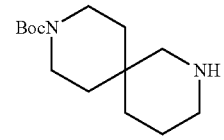

tert-Butyl 3,8-diazaspiro[5,5]undecane-3-carboxylate

Step A: tert-Butyl 4-(hydroxymethyl)piperidinecarboxylate: A mixture of 70 g of LiAlH$_4$ in 1500 mL of THF was cooled to 0° C., then 180 g of 1-tert-butyl 4-methyl piperidine-1,4-dicarboxylate in THF was added dropwise. When the reaction was finished, 200 mL of ethyl acetate and solid anhydrous Na$_2$SO$_4$. Water was added until the solution became clear. The mixture was filtered and the filtrate was evaporated to afford the title compound.

Step B: tert-Butyl 4-formypiperidinecarboxylate: The solution of 200 mL of DMSO in CH$_2$Cl$_2$ cooled to −78° C., 118 mL of (COCl)$_2$ was added drop-wise. Then 255 g of tert-butyl 4-(hydroxymethyl)piperidinecarboxylate was also added drop-wise. The mixture was stirred for 4 h. After the reaction was finished, 638 mL of Et$_3$N was added at −78° C. The organic layer was washed by brine, dried and purified by column chromatography to afford the title compound.

Step C: tert-Butyl 4-formyl-4-propylpiperidinecarboxylate: tert-Butyl 4-formypiperidinecarboxylate was dissolved in 66 mL of acrylonitrile, and 5 g of 50% aq. sodium hydroxide solution was added, then the mixture was heated to 50° C., until the reaction was complete as judged by TLC. The mixture was then poured into 700 mL of ether, then washed with brine and purified with column chromatography to afford title compound.

Step D: tert-Butyl 3,8-diazaspiro[5,5]undecane-3-carboxylate: Tert-butyl 4-formyl-4-propylpiperidinecarboxylate (30 g) was dissolved in a saturated solution of ammonia in methanol, and 15 g of Raney Ni was added. The reaction mixture was heated to 110° C. at 80 atmospheres pressure in a 2 L high-pressure autoclave. The mixture was filtered to remove the catalyst and the filtrate was concentrated to give residue which was purified by column chromatography to afford tert-butyl 3,8-diazaspiro[5,5]undecane-3-carboxylate.

Intermediate 11

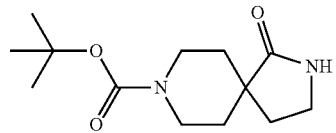 [SMILES: CC(C)(C)OC(=O)N1CCC2(CCNC2=O)CC1]

tert-Butyl 1-oxo-2,8-diazaspiro[4.5]decane-8-carboxylate: The title compound is commercially available from a number of vendors, for example, Shanghai AQ BioPharma Co., Ltd, catalog #ABP1882. Alternatively, it may be prepared in various ways, including the procedure described below.

Step A: 1-tert-Butyl 4-methyl 4-(cyanomethyl)piperidine-1,4-dicarboxylate: To a solution of commercially available 1-tert-butyl 4-methyl piperidine-1,4-dicarboxylate (200 g, 0.82 mol) in anhydrous THF (2 L) was added LDA (2M in THF, 575 mL, 1.15 mol) drop-wise at −65° C. under N$_2$. The mixture was stirred at −65° C. for 1.5 h. To the mixture was added bromoacetonitrile (148 g, 1.23 mol) in anhydrous THF (500 mL) at −65° C. The mixture was stirred at −65° C. for 1 h, then warmed up to room temperature and stirred overnight. The reaction was quenched with water (800 mL) at 0° C. and the combined reaction mixture was concentrated in vacuum to give a crude product, which was extracted with ethyl acetate (1 L three times). The combined organic phases were washed with brine (1 L) and dried over Na$_2$SO$_4$. The organic layer was filtered and the filtrate was concentrated under vacuum to give a crude product, which was purified by column chromatography on silica gel eluting with petroleum ether/ethyl acetate (from petroleum ether to 2/1) to give the title compound. $^1$H-NMR (400 MHz, CDCl$_3$) δ 3.900-3.750 (m, 5H), 3.120-3.000 (m, 2H), 2.612-2.562 (m, 2H), 2.190-2.111 (m, 2H), 1.590-1.502 (m, 2H), 1.402 (s, 9H).

Step B: tert-Butyl 1-oxo-2,8-diazaspiro[4.5]decane-8-carboxylate: A suspension of 1-tert-butyl 4-methyl 4-(cyanomethyl)piperidine-1,4-dicarboxylate (70.0 g, 247.9 mmol) and Raney Ni (60 g) in MeOH (1500 mL) and NH$_3$.H$_2$O (80 mL) was stirred at 2 MPa of hydrogen pressure at 50° C. for 18 h. The reaction mixture was filtered through a pad of CELITE® and the filtrate was concentrated under vacuum to give a crude product, which was washed with ethyl acetate (200 mL) to give the title compound. $^1$H-NMR (400 MHz, CDCl$_3$) δ 6.05 (s, 1H), 4.0 (s, 2H), 3.37-3.34 (m, 2H), 3.02-2.96 (m, 2H), 2.08-2.05 (m, 2H), 1.88-1.87 (m, 2H), 1.51-1.41 (m, 11H)

Intermediate 12

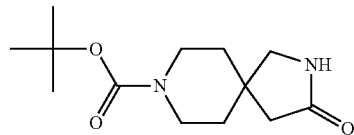 [SMILES: CC(C)(C)OC(=O)N1CCC2(CC1)CNC(=O)C2]

3-oxo-2,8-diaza-spiro[4,5]decane-8-carboxylic acid tert-butyl ester

Step A: tert-butyl 4-(2-ethoxy-2-oxoethylidene)piperidine-1-carboxylate: Into a 10-L 4-necked round-bottom flask purged and maintained with an inert atmosphere of nitrogen was placed a suspension of NaH (74.0 g, 2.16 mol 1.05 equiv, 70%) in tetrahydrofuran (2000 mL) at 0° C., then ethyl 2-(diethoxyphosphoryl)acetate (514 g, 2.06 mol, 1.05 equiv, 98%) was added dropwise with stirring at 0° C. This was followed by the addition of a solution of tert-butyl 4-oxopiperidine-1-carboxylate (400 g, 1.97 mol, 1.00 equiv, 98%) in tetrahydrofuran (1200 mL) dropwise with stirring at 0° C. The resulting solution was stirred for 60 min at room temperature, then quenched by the addition of 2000 mL of water. The resulting solution was extracted with 2×1000 mL of ethyl acetate. The organic layers were combined, dried over anhydrous magnesium sulfate and concentrated under vacuum. The residue was washed with 1×1000 mL of hexane and dried to afford tert-butyl 4-(2-ethoxy-2-oxoethylidene)piperidine-1-carboxylate.

Step B: tert-butyl 4-(2-ethoxy-2-oxoethyl)-4-(nitromethyl)piperidine-1-carboxylate: Into a 3000-mL 4-necked round-bottom flask was placed potassium carbonate (93.2 g, 662 mmol, 0.50 equiv) and DMSO (2000 mL). The resulting solution was heated to 80° C. This was followed by the addition of tert-butyl 4-(2-ethoxy-2-oxoethylidene)piperidine-1-carboxylate (368 g, 1.30 mol, 1.00 equiv, 95%) and CH$_3$NO$_2$ (417 g, 6.70 mol, 5.00 equiv, 98%) slowly. The resulting solution was stirred for 120 min at 90° C. After being cooled to room temperature, the reaction mixture was adjusted to ph 5 with HCl (0.5 mol/L) and diluted with 2000 mL of water. The resulting solution was extracted with 3×1500 mL of ether. The organic layers were combined, washed with 1×2000 mL of water and 1×2000 mL of saturated brine, dried and concentrated under vacuum. The residue was applied onto a silica gel column and eluted with ethyl acetate/petroleum ether (1:20~1:15~1:10) to afford the title compound.

Step C: 3-oxo-2,8-diaza-spiro[4,5]decane-8-carboxylic acid tert-butylester: A mixture of tert-butyl 4-(2-ethoxy-2-oxoethyl)-4-(nitromethyl)piperidine-1-carboxylate (330 g, 990 mmol, 1.00 equiv, 99%) and Ni (40 g, 0.15 equiv) in ethanol (1200 mL) was stirred for 24 h under a hydrogen atmosphere at room temperature. The solid was filtered out. The filtrate was concentrated under vacuum. The crude product was purified by re-crystallization from ether to afford the title compound. LC-MS (ES, m/z): 199 [M+H]$^+$; $^1$H-NMR (400 MHz, CDCl$_3$, ppm): 1.447-1.476(9H, s), 1.597-1.673 (4H, m, J=30.4 Hz), 2.235(2H, s), 3.226(2H, s), 3.284-3.348 (2H, m, J=25.6 Hz), 3.507-3.567(2H, m, J=24 Hz), 6.048(1H, s).

Intermediate 13

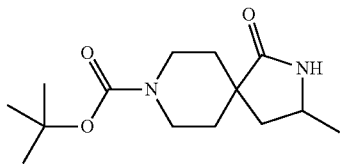 [SMILES: CC1CC2(CCN(C(=O)OC(C)(C)C)CC2)C(=O)N1]

tert-Butyl 3-methyl-1-oxo-2,8-diazaspiro[4.5]decane-8-carboxylate

Step A: 1-tert-Butyl 4-methyl 4-(2-methylallyl)piperidine-1,4-dicarboxylate: A solution of N-Boc-piperidine-4-carboxylic acid methyl ester (2.00 g, 8.22 mmol) in THF (40 mL) was cooled to −78° C. Under nitrogen, a 2.0 M THF solution of LDA (6.17 mL, 12.3 mmol) was added dropwise. The reaction mixture was stirred at −78° C. for 30 minutes before a solution of 3-bromo-2-methylpropene (1.60 g, 11.9 mmol) in THF (2 mL) was added. After the reaction was stirred for 1 hour at this temperature, a sample was taken for LC-MS analysis and it showed that the reaction was completed. The reaction was quenched by adding saturated ammonium chloride solution (5 mL) and the mixture was allowed to warm up to room temperature. The mixture was then extracted with EtOAc (50 mL twice). The combined organic layers were washed with brine (30 mL), dried over anhydrous sodium sulfate and filtered. The filtrates were concentrated and the crude product was purified by column chromatography eluting with 0-30% ethyl acetatehexane to give the title compound. LC-MS (IE, m/z): 242.21 [M−56+1]$^+$.

Step B: 1-tert-Butyl 4-methyl 4-(2-oxopropyl)piperidine-1,4-dicarboxylate: To a solution of 1-tert-butyl 4-methyl 4-(2-methylallyl)piperidine-1,4-dicarboxylate (2.2 g, 7.4 mmol) in dioxane/water (60 mL, 1/1) under nitrogen was added osmium tetroxide (0.038 g, 0.15 mmol) and sodium periodate (2.88 g, 13.5 mmol). The mixture was stirred at room temperature for 3 hours. The mixture was then diluted with dichloromethane (50 mL), and washed with 20% Na$_2$S$_2$O$_3$ (20 mL). The organic layers were combined and washed with brine (20 mL), dried over anhydrous sodium sulfate, and filtered. The filtrates were concentrated and the residue was purified by column chromatography eluting with 0-60% ethyl acetatehexane to afford 1-tert-butyl 4-methyl 4-(2-oxopropyl)piperidine-1,4-dicarboxylate. LC-MS (IE, m/z): 322.26 (M+23)$^+$.

Step C: tert-Butyl 3-methyl-1-oxo-2,8-diazaspiro[4.5]decane-8-carboxylate: 1-tert-Butyl 4-methyl 4-(2-oxopropyl)piperidine-1,4-dicarboxylate (1.15 g, 3.84 mmol) in methanol (25 mL) was treated with ammonium acetate (3.85 g, 49.9 mmol), sodium cyanoborohydride (0.681 g, 10.83 mmol) and magnesium sulfate (2.54 g, 21.1 mmol). The mixture was heated at 80° C. in a sealed tube for 12 hours. The reaction mixture was filtered through a pad of CELITE® and the filter cake was washed with methanol. The filtrates were then concentrated and the residue was purified by column chromatography eluting with 0-10% methanol/ethyl acetate to afford the title compound. LC-MS (IE, m/z): 291.27 (M+23)$^+$ Intermediates 13A and 13B

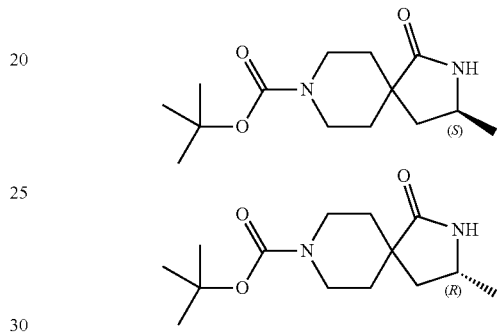

(S)-tert-Butyl 3-methyl-1-oxo-2,8-diazaspiro[4.5]decane-8-carboxylate; and (R)-tert-Butyl 3-methyl-1-oxo-2,8-diaz aspiro[4.5]decane-8-carboxylate tert-Butyl 3-methyl-1-oxo-2,8-diazaspiro[4.5]decane-8-carboxylate was subjected to SFC purification. The two enantiomers were resolved on a Chiralcel IA column eluting with 30% MeOH:MeCN (2:1)/CO$_2$ (100 bar, 35° C.). The faster eluting isomer was determined to be (S)-tert-Butyl 3-methyl-1-oxo-2,8-diazaspiro[4.5]decane-8-carboxylate and the slower eluting isomer was (R)-tert-Butyl 3-methyl-1-oxo-2,8-diazaspiro[4.5]decane-8-carboxylate based on Vibrational Circular Dichroism (VCD) spectroscopy analysis. LC-MS (IE, m/z): 291 (M+23)$^+$.

Intermediate 14

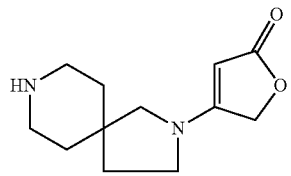 [SMILES: O=C1C=C(N2CCC3(CCNCC3)C2)CO1]

4-(2,8-diazaspiro[4.5]decan-2-yl)furan-2(5H)-one: Commercially available furan-2,4(3H,5H)-dione (0.433 g, 4.33 mmol) and tert-butyl 2,8-diazaspiro[4.5]decane-8-carboxylate (commercially available from multiple vendors, acetic acid salt, 0.65 g, 2.2 mmol) in 20 mL i-PrOH was heated in a sealed tube at 110° C. overnight. The solid was filtered off and the filtrate was concentrated under vacuum. The residue was dissolved in 30 mL DCM and 5 mL TFA and stirred at rt for 1 h. The mixture was concentrated, and the residue was purified by preparative TLC (10% 2N NH₃ in methanol-DCM). LCMS: [(M+1)]⁺=223

Intermediate 15

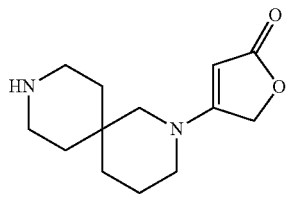 [SMILES: O=C1C=C(N2CCCC3(CCNCC3)C2)CO1]

4-(2,9-Diazaspiro[5.5]undecan-2-yl)furan-2(5H)-one

Step A: tert-Butyl 2-(5-oxo-2,5-dihydrofuran-3-yl)-2,9-diazaspiro[5.5]undecane-9-carboxylate To commercially available 4-bromofuran-2(5H)-one (128 mg, 0.786 mmol) in THF (4 mL) was added Hunig's Base (275 µL, 1.57 mmol) and tert-butyl 3,8-diazaspiro[5,5]undecane-3-carboxylate (200 mg, 0.786 mmol). The reaction mixture was stirred at 76° C. overnight, concentrated and purified by column chromatography (0-10% MeOH in DCM) to afford the title compound. LCMS: [(M+1)]⁺=337

Step B: 4-(2,9-Diazaspiro[5.5]undecan-2-yl)furan-2(5H)-one: To tert-butyl 2-(5-oxo-2,5-dihydrofuran-3-yl)-2,9-diazaspiro[5.5]undecane-9-carboxylate (266 mg, 0.792 mmol) in DCM (2 mL) was added TFA (2 mL, 26.0 mmol) at 0° C. The reaction mixture was stirred at room temperature for 1 h, then concentrated under reduced pressure, then placed on the high vacuum. The residue was dissolved in MeOH and loaded onto a 2 g Bond Elut SCX column (pre-rinsed with MeOH). These were rinsed with MeOH, and the product was eluted via 2M NH₃ in MeOH to afford 4-(2,9-diazaspiro[5.5]undecan-2-yl)furan-2(5H)-one. LC/MS: [(M+1)]⁺=237

Intermediate 16

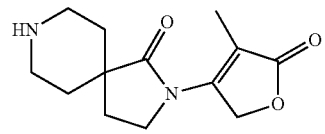

2-(5-oxo-2,5-dihydrofuran-3-yl)-2,8-diazaspiro[4.5]decan-1-one

Step A: tert-butyl 1-oxo-2-(5-oxo-2,5-dihydrofuran-3-yl)-2,8-diazaspiro[4.5]decane-8-carboxylate: A mixture of tert-butyl 1-oxo-2,8-diazaspiro[4.5]decane-8-carboxylate (1.83 g, 7.20 mmol), commercially available 4-bromofuran-2(5H)-one (1.41 g, 8.63 mmol), Xantphos (0.416 g, 0.720 mmol), water (0.389 mL, 21.6 mmol), and potassium carbonate (1.989 g, 14.39 mmol) in toluene (50 mL) was degassed with nitrogen followed by addition of palladium acetate (0.081 g, 0.36 mmol). The resulting mixture was heated at 65° C. for 16 h. After filtration through CELITE®, the filtrate was concentrated and the residue was purified on silica gel column using EtOAc/hexane as eluting solvents to give the title compound. LC/MS: (M+1)⁺: 337.18.

Step B: 2-(5-oxo-2,5-dihydrofuran-3-yl)-2,8-diazaspiro[4.5]decan-1-one: To a solution of tert-butyl 1-oxo-2-(5-oxo-2,5-dihydrofuran-3-yl)-2,8-diazaspiro[4.5]decane-8-carboxylate (5.70 g, 16.9 mmol) in methylene chloride (10 mL) was added trifluoroacetic acid (26.1 mL, 339 mmol) and the resulting solution was stirred at rt for 1 h. After concentration the residue was basified on ion exchange column followed by washing with 1N ammonia in methanol solution to give 2-(5-oxo-2,5-dihydrofuran-3-yl)-2,8-diazaspiro[4.5]decan-1-one. LC/MS: (M+1)⁺: 237.06.

Intermediate 17

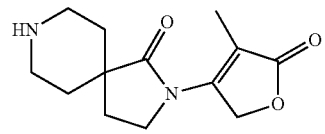

2-(4-Methyl-5-oxo-2,5-dihydrofuran-3-yl)-2,8-diazaspiro[4.5]decan-1-one

Step A: tert-Butyl 2-(4-methyl-5-oxo-2,5-dihydrofuran-3-yl)-1-oxo-2,8-diazaspiro[4.5]decane-8-carboxylate: To a mixture of tert-butyl 1-oxo-2,8-diazaspiro[4.5]decane-8-carboxylate (I-11, 80.0 g, 315 mmol) and 4-methyl-5-oxo-2,5-dihydrofuran-3-yltrifluoromethanesulfonate (I-9, 85.2 g, 346 mmol), Xantphos (13.6 g, 23.6 mmol), Cs₂CO₃ (153.7 g, 471.8 mmol) in toluene (1200 mL), was added Pd₂(dba)₃ (7.20 g, 7.86 mmol) under N₂. The resulting reaction mixture was heated to 90° C. and stirred under N₂ for 18 h. The mixture was filtered through a pad of CELITE® and the filtrate was concentrated. The residue was purified by precipitation to give tert-butyl 2-(4-methyl-5-oxo-2,5-dihydrofuran-3-yl)-1-oxo-2,8-diazaspiro[4.5]decane-8-carboxylate. ¹H NMR (400 MHz, CDCl₃) δ 5.23 (s, 2H), 4.02-3.99 (m, 4H), 3.06-3.05 (m, 2H), 2.15-2.11 (m, 2H), 2.02 (s, 3H), 1.87-1.81 (m, 2H), 1.51-1.41 (m, 11H)

Step B: 2-(4-Methyl-5-oxo-2,5-dihydrofuran-3-yl)-2,8-diazaspiro[4.5]decan-1-one: To a mixture of tert-butyl 2-(4-methyl-5-oxo-2,5-dihydrofuran-3-yl)-1-oxo-2,8-diazaspiro[4.5]decane-8-carboxylate (57.0 g, 163 mmol) in EtOAc (180 mL) was added saturated HCl (g)/EtOAc (712 mL) at 0° C. The resulting reaction mixture was stirred at room temperature for 3 h. The mixture was filtered and the filtrate was concentrated to give the HCl salt. To a mixture of HCl salt (54.2 g, 189 mmol) in MeOH (550 mL) was added NaHCO₃ (31.8 g, 378 mmol) at 0° C. The resulting reaction mixture was stirred at room temperature for 3 h until the pH=8. The mixture was filtered and the filtrate was concentrated. The residue was re-dissolved in MeOH and concentrated until a precipitate appeared. The mixture was filtered and the filtrate was concentrated to give 2-(4-methyl-5-oxo-2,5-dihydrofuran-3-yl)-2,8-diazaspiro[4.5]decan-1-one as a free amine. 1H NMR (400 MHz, CD3OD) δ 5.24 (s, 2H), 4.10-4.07 (m, 2H), 3.22-3.16 (m, 2H), 2.93-2.87 (m, 2H), 2.22-2.19 (m, 2H), 2.0 (s, 3H), 1.94-1.87 (m, 2H), 1.67-1.61 (m, 2H)

Intermediate 18

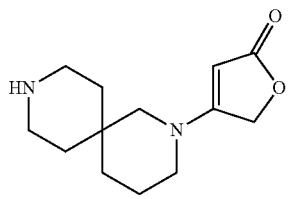 [SMILES: O=C1C=C(N2CCCC3(CCNCC3)C2)CO1]

2-(5-oxo-2,5-dihydrofuran-3-yl)-2,9-diazaspiro[5.5]undecan-1-one

Step A: tert-Butyl 1-oxo-2-(5-oxo-2,5-dihydrofuran-3-yl)-2,9-diazaspiro[5.5]undecane-9-carboxylate: A microwave vial was charged with commercially available tert-butyl 1-oxo-2,9-diazaspiro[5.5]undecane-9-carboxylate (Shanghai AQ BioPharma Co., Ltd, catalog #ABP3640, 100 mg, 0.373 mmol), 4-bromofuran-2(5H)-one (72.9 mg, 0.447 mmol), Pd$_2$(dba)$_3$ (17.06 mg, 0.019 mmol), Xantphos (32.3 mg, 0.056 mmol), and cesium carbonate (182 mg, 0.559 mmol). The vial was sealed, degassed, and filled with toluene (1.5 mL). The reaction mixture was heated at 90° C. overnight, and was filtered through CELITE®. The filtrate was evaporated to give the crude product, which was purified by column chromatograph (0-10% MeOH/DCM) to afford the title compound. LC/MS: [(M+1–56)]$^+$=295

Step B: 2-(5-oxo-2,5-dihydrofuran-3-yl)-2,9-diazaspiro[5.5]undecan-1-one: tert-Butyl 1-oxo-2-(5-oxo-2,5-dihydrofuran-3-yl)-2,9-diazaspiro[5.5]undecane-9-carboxylate (100 mg, 0.285 mmol) in DCM (2 mL) was treated with TFA (660 µL, 8.56 mmol) at 0° C. to give TFA salt. Then a 2 g Bond Elut SCX column was first rinsed with MeOH, the sample was loaded onto the column with MeOH, the cartridge was washed with MeOH drop-wise to remove TFA, and finally rinsed with 2N NH$_3$MeOH to provide the title compound as a free amine. LC/MS: [(M+1)]$^+$=251

Intermediate 19

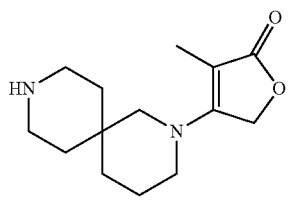 [SMILES: CC1=C(N2CCCC3(CCNCC3)C2)COC1=O]

2-(4-Methyl-5-oxo-2,5-dihydrofuran-3-yl)-2,9-diazaspiro[5.5]undecan-1-one

Step A: tert-Butyl 2-(4-methyl-5-oxo-2,5-dihydrofuran-3-yl)-1-oxo-2,9-diazaspiro[5.5]undecane-9-carboxylate: A microwave vial was charged with commercially available tert-butyl 1-oxo-2,9-diazaspiro[5.5]undecane-9-carboxylate (Shanghai AQ BioPharma Co., Ltd, catalog #ABP3640, 100 mg, 0.373 mmol), 4-methyl-5-oxo-2,5-dihydrofuran-3-yl trifluoromethanesulfonate (110 mg, 0.447 mmol), Pd$_2$(dba)$_3$ (17 mg, 0.019 mmol), Xantphos (32 mg, 0.056 mmol), and cesium carbonate (182 mg, 0.559 mmol). The vial was sealed, degassed, and filled with toluene (1.5 mL). The reaction mixture was heated at 90° C. overnight, and was filtered through CELITE®. The filtrate was evaporated to give the crude product, which was purified by column chromatography (0-10% MeOH/DCM) to afford the title compound. LC/MS: [(M+1–56)]$^+$=309

Step B: 2-(4-Methyl-5-oxo-2,5-dihydrofuran-3-yl)-2,9-diazaspiro[5.5]undecan-1-one: tert-Butyl 2-(4-methyl-5-oxo-2,5-dihydrofuran-3-yl)-1-oxo-2,9-diazaspiro[5.5]undecane-9-carboxylate (130 mg, 0.357 mmol) in DCM (2 mL) was treated with TFA (824 µL, 10.7 mmol) at 0° C. to give the TFA salt. Then a 2 g Bond Elut SCX (ion exchange cartridge) was first rinsed with MeOH, the sample was loaded onto the column with MeOH, the cartridge was washed with MeOH dropwise to remove TFA, and finally rinsed with 2N NH$_3$/MeOH to provide the title compound as a free amine. LC/MS: [(M+1)]$^+$=265

Intermediate 20

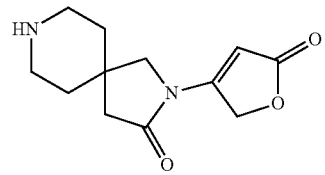

2-(5-oxo-2,5-dihydrofuran-3-yl)-2,8-diazaspiro[4.5]decan-3-one: The title compound was prepared from 3-oxo-2,8-diaza-spiro[4,5]decane-8-carboxylic acid tert-butyl ester and 4-bromofuran-2(5H)-one in two steps in an analogous fashion to that described for 2-(5-oxo-2,5-dihydrofuran-3-yl)-2,9-diazaspiro[5.5]undecan-1-one (I-18) above. LC/MS: [(M+1)]$^+$=237

Intermediate 21

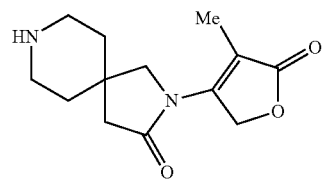

2-(5-oxo-2,5-dihydrofuran-3-yl)-2,8-diazaspiro[4.5]decan-3-one: The title compound was prepared from 3-oxo-2,8-diaza-spiro[4,5]decane-8-carboxylic acid tert-butyl ester and 4-methyl-5-oxo-2,5-dihydrofuran-3-yl trifluoromethanesulfonate in two steps in an analogous fashion to that described for 2-(4-Methyl-5-oxo-2,5-dihydrofuran-3-yl)-2,9-diazaspiro[5.5]undecan-1-one (I-19) above.

Intermediate 22

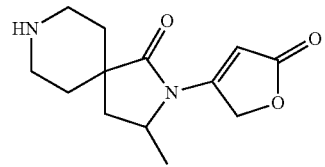

3-methyl-2-(5-oxo-2,5-dihydrofuran-3-yl)-2,8-diazaspiro[4.5]decan-1-one

Step A: tert-Butyl 3-methyl-1-oxo-2-(5-oxo-2,5-dihydrofuran-3-yl)-2,8-diazaspiro[4.5]decane-8-carboxylate: A mixture of tert-butyl 3-methyl-1-oxo-2,8-diazaspiro[4.5]decane-8-carboxylate (I-13) (505 mg, 1.88 mmol), 4,5-bis(diphenylphosphino)-9,9-dimethylxanthene (109 mg, 0.188 mmol), palladium(II) acetate (21 mg, 0.094 mmol), potassium carbonate (520 mg, 3.76 mmol), water (102 μl, 5.65 mmol) and commercially available 4-bromofuran-2-one (368 mg, 2.26 mmol) in toluene (13 mL) was degassed and then heated at 60° C. for 16 hours. The mixture was filtered through a pad of CELITE®, and the filter cake was washed with ethyl acetate. The filtrates were concentrated and the residue was purified by column chromatography eluting with 10-100% ethyl acetatehexane gradient to give the title compound. LC-MS (IE, m/z): 373.3 (M+23)$^+$.

Step B: 3-methyl-2-(5-oxo-2,5-dihydrofuran-3-yl)-2,8-diazaspiro[4.5]decan-1-one: tert-Butyl 3-methyl-1-oxo-2-(5-oxo-2,5-dihydrofuran-3-yl)-2,8-diazaspiro[4.5]decane-8-carboxylate (90 mg, 0.257 mmol) was dissolved in dichloromethane (2 mL) and treated with TFA (1 mL). After stirring at room temperature for 1.5 hours, the reaction mixture was concentrated to remove excess of the reagent and co-evaporated with dichloromethane three times to give the title compound. LC-MS (IE, m/z): 251 (M+1)$^+$.

Intermediate 22A

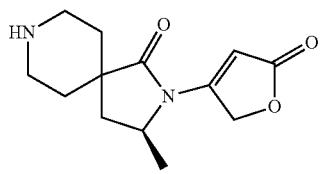

(S)-3-methyl-2-(5-oxo-2,5-dihydrofuran-3-yl)-2,8-diazaspiro[4.5]decan-1-one

The title compound was prepared in two steps from (S)-tert-Butyl 3-methyl-1-oxo-2,8-diazaspiro[4.5]decane-8-carboxylate in an analogous fashion to that described for the preparation of the racemate 3-methyl-2-(5-oxo-2,5-dihydrofuran-3-yl)-2,8-diazaspiro[4.5]decan-1-one (I-22) immediately above. LC-MS (IE, m/z): 251 (M+1)$^+$.

Intermediate 23

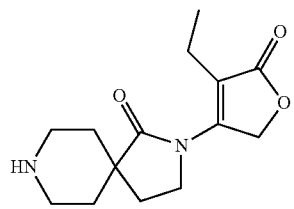 [SMILES: CCC1=C(N2CCC3(CCNCC3)C2=O)COC1=O]

2-(4-ethyl-5-oxo-2,5-dihydrofuran-3-yl)-2,8-diazaspiro[4.5]decan-1-one

Step A: ethyl 4-bromo-2-ethyl-3-oxobutanoate: To a solution of ethyl 2-ethyl-3-oxobutanoate (5.17 g, 32.7 mmol) in water (10 mL) at 0° C. was added bromine (1.684 mL, 32.7 mmol) dropwise over 2 h. The resulting solution was stirred at rt for 16 h. The mixture was extracted with ethyl acetate (100 mL) and the organic phase was dried over sodium sulfate and concentrated to give ethyl 4-bromo-2-ethyl-3-oxobutanoate. $^1$HNMR (500 MHz, CDCl$_3$), δ4.327-4.284(m, 2H), 2.412(s, 2H), 2.320-2.212 (q, 2H), 1.338-10309 (m, 3H), 1.042-1.013 (t, J=7.3 Hz, 3H).

Step B: 3-ethyl-4-hydroxyfuran-2(5H)-one: A mixture of ethyl 4-bromo-2-ethyl-3-oxobutanoate and hydrogen bromide (48%, 0.037 mL, 0.327 mmol) was heated at 100° C. for 20 h. After cooling to rt, the solid was collected by filtration followed by diethyl ether washing to give 3-ethyl-4-hydroxyfuran-2(5H)-one. LC/MS: (M+1)$^+$: 129.05.

Step C: 4-ethyl-5-oxo-2,5-dihydrofuran-3-yltrifluoromethanesulfonate: To a solution of 3-ethyl-4-hydroxyfuran-2(5H)-one (400 mg, 3.12 mmol) in dichloromethane (10 mL) at −78° C. was added 2,6-lutidine (0.545 mL, 4.68 mmol) and triflic anhydride (0.633 mL, 3.75 mmol) dropwise. The reaction solution was stirred at −78° C. for 1 h before being warmed to rt for 2 h. The mixture was diluted in dichloromethane (100 mL) and washed with 1 N hydrogen chloride (3×100 mL), sodium bicarbonate solution, dried over sodium sulfate and concentrated to give 4-ethyl-5-oxo-2,5-dihydrofuran-3-yl trifluoromethanesulfonate. LC/MS: (M+1)$^+$: 261.01.

Step D: tert-butyl 2-(4-ethyl-5-oxo-2,5-dihydrofuran-3-yl)-1-oxo-2,8-diazaspiro[4.5]decane-8-carboxylate: A mixture of tert-butyl 1-oxo-2,8-diazaspiro[4.5]decane-8-carboxylate (200 mg, 0.786 mmol), 4-ethyl-5-oxo-2,5-dihydrofuran-3-yltrifluoromethanesulfonate (246 mg, 0.944 mmol), Xantphos (45.5, 0.079 mmol), palladium (II) acetate (8.8 mg, 0.039 mmol), water (0.043 mL, 2.4 mmol), and potassium carbonate (217 mg, 1.57 mmol) in toluene (20 mL) was heated at 60° C. for 16 h. After filtration through CELITE®, the filtrate was concentrated and the residue was purified on silica gel using ethyl acetatehexane to give the title compound. LC/MS: (M+1)$^+$: 365.19.

Step E: 2-(4-ethyl-5-oxo-2,5-dihydrofuran-3-yl)-2,8-diazaspiro[4.5]decan-1-one: To a solution of tert-butyl 2-(4-ethyl-5-oxo-2,5-dihydrofuran-3-yl)-1-oxo-2,8-diazaspiro[4.5]decane-8-carboxylate (0.34 g, 0.93 mmol) in dichloromethane (1 mL) was added trifluoroacetic acid (2.16 mL, 28 mmol) and the resulting solution was stirred at rt for 1 h. After removing the volatiles, the residue was dissolved in dichloromethane (2 mL) and treated with hydrogen chloride (2 mL, 4 N in dioxane) and the mixture was concentrated to give 2-(4-ethyl-5-oxo-2,5-dihydrofuran-3-yl)-2,8-diazaspiro[4.5]decan-1-one. LC/MS: (M+1)$^+$: 265.16.

Intermediate 24

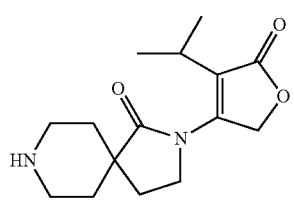

2-(4-isopropyl-5-oxo-2,5-dihydrofuran-3-yl)-2,8-diazaspiro[4.5]decan-1-one

Step A: ethyl 4-bromo-2-isopropyl-3-oxobutanoate: To a solution of ethyl 2-acetyl-3-methylbutanoate (5.10 g, 29.6 mmol) in water (10 mL) at 0° C. was added bromine (1.53 mL, 29.6 mmol) dropwise over 2 h. Chloroform (30 mL) was added and the resulting solution was stirred at rt for 16 h. Ethyl acetate (300 mL) was added to the reaction solution and the organic phase was dried over sodium sulfate and concentrated to give the title compound. $^1$HNMR (500 MHz, CDCl$_3$), δ4.300-4.282 (m, 2H), 2.601-2.575 (m, 1H), 2.406 (s, 2H), 1.331-1.303 (t, J=7.1 Hz, 3H), 1.085-1.072 (d, J=6.5 Hz, 3H), 1.048-1.035 (d, J=6.7 Hz, 3H).

Step B: 4-hydroxy-3-isopropylfuran-2(5H)-one: A mixture of ethyl 4-bromo-2-isopropyl-3-oxobutanoate (7.1 g, 28 mmol) and hydrogen bromide (48%, 0.032 mL, 0.28 mmol) was heated at 100° C. for 8 h. After cooling to rt, the solid was collected by filtration followed by diethyl ether washing to give 4-hydroxy-3-isopropylfuran-2(5H)-one. LCMS: (M+1)$^+$:143.09.

Step C: 4-isopropyl-5-oxo-2,5-dihydrofuran-3-yl trifluoromethanesulfonate: To a solution of 4-hydroxy-3-isopropylfuran-2(5H)-one (400 mg, 2.81 mmol) in methylene chloride (10 mL) at −78° C. was added 2,6-lutidine (0.492 mL, 4.22 mmol) and triflic anhydride (0.570 mL, 3.38 mmol) dropwise, and the reaction temperature was maintained at −78° C. for 1 h before warmed to rt for 2 h. The mixture was partitioned between methylene chloride and 1 N hydrogen chloride. The organic phase was washed with 1N hydrogen chloride then diluted sodium bicarbonate, dried over sodium sulfate and concentrated to give the title compound. LCMS: (M+1)$^+$: 275.07.

Step D: tert-butyl 2-(4-isopropyl-5-oxo-2,5-dihydrofuran-3-yl)-1-oxo-2,8-diazaspiro[4.5]decane-8-carboxylate: A mixture of tert-butyl 1-oxo-2,8-diazaspiro[4.5]decane-8-carboxylate (I-11) (200 mg, 0.786 mmol), 4-isopropyl-5-oxo-2,5-dihydrofuran-3-yl trifluoromethanesulfonate (259 mg, 0.944 mmol), Xantphos (46 mg, 0.079 mmol), palladium (II) acetate (8.8 mg, 0.039 mmol), water (0.043 mL, 2.4 mmol), and potassium carbonate (217 mg, 1.57 mmol) in toluene (20 mL) was heated at 66° C. for 16 h. After filtration through CELITE®, the filtrate was concentrated and the residue was purified on a silica gel column to give the title compound. LC/MS: (M+1)$^+$: 379.21.

Step E: 2-(4-isopropyl-5-oxo-2,5-dihydrofuran-3-yl)-2,8-diazaspiro[4.5]decan-1-one: To a solution of tert-butyl 2-(4-isopropyl-5-oxo-2,5-dihydrofuran-3-yl)-1-oxo-2,8-diazaspiro[4.5]decane-8-carboxylate (195 mg, 0.515 mmol) in methylene chloride was added trifluoroacetic acid at rt and the resulting solution was stirred at rt for 1 h. After removing the volatiles the residue was dissolved in methylene chloride and treated with hydrogen chloride (2 mL, 4 N in dioxane) and concentrated again to give 2-(4-isopropyl-5-oxo-2,5-dihydrofuran-3-yl)-2,8-diazaspiro[4.5]decan-1-one as hydrogen chloride salt. LCMS: (M+1)$^+$: 279.16.

Intermediate 25

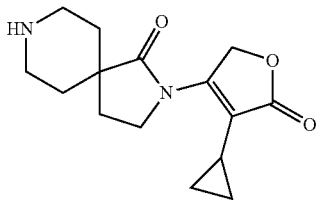 [SMILES: O=C1OCC(N2CCC3(CCNCC3)C2=O)=C1C1CC1]

2-(4-cyclopropyl-5-oxo-2,5-dihydrofuran-3-yl)-2,8-diazaspiro[4.5]decan-1-one

Step A: tert-Butyl 2-(4-bromo-5-oxo-2,5-dihydrofuran-3-yl)-1-oxo-2,8-diazaspiro[4.5]decane-8-carboxylate: tert-Butyl 1-oxo-2-(5-oxo-2,5-dihydrofuran-3-yl)-2,8-diazaspiro[4.5]decane-8-carboxylate (I-16, Step A) (784 mg, 2.33 mmol) was dissolved in DCM (20 mL) and was treated with NBS (498 mg, 2.80 mmol) at 25° C. for 12 hours. The reaction mixture was diluted with DCM (20 mL), washed with water (20 mL) and brine (20 mL), dried over anhydrous sodium sulfate and filtered. The filtrates were concentrated and the crude product was purified by column chromatography (ISCO 40 g silica gel column), eluting with 50-100% ethyl acetatehexane gradient to give the title compound.

Step B: tert-Butyl 2-(4-cyclopropyl-5-oxo-2,5-dihydrofuran-3-yl)-1-oxo-2,8-diazaspiro[4.5]decane-8-carboxylate:
In a microwave vial, tert-butyl 2-(4-bromo-5-oxo-2,5-dihydrofuran-3-yl)-1-oxo-2,8-diazaspiro[4.5]decane-8-carboxylate (90 mg, 0.22 mmol) was dissolved in toluene (2 mL) and water (0.2 mL). Potassium phosphate (138 mg, 0.650 mmol), tricyclohexylphosphine (18 mg, 0.065 mmol), cyclopropylboronic acid (74.5 mg, 0.867 mmol) and palladium acetate (4.87 mg, 0.022 mmol) were added. The reaction mixture was de-gassed and heated at 100° C. for 12 hours. After cooling to room temperature, the reaction mixture was concentrated and the resulting residue was dissolved in EtOAc (50 mL), washed with water (30 mL) and brine (30 mL), dried over sodium sulfate, and filtered. Removing the solvent gave crude product that was purified by column chromatography eluting with 0-100% EtOAc/hexane gradient to yield the title compound. $^1$H NMR (500 MHz, CDCl$_3$) δ 5.20 (s, 2H), 4.22 (m, 2H), 3.99 (m, 2H), 3.05 (m, 2H), 2.09 (m, 2H), 1.92 (m, 2H), 1.60 (m, 2H), 1.56 (m, 10H), 1.02 (m, 2H), 0.82 (m, 2H).

Step C: 2-(4-cyclopropyl-5-oxo-2,5-dihydrofuran-3-yl)-2,8-diazaspiro[4.5]decan-1-one: The title compound can be prepared in a similar fashion to that described for 2-(4-isopropyl-5-oxo-2,5-dihydrofuran-3-yl)-2,8-diazaspiro[4.5]decan-1-one (I-24) above using TFA.

Intermediate 26

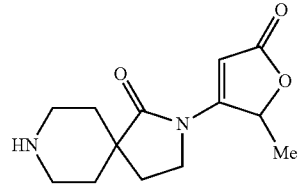 [SMILES: CC1OC(=O)C=C1N1CCC2(CCNCC2)C1=O]

2-(2-methyl-5-oxo-2,5-dihydrofuran-3-yl)-2,8-diazaspiro[4.5]decan-1-one

Step A: ethyl 4-bromo-3-oxopentanoate: To a solution of ethyl 3-oxopentanoate (5.00 g, 34.7 mmol) in chloroform (27 mL) at 0° C. was added bromine (1.79 mL, 34.7 mmol) in chloroform (10 mL) drop-wise. The resulting solution was stirred at rt for 16 h. The solution was washed with water, dried over sodium sulfate, concentrated to give ethyl 4-bromo-3-oxopentanoate. $^1$HNMR (500 MHz, CDCl$_3$), δ4.670-4.630 (dd, J=6.7 Hz, 1H), 4.251-4.208(dd, J=7.2 Hz, 2H), 3.883-3.851(d, J=16 Hz, 1H), 3.687-3.655(d, J=16 Hz, 1H), 1.804-1.791 (d, J=6.8 Hz, 3H), 1.323-1.295 (m, J=7.2 Hz, 3H).

Step B: 4-hydroxy-5-methylfuran-2(5H)-one: Ethyl 4-bromo-3-oxopentanoate (7.49 g, 33.6 mmol) was treated with potassium hydroxide (5.03 g, 90 mmol) in water (36 mL) at 0° C. The resulting mixture was vigorously stirred at 0° C. for 4 h. The reaction mixture was extracted with methylene chloride (twice with 100 mL). The alkaline phase was acidified to pH<1 by 6N hydrogen chloride. The acidic phase was extracted with methylene chloride (3×100 mL). The latter combined organic phase was dried over sodium sulfate and concentrated to give the title compound. $^1$HNMR (500 MHz, CDCl$_3$), δ5.064 (s, 1H), 4.949-4.878(m, 1H), 3.251-3.239 (m, 1H), 1.566-1.547 (m, 3H).

Step C: 2-methyl-5-oxo-2,5-dihydrofuran-3-yltrifluoromethanesulfonate: To a solution of 4-hydroxy-5-methylfuran-2(5H)-one in methylene chloride (10 mL) at −78° C. was added 2,6-lutidine (0.612 mL, 5.26 mmol) and triflic anhydride (0.711 mL, 4.21 mmol) drop-wise. The reaction temperature was maintained at −78° C. for 0.5 h before being warmed to rt for 1 h. The mixture was washed with hydrogen chloride (1N, three times 100 mL), diluted sodium bicarbonate and dried over sodium sulfate to give the title compound. LC/MS: $(M+1)^+$: 247.00.

Step D: tert-butyl 2-(2-methyl-5-oxo-2,5-dihydrofuran-3-yl)-1-oxo-2,8-diazaspiro[4.5]decane-8-carboxylate: A mixture of tert-butyl 1-oxo-2,8-diazaspiro[4.5]decane-8-carboxylate (200 mg, 0.786 mmol), 2-methyl-5-oxo-2,5-dihydrofuran-3-yltrifluoromethanesulfonate (232 mg, 0.944 mmol), Xantphos (45.5 mg, 0.079 mmol), palladium (II) acetate (8.83 mg, 0.039 mmol), water (0.043 mL, 2.359 mmol), and potassium carbonate (217 mg, 1.573 mmol) in toluene (20 mL) was degassed by nitrogen and heated at 65° C. for 16 h. After filtration through CELITE® the filtrate was concentrated and the residue was purified on silica gel column using ethyl acetate and hexane as eluting solvents to give the title compound. LCMS: $(M+1)^+$: 351.15.

Step E: 2-(2-methyl-5-oxo-2,5-dihydrofuran-3-yl)-2,8-diazaspiro[4.5]decan-1-one: To a solution of tert-butyl 2-(2-methyl-5-oxo-2,5-dihydrofuran-3-yl)-1-oxo-2,8-diazaspiro [4.5]decane-8-carboxylate (127 mg, 0.362 mmol) in methylene chloride (1 mL) was added trifluoroacetic acid (1.396 mL, 18.12 mmol), the resulting solution was stirred at rt for 1 h. After concentration, the residue was treated with methylene chloride (1 mL) and hydrogen chloride (1 mL, 4 N in dioxane). The resulting mixture was concentrated to give the title compound as hydrogen chloride salt. LC/MS: $(M+1)^+$: 251.19.

Intermediate 27

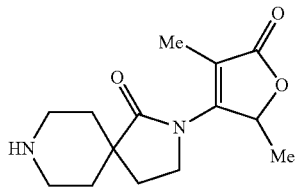 [SMILES: CC1=C(N2CCC3(CCNCC3)C2=O)C(C)OC1=O]

2-(2,4-dimethyl-5-oxo-2,5-dihydrofuran-3-yl)-2,8-diazaspiro[4.5]decan-1-one

Step A: ethyl 4-bromo-2-methyl-3-oxopentanoate: To a solution of ethyl 2-methyl-3-oxopentanoate (5.0 g, 34.7 mmol) in chloroform at 0° C. was added bromine (1.79 mL, 34.7 mmol) in chloroform (10 mL) drop-wise. The resulting solution was stirred at rt for 16 h. The solution was washed with water, dried over sodium sulfate, and concentrated to give the title compound. $^1$HNMR (500 MHz, CDCl$_3$), δ4.781-4.740 (dd, J=6.6 Hz, 1H), 4.140-4.098(dd, J=7.0 Hz, 1H), 3.770 (s, 3H), 1.797-1.783(d, J=6.6 Hz, 3H), 1.455-1.442 (d, J=7.0 Hz, 3H).

Step B: 4-hydroxy-3,5-dimethylfuran-2(5H)-one: To ethyl 4-bromo-2-methyl-3-oxopentanoate (7.49 g, 31.6 mmol) was added cold potassium hydroxide (4.7 g, 84 mmol) in water (36 mL) at 0° C., the resulting mixture was vigorously stirred at 0° C. for 4 h. The reaction mixture was extracted with methylene chloride (2×100 mL), the alkaline phase was acidified to ph 1 by 6N hydrogen chloride followed by extraction with methylene chloride (3 times 100 mL). The combined latter organic phase was dried over sodium sulfate, and concentrated to give 4-hydroxy-3,5-dimethylfuran-2(5H)-one. LCMS: $(M+23)^+$: 151.10, $^1$HNMR (500 MHz, CDCl$_3$), δ4.882-4.842 (dd, J=6.8 Hz, 1H), 3.744 (s, 1H), 1.759(s, 3H). 1.526-1.513 (d, J=6.8 Hz, 3H).

Step C: 2,4-dimethyl-5-oxo-2,5-dihydrofuran-3-yl trifluoromethanesulfonate: To a solution of 4-hydroxy-3,5-dimethylfuran-2(5H)-one (400 mg, 3.12 mmol) in methylene chloride (10 mL) at −78° C. was added 2,6-lutidine (0.545 mL, 4.68 mmol) and triflic anhydride (0.633 mL, 3.75 mmol) drop-wise. The reaction temperature was maintained at −78° C. for 1 h before warming to rt for 2 h. The mixture was diluted in methylene chloride (100 mL) and washed with 1N hydrogen chloride (3×100 mL) and diluted sodium bicarbonate, then dried over sodium sulfate and concentrated to give the title compound. LCMS: $(M+1)^+$: 261.00.

Step D: tert-butyl 2-(2,4-dimethyl-5-oxo-2,5-dihydrofuran-3-yl)-1-oxo-2,8-diazaspiro[4.5]decane-8-carboxylate: A mixture of tert-butyl 1-oxo-2,8-diazaspiro[4.5]decane-8-carboxylate (200 mg, 0.786 mmol), 2,4-dimethyl-5-oxo-2,5-dihydrofuran-3-yl trifluoromethanesulfonate, Xantphos (45.5 mg, 0.079 mmol), water (0.043 mL, 2.4 mmol) and potassium carbonate (217 mg, 1.57 mmol) in toluene (20 mL) was degassed by nitrogen for 20 min followed by addition of palladium acetate (8.8 mg, 0.039 mmol). The resulting mixture was heated at 65° C. for 16 h. After filtration the filtrate was concentrated and the residue was purified on silica gel column eluting with EtOAc/hexane to give the title compound. LC/MS: $(M+1)^+$: 365.20.

Step E: 2-(2,4-dimethyl-5-oxo-2,5-dihydrofuran-3-yl)-2,8-diazaspiro[4.5]decan-1-one: To a solution of tert-butyl 2-(2,4-dimethyl-5-oxo-2,5-dihydrofuran-3-yl)-1-oxo-2,8-diazaspiro[4.5]decane-8-carboxylate (195 mg, 0.535 mmol) in methylene chloride (1 mL) was added trifluoroacetic acid (2.06 mL, 26.8 mmol) and the resulting solution was stirred at rt for 1 h. After removing the volatiles the residue was dissolved in methylene chloride (1 mL) and treated with hydrogen chloride (4 mL, 1N in diethyl ether) and concentrated to give 2-(2,4-dimethyl-5-oxo-2,5-dihydrofuran-3-yl)-2,8-diazaspiro[4.5]decan-1-one. LCMS: $(M+1)^+$: 265.19.

Intermediate 28

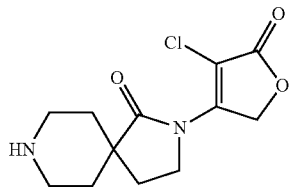 [SMILES: O=C1OCC(N2CCC3(CCNCC3)C2=O)=C1Cl]

2-(4-chloro-5-oxo-2,5-dihydrofuran-3-yl)-2,8-diazaspiro[4.5]decan-1-one

Step A: tert-butyl 2-(4-chloro-5-oxo-2,5-dihydrofuran-3-yl)-1-oxo-2,8-diazaspiro[4.5]decane-8-carboxylate: To a solution of tert-butyl 1-oxo-2-(5-oxo-2,5-dihydrofuran-3-yl)-2,8-diazaspiro[4.5]decane-8-carboxylate (I-16, Step A) (2.1 g, 6.2 mmol) in chloroform (50 mL) was added NCS (1.00 g, 7.49 mmol) at rt and the resulting solution was heated at 60° C. overnight. After removing the volatiles the residue was purified on silica gel column using EtOAc/hexane as eluting solvents to give the title compound. LCMS: (M+1)⁺: 371.11, 372.99.

Step B: 2-(4-chloro-5-oxo-2,5-dihydrofuran-3-yl)-2,8-diazaspiro[4.5]decan-1-one: To a solution of tert-butyl 2-(4-chloro-5-oxo-2,5-dihydrofuran-3-yl)-1-oxo-2,8-diazaspiro[4.5]decane-8-carboxylate (2.26 g, 6.09 mmol) in methylene chloride (10 mL) was added trifluoroacetic acid (9.39 mL, 122 mmol) and the resulting solution was stirred at rt for 1 h. After removing the volatiles, the residue was partitioned between methylene chloride (100 mL) and 1N sodium hydroxide (100 mL). The alkaline phase was extracted with methylene chloride (2×100 mL). The combined organic phase was dried over sodium sulfate and concentrated to give 2-(4-chloro-5-oxo-2,5-dihydrofuran-3-yl)-2,8-diazaspiro[4.5]decan-1-one. LCMS: (M+1)⁺: 271.07, 272.96.

Intermediate 29

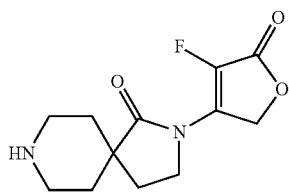

2-(4-fluoro-5-oxo-2,5-dihydrofuran-3-yl)-2,8-diazaspiro[4.5]decan-1-one

Step A: 3-bromo-4-ethoxy-3-fluoro-4-hydroxydihydrofuran-2(3H)-one: To a solution of 4-hydroxyfuran-2(5H)-one (2.25 g, 22.5 mmol) in ethanol (20 mL) was added NBS (4.00 g, 22.5 mmol), and the resulting solution was stirred at rt for 40 min. Then 1-chloromethyl-4-fluoro-1,4-diazoniabicyclo[2.2.2]octane bis(tetrafluoroborate) (7.97 g, 22.5 mmol) was added and the resulting mixture was stirred at rt overnight. After filtration and concentration, the residue was purified on silica gel column using EtOAc/hexane as eluting solvents to afford the title compound. ¹HNMR (500 MHz, CDCl₃), δ4.322-4.303 (m, J=7.0 Hz, 2H), 3.879-3.788 (m, 2H), 1.356-1.328 (t, J=7.0 Hz, 3H).

Step B: 3-fluoro-4-hydroxyfuran-2(5H)-one: To a solution of 3-bromo-4-ethoxy-3-fluoro-4-hydroxydihydrofuran-2(3H)-one (4.39 g, 18.1 mmol) in tetrahydrofuran (20 mL) was added tri-n-butyltin hydride (9.39 mL, 35.0 mmol) at 0° C. under N₂. The resulting solution was stirred at rt overnight. After removing the volatiles, the residue was stirred in 30 mL 50% acetic acid and 30 mL hexane at rt for 30 min. The acidic phase was washed with hexane (3×30 mL) before concentration. The reside was dissolved in sodium carbonate (50 mL, 2N), extracted with 40% EtOAc/hexane (4×50 mL), the alkaline phase was acidified to pH <1 by 1 N hydrogen chloride. The acidic phase was then extracted with ethyl acetate (8 times 60 mL). The combined organic phase was dried over sodium sulfate, concentrated to give 3-fluoro-4-hydroxyfuran-2(5H)-one. ¹HNMR (500 MHz, DMSO-d₆), δ4.694-4.687 (d, J=3.9 Hz, 2H).

Step C: 4-fluoro-2-methyl-5-oxo-2,5-dihydrofuran-3-yl-trifluoromethanesulfonate: To a solution of 3-fluoro-4-hydroxyfuran-2(5H)-one (400 mg, 3.39 mmol) in methylene chloride (10 mL) at −78° C. was added 2,6-lutidine (0.592 mL, 5.08 mmol) and triflic anhydride (0.687 mL, 4.07 mmol) drop-wise, the reaction temperature was maintained at −78° C. for 1 h before warmed to rt for 2 h. The mixture was washed with 1 N hydrogen chloride (3 times 100 mL), and diluted sodium bicarbonate solution, dried over sodium sulfate, concentrated to give the title compound. ¹HNMR (500 MHz, CDCl₃), δ4.986-4.974(d, J=6.0 Hz, 2H).

Step D: tert-butyl 2-(4-fluoro-5-oxo-2,5-dihydrofuran-3-yl)-1-oxo-2,8-diazaspiro[4.5]decane-8-carboxylate: A mixture of tert-butyl 1-oxo-2,8-diazaspiro[4.5]decane-8-carboxylate (150 mg, 0.590 mmol), 4-fluoro-2-methyl-5-oxo-2,5-dihydrofuran-3-yl trifluoromethanesulfonate (148 mg, 0.590 mmol), xantphos (34.1 mg, 0.059 mmol), water (0.032 mL, 1.77 mmol) in toluene (20 mL) was degassed by nitrogen followed by addition of palladium acetate (6.6 mg, 0.029 mmol). The resulting mixture was heated at 65° C. overnight. After filtration through CELITE®, the filtrate was concentrated and the residue was purified on silica gel column using ethyl acetate and hexane as eluting solvents to give the title compound. LCMS: (M+1)⁺: 355.15.

Step E: 2-(4-fluoro-5-oxo-2,5-dihydrofuran-3-yl)-2,8-diazaspiro[4.5]decan-1-one: To a solution of tert-butyl 2-(4-fluoro-5-oxo-2,5-dihydrofuran-3-yl)-1-oxo-2,8-diazaspiro[4.5]decane-8-carboxylate (109 mg, 0.308 mmol) in methylene chloride (1 mL) was added trifluoroacetic acid (1.896 mL, 24.61 mmol) and the resulting solution was stirred at rt for 1 h. After removing the volatiles, the residue was dissolved in methanol and loaded onto an ion exchange column. After washing with methanol, the product was eluted with 2N ammonia in methanol solution which was concentrated to give the title compound. LC/MS: (M+1)⁺: 255.09.

Intermediate 30

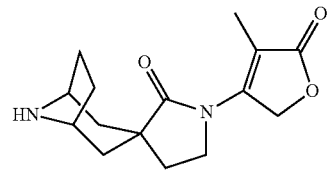 [SMILES: CC1=C(N2CCC3(CC4CCC(C3)N4)C2=O)COC1=O]

(1R,3r,5S)-1'-(4-methyl-5-oxo-2,5-dihydrofuran-3-yl)-8-azaspiro[bicyclo[3.2.1]octane-3,3'-pyrrolidin]-2'-one Step A: (1R,3s,5S)-8-tert-butyl 3-methyl 8-azabicyclo[3.2.1]octane-3,8-dicarboxylate: To a solution of (1R,3s,5S)-8-(tert-butoxycarbonyl)-8-azabicyclo[3.2.1]octane-3-carboxylic acid (5.00 g, 19.6 mmol) in a mixture solvent of dry MeOH (60 mL) and DCM (60.0 mL) was added (trimethylsilyl)diazomethane (19.6 mL, 39.2 mmol). The mixture was stirred for 0.5 hr. AcOH (5 mL) was added. The volatiles were removed under reduced pressure. The residue was dissolved in EtOAc, and the solution was washed with saturated NaHCO₃ and brine, and dried over MgSO4. The solvent was removed to give a solid which was used in the next step without further purification. LC-MS: 214.10 (M+1−56).

Step B: (1R,3r,5S)-8-tert-butyl 3-methyl 3-(cyanomethyl)-8-azabicyclo[3.2.1]octane-3,8-dicarboxylate: To a solution of (1R,3r,5S)-8-tert-butyl 3-methyl 8-azabicyclo[3.2.1]octane-3,8-dicarboxylate (5.00 g, 18.6 mmol) in THF (100 mL) was added LDA (13.9 mL, 27.8 mmol) at −78° C. The mixture was stirred at the same temperature for 30 min, then bromoacetonitrile (1.94 mL, 27.8 mmol) in THF (15 mL) was added by injection. The mixture was stirred at −78° C. for 15 min, quenched with saturated KHSO₄ at −78° C., warmed up to rt and diluted with ether (100 mL). The organic layer was separated, and the aqueous was extracted with ether (50 mL). The combined organic layers were washed with brine, dried (MgSO₄), and concentrated. The residue was purified by column (silica gel 120 g, EtOAc-Hexane-0-50% gradient, then 50% EtOAc. ¹H-NMR (500 MHz, CDCl₃): δ ppm 4.18 (1 H, m), 4.27 (1 H, m), 3.83 (3 H, s), 2.58 (2 H, m), 2.43 (2 H, m), 1.55-1.95 (6 H, m), 1.50 (9 H, s). LC-MS 209.23 (M+1−100).

Step C: (1R,3r,5S)-8-tert-butyl 3-methyl 3-(2-aminoethyl)-8-azabicyclo[3.2.1]octane-3,8-dicarboxylate: To a solution of (1R,3r,5S)-8-tert-butyl 3-methyl 3-(cyanomethyl)-8-azabicyclo[3.2.1]octane-3,8-dicarboxylate (4.0 g, 12.97 mmol) in ethanol (20 mL) and AcOH (20 mL) was added platinum(IV) oxide (0.295 g, 1.30 mmol). The mixture was hydrogenated on a shaker (45 psi hydrogen) for 24 hr. The catalyst was filtered off through a CELITE® pad, and the filtrate was concentrated. The crude material was used in the next step without further purification. LC-MS: 313.20 (M+1), 257.18 (M+1−56).

Step D: (1R,3r,5S)-tert-butyl 2'-oxo-8-azaspiro[bicyclo [3.2.1]octane-3,3'-pyrrolidine]-8-carboxylate: A mixture of (1R,3r,5S)-8-tert-butyl 3-methyl 3-(2-aminoethyl)-8-azabicyclo[3.2.1]octane-3,8-dicarboxylate (4.2 g, 13.4 mmol) and potassium carbonate (9.29 g, 67.2 mmol) in MeOH (50 mL) was heated at 60° C. for 1 hr. The mixture was concentrated, and DCM (50 mL) was added. The suspension was filtered through a silica gel pad. The filtrate was concentrated to give a solid which was directly used in the next step ¹H-NMR (500 MHz, CDCl₃): δ ppm 5.95 (1 H, bs), 4.30 (1 H, m), 4.20 (1 H, m), 3.26 (2 H, t, J=7.0 Hz), 1.75-2.15 (6 H, m), 1.47 (9 H, s). LCMS: 281.15 (+1), 225.14 (M+1−56).

Step E: (1R,3r,5S)-tert-butyl 1'-(4-methyl-5-oxo-2,5-dihydrofuran-3-yl)-2'-oxo-8-azaspiro[bicyclo[3.2.1]octane-3,3'-pyrrolidine]-8-carboxylate: A mixture of 4-methyl-5-oxo-2,5-dihydrofuran-3-yltrifluoromethanesulfonate (1.861 g, 7.56 mmol), (1R,3r,5S)-tert-butyl 2'-oxo-8-azaspiro[bicyclo [3.2.1]octane-3,3'-pyrrolidine]-8-carboxylate (1.63 g, 5.81 mmol), palladium(II) acetate (0.065 g, 0.291 mmol), 4,5-bis (diphenylphosphino)-9,9-dimethylxanthene (0.336 g, 0.581 mmol), potassium carbonate (2.411 g, 17.44 mmol) and water (0.314 mL, 17.4 mmol) in toluene (150 mL) was heated at 60° C. under N₂ overnight. The mixture was diluted with EtOAc. Solid was filtered off through a CELITE® pad, and the filtrate was concentrated. The residue was purified by column (80 g silica gel, 0-100% of EtOAc in hexane, then 100% EtOAc). LCMS: 377.12 (M+1).

Step F: (1R,3r,5S)-1'-(4-methyl-5-oxo-2,5-dihydrofuran-3-yl)-8-azaspiro[bicyclo[3.2.1]octane-3,3'-pyrrolidin]-2'-one: A solution of (1R,3r,5S)-tert-butyl 1'-(4-methyl-5-oxo-2,5-dihydrofuran-3-yl)-2'-oxo-8-azaspiro[bicyclo[3.2.1] octane-3,3'-pyrrolidine]-8-carboxylate in DCM (50 mL) and TFA (10 mL) was stirred at rt for 1 h. Volatiles were removed under reduced pressure. The residue was dissolved in methanol, and was loaded on a Bond Elut SCX column after the column was washed with 20 mL methanol. The column with the desired compound was eluted with methanol to remove TFA (~20 mL), and the free base of the desired compound was eluted out with 2N NH₃ in methanol (~20 mL). The solution was concentrated to give a free base (solid). ¹H-NMR (500 MHz, CDCl₃): δ ppm 5.25 (2 H, s), 3.95 (2 H, t, J=6.9 Hz), 3.73 (2 H, m), 2.15 (4 H, m), 2.07 (3 H, s), 2.05 (4 H, m), 1.85 (2 H, m). LCMS 277.10 (M+1).

Intermediate 31

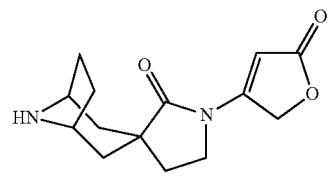 [SMILES: O=C1C=C(N2CCC3(CC4CCC(C3)N4)C2=O)CO1]

(1R,3r,5S)-1'-(5-oxo-2,5-dihydrofuran-3-yl)-8-azaspiro [bicyclo[3.2.1]octane-3,3'-pyrrolidin]-2'-one: The title compound was prepared in an analogous fashion to that described for (1R,3r,5S)-1'-(4-methyl-5-oxo-2,5-dihydrofuran-3-yl)-8-azaspiro[bicyclo[3.2.1]octane-3,3'-pyrrolidin]-2'-one, except in Step E, where 4-bromofuran-2-one was used in place of 4-methyl-5-oxo-2,5-dihydrofuran-3-yl trifluoromethanesulfonate. LCMS: 263 (M+1).

Intermediate 32

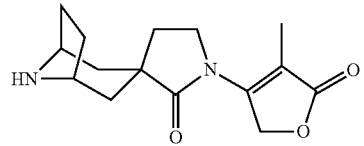

(1R,3s,5S)-1'-(4-methyl-5-oxo-2,5-dihydrofuran-3-yl)-8-azaspiro[bicyclo[3.2.1]octane-3,3'-pyrrolidin]-2'-one Step A: (1R,5S,Z)-tert-butyl 3-(1-cyano-2-methoxy-2-oxoethylidene)-8-azabicyclo[3.2.1]octane-8-carboxylate: Methyl 2-cyanoacetate (3.63 g, 36.6 mmol), commercially available (1R,5S)-tert-butyl 3-oxo-8-azabicyclo[3.2.1]octane-8-carboxylate (5.5 g, 24.41 mmol), ammonium acetate (2.51 mL, 36.6 mmol), acetic acid (5.59 mL, 98 mmol) and toluene (100 mL) were placed in a 500-mL round-bottomed flask attached to a Dean-Stark constant water separator which was connected to a reflux condenser. The flask was heated in an oil bath at 150° C., and the water that distilled out of the mixture with the refluxing toluene was removed from the separator at intervals (overnight). Solvent was removed under reduced pressure. The residue was dissolved in EtOAc (150 mL). The solution was washed with brine, dried (MgSO₄), and concentrated. The residue was purified by column chromatography on silica gel (hexane in EtOAc 0-60% gradient). ¹H-NMR (500 MHz, CDCl₃): δ ppm 4.40 (2 H, m), 3.86 (3 H, m), 2.75 (2 H, m), 2.55 (2 H, m), 2.06 (2 H, m), 1.57 (2 H, m), 1.50 (9 H, s). LC-MS-250.99.12 (M+1−56).

Step B: (1R,3r,5S)-tert-butyl 3-(1-cyano-2-methoxy-2-oxoethyl)-3-vinyl-8-azabicyclo-[3.2.1]octane-8-carboxylate: To a suspension of (1R,5S,Z)-tert-butyl 3-(1-cyano-2- methoxy-2-oxoethylidene)-8-azabicyclo[3.2.1]octane-8-carboxylate (7.17 g, 23.4 mmol) and copper(I) iodide (2.229 g, 11.70 mmol) in THF (150 mL) was added vinylmagnesium bromide (35.1 mL, 35.1 mmol) by injection at −10° C. The mixture was stirred at the same temperature for 1 h. The reaction was quenched with saturated ammonium acetate aqueous, and the mixture was diluted with EtOAc (100 mL). The organic layer was separated, and the aqueous layer was extracted with EtOAc (100 mL). The combined organic layers were washed with brine, dried over $MgSO_4$ and concentrated. The crude material was purified by column chromatography on silica gel (eluted with 0-50% EtOAc, then 50% EtOAc in hexane). $^1$H-NMR (500 MHz, $CDCl_3$): δ ppm 5.82 (1 H, dd, $J_1$=17.3 Hz, $J_2$=10.7 Hz), 5.15 (1 H, d, J=10.7 Hz), 5.10 (1 H, d, J=17.3 Hz), 4.20-4.50 (2 H, m), 3.85 (1 H, s), 3.81 (3 H, s), 2.17-2.35 (2 H, m), 1.90-2.15 (4 H, m), 1.58-1.72 (2 H, m) m 1.47 (9 H, s). LC-MS: 278.92 (M+1−56).

Step C: (1R,3s,5S)-tert-butyl 3-(cyanomethyl)-3-vinyl-8-azabicyclo[3.2.1]octane-8-carboxylate: A suspension of (1R,3r,5S)-tert-butyl 3-(1-cyano-2-methoxy-2-oxoethyl)-3-vinyl-8-azabicyclo[3.2.1]octane-8-carboxylate (7.2 g, 21.53 mmol) and sodium chloride (1.258 g, 21.53 mmol) in DMSO (40 mL) and water (4 mL) was heated in an 160° C. oil bath for 2 h, then cooled down to RT. Water (50 mL) was added, and the mixture was extracted with ethyl ether (twice with 50 mL). The combined ether layers were washed with brine, dried over $MgSO_4$, and concentrated under reduced pressure. The crude material was purified by column chromatography (0-70% ethyl acetate in hexane). $^1$H-NMR (500 MHz, $CDCl_3$): δ ppm 5.73 (1 H, dd, J1=17.7 Hz, J2=11.0 Hz), 5.10 (1 H, d, J=11 HZ), 5.08 (1 H, d, J=17.7 Hz), 5.30 (2 H, m), 2.70 (2 H, s), 1.95-2.12 (4 H, m), 1.70 (4 H, m), 1.45 (9 H, s). LC-MS: 221.11 (M+1−56).

Step D: (1R,3s,5S)-tert-butyl 3-(cyanomethyl)-3-formyl-8-azabicyclo[3.2.1]octane-8-carboxylate: To a suspension of (1R,3s,5S)-tert-butyl 3-(cyanomethyl)-3-vinyl-8-azabicyclo[3.2.1]octane-8-carboxylate (4.00 g, 14.5 mmol, water (15 mL) and sodium periodate (12.4 g, 57.9 mmol) in dioxane (45 mL) was added osmium tetroxide (0.184 g, 0.724 mmol). The suspension was stirred for 17 hr at rt. The mixture was made acidic with 1N hydrochloric acid, diluted with EtOAc (50 mL). The organic layer was separated, washed with brine, dried over $MgSO_4$, and concentrated under reduced pressure. The residue was used without further purification. $^1$H-NMR (500 MHz, $CDCl_3$): δ ppm 9.14 (1 H, s), 4.17 (2 H, m), 3.80 (3 H, s), 2.32 (2 H, m), 2.15 (2 H, m), 1.73 (2 H, m), 1.55 (2 H, m). LC-MS-223.16 (M+1−56).

Step E: (1R,3 s,5S)-8-(tert-butoxycarbonyl)-3-(cyanomethyl)-8-azabicyclo[3.2.1]octane-3-carboxylic acid: To a solution of (1R,3s,5S)-tert-butyl 3-(cyanomethyl)-3-formyl-8-azabicyclo[3.2.1]octane-8-carboxylate (5.10 g, 18.3 mmol) in t-BuOH/$H_2O$ (2:1) was added sodium dihydrogenphosphate hydrate (7.59 g, 55.0 mmol) and 2-methylbut-2-ene (9.7 mL, 92 mmol). The suspension was cooled to 0° C., and sodium chlorite (4.97 g, 55.0 mmol) was added portionwise. The reaction mixture was stirred at 0° C. for 1 h, acidified with 1M HCl, extracted with $CHCl_3$:2-propanol (3:1), dried ($Na_2SO_4$) and concentrated. The crude material was heated with a Dean-Stark apparatus at reflux in toluene to dry. Hot toluene solution was separated from solid, and the solution was concentrated to obtain the title compound. LCMS 239.23 (M+1−56), 295.23 (+1)

Step F (1R,3s,5S)-8-tert-butyl 3-methyl 3-(cyanomethyl)-8-azabicyclo[3.2.1]octane-3,8-dicarboxylate: To a solution of (1R,3s,5S)-8-(tert-butoxycarbonyl)-3-(cyanomethyl)-8-azabicyclo[3.2.1]octane-3-carboxylic acid (5.20 g, 17.7 mmol) in a mixture of MeOH (30 mL) and DCM (30 mL) was slowly added (trimethylsilyl)diazomethane (13.3 mL, 26.5 mmol) at rt. The mixture was stirred at the same temperature for 0.5 h. Acetic acid (~5 mL) was added to remove excess of (trimethylsilyl)diazomethane. The solution was concentrated, and the residue was used directly in the next step. $^1$H-NMR (500 MHz, $CDCl_3$): δ ppm 4.32 (2 H, m), 3.74 (3 H, s), 2.85 (2 H, s), 2.65 (2 H, m), 2.08 (2 H, m), 1.65 (4 H, m), 1.42 (9 H, s). LCMS: 253 (M+1−56).

Step G: (1R,3s,5S)-8-tert-butyl 3-methyl 3-(2-aminoethyl)-8-azabicyclo[3.2.1]octane-3,8-dicarboxylate: A mixture of (1R,3s,5S)-8-tert-butyl 3-methyl 3-(cyanomethyl)-8-azabicyclo[3.2.1]octane-3,8-dicarboxylate (3.5 g, 11.4 mmol) and platinum(iv) oxide (0.258 g, 1.14 mmol) in ethanol (20 mL) and AcOH (20 mL), was hydrogenated on a shaker (45 psi hydrogen) at rt for 48 hr. The catalyst was filtered off through a CELITE® pad. The filtration was concentrated and the residue was used directly in the next step. LCMS 313.25 (+1), 257.25 (+1−56).

Step H: (1R,3s,5S)-tert-butyl 2'-oxo-8-azaspiro[bicyclo[3.2.1]octane-3,3'-pyrrolidine]-8-carboxylate: A mixture of (1R,3s,5S)-8-tert-butyl 3-methyl 3-(2-aminoethyl)-8-azabicyclo[3.2.1]octane-3,8-dicarboxylate (3.50 g, 11.2 mmol) and potassium carbonate (7.74 g, 56.0 mmol) in MeOH (50 mL) was heated at 60° C. for 1 hr. The mixture was concentrated, and DCM (50 mL) was added. The suspension was filtered through a silica gel pad, and the filtrate was concentrated to give a solid which was directly used in the next step. $^1$H-NMR (500 MHz, $CDCl_3$): δ ppm 6.43 (1 H, bs), 4.25 (1 H, m), 4.37 (1 H, m), 3.32 (2 H, t, J=7.0 Hz), 2.24 (2 H, m), 2.35 (2 H, m), 1.97 (2 H, m), 1.82 (2 H, m), 1.45 (9 H, s), 1.46 (2 H, m). LCMS: 281 (M+1), 225 (M+1−56).

Step I: (1R,3s,5S)-tert-butyl 1'-(4-methyl-5-oxo-2,5-dihydrofuran-3-yl)-2'-oxo-8-azaspiro[bicyclo[3.2.1]octane-3,3'-pyrrolidine]-8-carboxylate: A mixture of (1R,3s,5S)-tert-butyl 2'-oxo-8-azaspiro[bicyclo[3.2.1]octane-3,3'-pyrrolidine]-8-carboxylate (2.00 g, 7.13 mmol), 4-methyl-5-oxo-2,5-dihydrofuran-3-yl trifluoromethanesulfonate (1.93 g, 7.85 mmol), diacetoxypalladium (0.080 g, 0.36 mmol), (9,9-dimethyl-9H-xanthene-4,5-diyl)bis(diphenylphosphine) (0.413 g, 0.713 mmol), potassium carbonate (2.96 g, 21.4 mmol) and water (0.386 g, 21.40 mmol) in toluene (100 mL) was heated at 60° C. under $N_2$ for 4 hr. The mixture was diluted with EtOAc (50 mL). The solid was filtered off through a CELITE® pad, and the filtrate was concentrated. The residue was purified by column chromatography (0-100% of EtOAc in hexane, then 100% EtOAc) to provide the title compound. LC-MS 321.03 (+1−56), 377.03 (+1).

Step J: (1R,3s,5S)-1'-(4-methyl-5-oxo-2,5-dihydrofuran-3-yl)-8-azaspiro[bicyclo[3.2.1]octane-3,3'-pyrrolidin]-2'-one: (1R,3s,5S)-tert-butyl 2'-oxo-8-azaspiro[bicyclo[3.2.1]octane-3,3'-pyrrolidine]-8-carboxylate was stirred with TFA (5 mL) in DCM (30 mL) at rt for 1 h. Volatiles were removed under reduced pressure. The residue was dissolved in methanol, and was loaded onto a Bond Elut SCX column (ion exchange) after the column was washed with 20 mL methanol. The column with the desired compound was eluted with methanol to remove TFA (~20 mL), the free base of the desired compound was eluted out with 2N $NH_3$ in methanol (~20 mL). The solution was concentrated to give the title compound as a free base (solid). $^1$H-NMR (500 MHz, $CDCl_3$): δ ppm 5.25 (1 H, s), 4.00 (2 H, t, J=6.9 Hz), 3.67 (2 H, m), 2.42 (2 H, t, J=6.9 Hz), 2.06 (3 H, s), 2.04 (2 H, m), 1.97 (2 H, m), 1.82 (2 H, m). LCMS 277.03(M+1), 321.03 (M+1−56).

Intermediates 33A and 33B

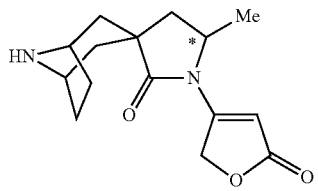 [SMILES: CC1CC2(CC3CCC(C2)N3)C(=O)N1C1=CC(=O)OC1]

(1R,3r,5S)-5'-methyl-1'-(5-oxo-2,5-dihydrofuran-3-yl)-8-azaspiro[bicyclo[3.2.1]octane-3,3'-pyrrolidin]-2'-one (Isomers A and B)

Step A: (1R,3r,5S)-8-tert-butyl 3-methyl 8-azabicyclo[3.2.1]octane-3,8-dicarboxylate: To a solution of commercially available (1R,3r,5S)-8-(tert-butoxycarbonyl)-8-azabicyclo[3.2.1]octane-3-carboxylic acid (10.0 g, 39.2 mmol) and methanol (4.75 mL, 118 mmol) in methylene chloride (200 mL) was added EDC (11.3 g, 58.8 mmol), diisopropylethylamine (13.7 mL, 78 mmol) and DMAP (0.479 g, 3.92 mmol). The resulting solution was stirred at rt for 16 h. The reaction solution was washed with potassium bisulfate (1 N, 200 mL), water (200 mL), saturated sodium bicarbonate, dried over sodium sulfate, and concentrated to give the title compound. LCMS: (M+1)+: 270.1.

Step B: (1R,3r,5S)-8-tert-butyl 3-methyl 3-(2-methylallyl)-8-azabicyclo[3.2.1]octane-3,8-dicarboxylate: To a solution of diisopropylamine (5.94 mL, 41.7 mmol) in tetrahydrofuran (5 mL) at 0° C. was added n-butyllithium (16.7 mL, 41.7 mmol) drop-wise, and the resulting solution was stirred at 0° C. for 0.5 h. This solution was added dropwise to a solution of the compound of Step A (7.48 g, 27.8 mmol) in tetrahydrofuran (90 mL) at −78° C. The resulting solution was stirred at −78° C. for 1 h and then 3-bromo-2-methylpropene (4.03 mL, 40.0 mmol) was added dropwise. After stirring at −78° C. for 1.5 h, the reaction was quenched by addition of saturated ammonium acetate. The mixture was diluted with ethyl acetate, washed with saturated ammonium acetate twice, dried over sodium sulfate, concentrated and the residue was purified on silica gel column using ethyl acetate-hexane as eluting solvents to give the title compound. LCMS: (M+1)+: 324.3.

Step C: (1R,3r,5S)-8-tert-butyl 3-methyl 3-(2-oxopropyl)-8-azabicyclo[3.2.1]octane-3,8-dicarboxylate: To a solution of (1R,3r,5S)-8-tert-butyl 3-methyl 3-(2-methylallyl)-8-azabicyclo[3.2.1]octane-3,8-dicarboxylate (7.99 g, 24.7 mmol) in dioxane (100 mL) and water (50 mL) was added sodium periodate (10.6 g, 49.4 mmol) and osmium tetroxide (0.126 g, 0.494 mmol). The resulting mixture was stirred at rt for 18 h and then sodium thiosulfate (1 g) was added. After stirring at rt for 0.5 h, the mixture was filtered and the filtrate was concentrated. The residue was dissolved in ethyl acetate (300 mL) and washed with brine, dried over sodium sulfate and concentrated. This residue was purified on silica gel using ethyl acetate and hexane as eluting solvents to give the title compound. LC/MS: (M+1)+: 326.2.

Step D: (1R,3r,5S)-tert-butyl 5'-methyl-2'-oxo-8-azaspiro[bicyclo[3.2.1]octane-3,3'-pyrrolidine]-8-carboxylate: To a solution of (1R,3r,5S)-8-tert-butyl 3-methyl 3-(2-oxopropyl)-8-azabicyclo[3.2.1]octane-3,8-dicarboxylate (7.90 g, 24.3 mmol) in methanol (50 mL) was added magnesium sulfate (5.84 g, 48.6 mmol), ammonium acetate (3.74 g, 48.6 mmol), and sodium cyanoborohydride (3.05 g, 48.6 mmol). The resulting mixture was heated at 80° C. in a sealed tube for 18 h. After cooling to rt, the mixture was filtered and the filtrate was concentrated and the residue was partitioned between methylene chloride and saturated sodium bicarbonate. The aqueous phase was extracted with methylene chloride, the combined organic phase was dried over sodium sulfate, concentrated and the residue was purified on silica gel using ethyl acetate as eluting solvent to give the title compound. LCMS: (M+1)+: 295.3.

Step E: (1R,3r,5S)-tert-butyl 5'-methyl-2'-oxo-1'-(5-oxo-2,5-dihydrofuran-3-yl)-8-azaspiro[bicyclo[3.2.1]octane-3,3'-pyrrolidine]-8-carboxylate, Isomer (A) and Isomer (B): To a solution of (1R,3r,5S)-tert-butyl 5'-methyl-2'-oxo-8-azaspiro[bicyclo[3.2.1]octane-3,3'-pyrrolidine]-8-carboxylate (2.41 g, 8.19 mmol) in toluene (30 mL) was added 3-bromofuranone (1.60 g, 9.82 mmol), Xantphos (0.474 g, 0.819 mmol), potassium carbonate (2.263 g, 16.37 mmol), water (0.442 g, 24.6 mmol), and palladium acetate (0.092 g, 0.409 mmol). The resulting mixture was flushed with nitrogen for 30 min and then heated at 65° C. for 16 h. After cooling to rt, the mixture was filtered and the filtrate was concentrated and the residue was purified on silica gel using ethyl acetate and hexane as eluting solvents to give the racemate (1R,3r,5S)-tert-butyl 5'-methyl-2'-oxo-1'-(5-oxo-2,5-dihydrofuran-3-yl)-8-azaspiro[bicyclo[3.2.1]octane-3,3'-pyrrolidine]-8-carboxylate (LC/MS: (M+1)+: 377.05). The racemate was separated on a chiral AS column (30×250 mm) using methanol/acetonitrile/carbon dioxide to give: Isomer (A), faster eluting enantiomer; LC/MS: (M+1)+: 377.04, and Isomer (B) the slower eluting enantiomer; LC/MS: (M+1)+: 377.03.

Step F: (1R,3r,5S)-5'-methyl-1'-(5-oxo-2,5-dihydrofuran-3-yl)-8-azaspiro[bicyclo[3.2.1]octane-3,3'-pyrrolidin]-2'-one Isomer A and Isomer B: TFA (3.27 mL, 42.5 mmol) was added to a solution of (1R,3r,5S)-tert-butyl 5'-methyl-2'-oxo-1'-(5-oxo-2,5-dihydrofuran-3-yl)-8-azaspiro[bicyclo[3.2.1]octane-3,3'-pyrrolidine]-8-carboxylate Isomer (A) (0.80 g, 2.1 mmol) in methylene chloride (5 mL) and the resulting solution was stirred at rt for 1 h. After removing the volatiles, the residue was dissolved in methanol (5 mL) and basified to free base on an ion-exchange column washed with methanol first followed by washing with 1N ammonia in methanol to give Isomer (A) of the title compound: LC/MS: (M+1)+: 277.07. TFA (3.27 mL, 42.5 mmol) was added to a solution of (1R,3r,5S)-tert-butyl 5'-methyl-2'-oxo-1'-(5-oxo-2,5-dihydrofuran-3-yl)-8-azaspiro[bicyclo[3.2.1]octane-3,3'-pyrrolidine]-8-carboxylate isomer Isomer (B) (0.8 g, 2.13 mmol) in methylene chloride (5 mL) and the resulting solution was stirred at rt for 1 h. After removing the volatiles, the residue was dissolved in methanol (5 mL) and basified to free base on an ion-exchange column washed with methanol first followed by washing with 1N ammonia in methanol to give Isomer B of the title compound. LC/MS: (M+1)+: 377.07

Intermediate 34

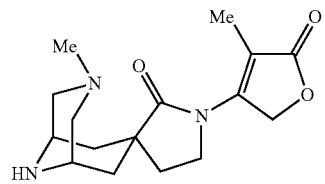 [SMILES: CC1=C(N2CCC3(CC4CN(C)CC(C3)N4)C2=O)COC1=O]

(1R,3's,5S)-3-methyl-1'-(4-methyl-5-oxo-2,5-dihydrofuran-3-yl)-3,9-diazaspiro[bicyclo[3.3.1]nonane-7,3'-pyrrolidin-]-2'-one Step A: (1R,5S)-tert-butyl 3-methyl-7-(((trifluoromethyl)sulfonyl)oxy)-3,9-diazabicyclo[3.3.1]non-6-ene-9-carboxylate: To a solution of commercially available (1R,5S)-tert-butyl 3-methyl-7-oxo-3,9-diazabicyclo[3.3.1]nonane-9-carboxylate (10.0 g, 39.3 mmol) in tetrahydrofuran (100 mL) was added LDA solution (23.6 mL, 47.2 mmol) at −78° C. drop-wise. The resulting solution was stirred at −78° C. for 0.5 h before being added to a solution of 2-[N,N-bis(trifluoromethanesulfonyl)amino]-5-chloropyridine (18.5 g, 47.2 mmol) in tetrahydrofuran (25 mL). The resulting solution was stirred at −78° C. for 2 h, then warmed to rt for 20 min before being quenched by addition of saturated ammonium chloride and ethyl acetate. The organic phase was washed with saturated sodium bicarbonate, dried over sodium sulfate, filtered, and concentrated and the residue was purified on silica gel using ethyl acetate and hexane as eluting solvents to give the title compound. LC/MS: (M+1)$^+$: 386.94.

Step B: (1R,5S)-9-tert-butyl 7-methyl 3-methyl-3,9-diazabicyclo[3.3.1]non-6-ene-7,9-dicarboxylate: To a solution of (1R,5S)-tert-butyl 3-methyl-7-(((trifluoromethyl)sulfonyl)oxy)-3,9-diazabicyclo[3.3.1]non-6-ene-9-carboxylate (14 g, 36 mmol) and diisopropylethylamine (9.47 mL, 54.3 mmol) in methanol (100 mL) and DMF (100 mL) was triphenylphosphine (0.95 g, 3.62 mmol) and palladium (II) acetate (0.407 g, 1.81 mmol). The mixture was stirred under carbon monoxide atmosphere for 24 h. The mixture was concentrated and then partitioned between ethyl acetate and water. The organic phase was washed with brine, dried over sodium sulfate, concentrated and the residue was purified on silica gel using ethyl acetate and hexane as eluting solvents to give the title compound. LC/MS: (M+1)$^+$: 297.2.

Step C: (1R,5S)-9-tert-butyl 7-methyl 3-methyl-3,9-diazabicyclo[3.3.1]nonane-7,9-dicarboxylate: To a solution of (1R,5S)-9-tert-butyl 7-methyl 3-methyl-3,9-diazabicyclo[3.3.1]non-6-ene-7,9-dicarboxylate (4.69 g, 15.8 mmol) in methanol (50 mL) was added palladium on carbon (10%, 1.684 g, 1.583 mmol) and the resulting mixture was subjected to hydrogenation under 40 psi for three days. After filtration through CELITE® under nitrogen the filtrate was concentrated to give the title compound. LC/MS: (M+1)$^+$: 299.1.

Step D: (1R,5S,7 s)-9-tert-butyl 7-methyl 7-(cyanomethyl)-3-methyl-3,9-diazabicyclo[3.3.1]nonane-7,9-dicarboxylate: To a solution of diisopropylamine (3.28 mL, 23.02 mmol) in tetrahydrofuran (5 mL) was added n-butyllithium (11.51 mL, 23.02) dropwise at 0° C., and the resulting solution was stirred at 0° C. for 0.5 h. To a solution of (1R,5S)-9-tert-butyl 7-methyl 3-methyl-3,9-diazabicyclo[3.3.1]nonane-7,9-dicarboxylate (4.58 g, 15.35 mmol) in tetrahydrofuran (50 mL) at −78° C. was added the above LDA solution drop-wise. After stirring at −78° C. for 1 h, bromoacetonitrile (1.54 mL, 22.1 mmol) was added drop-wise and the resulting solution was stirred at −78° C. for 1 h before quenching by addition of saturated ammonium chloride. The mixture was extracted with ethyl acetate. The combined organic phase was dried over sodium sulfate, concentrated and the residue was purified on silica gel using methanol and dichloromethane as eluting solvents to give the title compound. LC/MS: (M+1)$^+$: 338.2.

Step E: (1R,5S,7 s)-9-tert-butyl 7-methyl 7-(2-aminoethyl)-3-methyl-3,9-diazabicyclo[3.3.1]nonane-7,9-dicarboxylate: To a solution of (1R,5S,7 s)-9-tert-butyl 7-methyl 7-(cyanomethyl)-3-methyl-3,9-diazabicyclo[3.3.1]nonane-7,9-dicarboxylate (4.39 g, 13.0 mmol) in methanol (30 mL) was added platinum (IV) oxide (0.207 g, 0.911 mmol) and the resulting mixture was hydrogenated at 40 psi for 16 h. After filtration through CELITE® under nitrogen, the filtrate was concentrated to give the title compound. LC/MS: (M+1)$^+$: 342.2.

Step F: (1R,3's,5S)-tert-butyl 3-methyl-2'-oxo-3,9-diazaspiro[bicyclo[3.3.1]nonane-7,3'-pyrrolidine]-9-carboxylate: To a solution of (1R,5S,7s)-9-tert-butyl 7-methyl 7-(2-aminoethyl)-3-methyl-3,9-diazabicyclo[3.3.1]nonane-7,9-dicarboxylate (4.44 g, 13.0 mmol) in methanol (100 mL) was added potassium carbonate (10.8 g, 78 mmol), and the resulting solution was heated at reflux for 8 h. After cooling to rt the mixture was filtered and the filtrate was concentrated and the residue was dissolved in methylene chloride (200 mL) and dried over sodium sulfate, and concentrated to give the title compound. LC/MS: (M+1)$^+$: 310.26.

Step G: (1R,3's,5S)-tert-butyl 3-methyl-1'-(4-methyl-5-oxo-2,5-dihydrofuran-3-yl)-2'-oxo-3,9-diazaspiro[bicyclo[3.3.1]nonane-7,3'-pyrrolidine]-9-carboxylate: A mixture of (1R,3's,5S)-tert-butyl 3-methyl-2'-oxo-3,9-diazaspiro[bicyclo[3.3.1]nonane-7,3'-pyrrolidine]-9-carboxylate (4.0 g, 12.9 mmol), 4-methyl-5-oxo-2,5-dihydrofuran-3-yltrifluoromethanesulfonate (3.82 g, 15.5 mmol), Xantphos (0.748 g, 1.29 mmol), and potassium carbonate (3.57 g, 25.9 mmol) in toluene (100 mL) was degassed with nitrogen for 20 min followed by addition of palladium (II) acetate (0.145 g, 0.646 mmol). The resulting mixture was heated at 65° C. for 16 h. The reaction mixture was cooled to rt and filtered through CELITE®, the filtrate was concentrated and the residue was purified on a silica gel column to give the title compound. LC/MS: (M+1)$^+$: 406.21.

Step H: (1R,3's,5S)-3-methyl-1'-(4-methyl-5-oxo-2,5-dihydrofuran-3-yl)-3,9-diazaspiro[bicyclo[3.3.1]nonane-7,3'-pyrrolidin-]-2'-one: To a solution of the compound of Step G (2.63 g, 6.49 mmol) in dichloromethane (5 mL) was added trifluoroacetic acid (10 mL, 130 mmol) and the resulting solution was stirred at rt for 1 h. After removing the volatiles the residue was basified on ion exchange column washed with methanol followed by 1 N ammonia/methanol to give the title compound. LC/MS: (M+1)$^+$: 306.09.

Intermediate 35

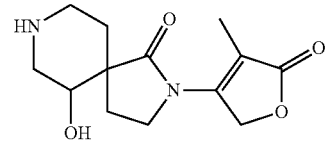 [SMILES: CC1=C(N2CCC3(CCNCC3O)C2=O)COC1=O]

6-Hydroxy-2-(4-methyl-5-oxo-2,5-dihydrofuran-3-yl)-2,8-diazaspiro[4.5]decan-1-one Step A: Ethyl 1-benzyl-4-(cyanomethyl)-3-oxopiperidine-4-carboxylate: To a flask charged with ethyl 1-benzyl-3-oxopiperidine-4-carboxylate (1.0 g, 3.8 mmol) and a stir bar was added K$_2$CO$_3$ (1.06 g, 7.6 mmol), bromoacetonitrile (0.92 g, 7.6 mmo0, and acetone (15 mL). The reaction was allowed to stir at RT for 2 hours. LC showed slow reaction. It was then heated to 45° C. for 3 hours. LC showed complete reaction at that point. The reaction was quenched with NH$_4$Cl, extracted with EtOAc, dried over Na$_2$SO$_4$, filtered and concentrated. The crude product was purified by MPLC to furnish the title compound. LCMS: m/z 301 (M+H)$^+$.

Step B: 8-Benzyl-6-hydroxy-2,8-diazaspiro[4.5]decan-1-one: To a flask charged with ethyl 1-benzyl-4-(cyanomethyl)-3-oxopiperidine-4-carboxylate (900 mg, 3.0 mmol) and a stir bar was added platinum oxide (100 mg, 0.44 mmol), MeOH (20 mL) and acetic acid (20 mL). The mixture was allowed to stir vigorously under an atmosphere of hydrogen for 24 hours. LC indicated complete reaction at that point. The catalyst was removed by filtration through a pad of CELITE®, and the filtrate was concentrated under reduced pressure. The residue was dissolved in EtOH (100 mL), and K$_2$CO$_3$ was added (2.1 g, 15 mmol). The mixture was heated to 90° C. for 4 hours. The reaction was cooled, and DCM was added (200 mL) to precipitate the solids. The solids were then removed by filtration, and the crude reaction was adsorbed onto silica gel, and flushed out with DCM and 10% MeOH (mixed with 10% NH$_4$OH) to give the title compound. LCMS: m/z 261 (M+H)$^+$.

Step C: 8-Benzyl-6-hydroxy-2-(4-methyl-5-oxo-2,5-dihydrofuran-3-yl)-2,8-diazaspiro[4.5]decan-1-one: To a flask charged with 8-benzyl-6-hydroxy-2,8-diazaspiro[4.5]decan-1-one (520 mg, 2.0 mmol) and a stir bar was added palladium acetate (22 mg, 0.10 mmol), K$_2$CO$_3$ (550 mg, 4.00 mmol), Xantphos (120 mg, 0.20 mmol), 4-methyl-5-oxo-2,5-dihydrofuran-3-yltrifluoromethanesulfonate (640 mg, 2.6 mmol), and water (110 mg, 6.0 mmol). The mixture was heated to 60° C. for 2 hours. LC showed complete reaction at that point. The reaction was diluted with EtOAc, washed with water, and the phases separated. The crude solution was dried over Na$_2$SO$_4$, filtered and concentrated to an oil. The oil was loaded onto a silica gel column, and purified by MPLC with Hexane and EtOAc. Two spots were separated with the desired molecular weight in a ratio of about 1 to 7. The more polar spot was the major product. LCMS: m/z 357 (M+H)$^+$.

Step D: 6-Hydroxy-2-(4-methyl-5-oxo-2,5-dihydrofuran-3-yl)-2,8-diazaspiro[4.5]decan-1-one To a solution of 8-benzyl-6-hydroxy-2-(4-methyl-5-oxo-2,5-dihydrofuran-3-yl)-2,8-diazaspiro[4.5]decan-1-one (150 mg, 0.42 mmol) in MeOH (2 mL) was added palladium on carbon (45 mg, 0.42 mmol) and a few drops of HOAc. The mixture was allowed to stir under an atmosphere of hydrogen for 16 hours. LC indicated complete reaction. The catalyst was filtered off, and the crude material was used without further purification. LCMS: m/z 267 (M+H)$^+$.

Intermediates 36A and 36B (Two Isomers)

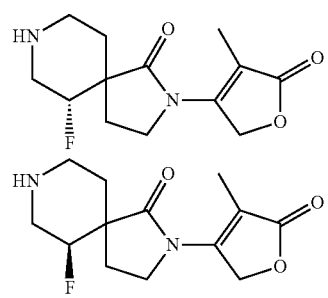

6-Fluoro-2-(4-methyl-5-oxo-2,5-dihydrofuran-3-yl)-2,8-diazaspiro[4.5]decan-1-one, Isomers A and B Step A: 8-benzyl-6-fluoro-2-(4-methyl-5-oxo-2,5-dihydrofuran-3-yl)-2,8-diazaspiro[4.5]decan-1-one Isomers A and B)

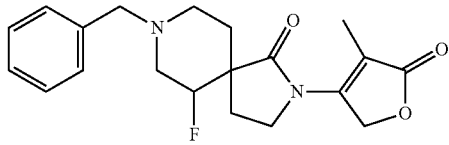 [SMILES: CC1=C(N2CCC3(CCN(Cc4ccccc4)CC3F)C2=O)COC1=O]

To a flask charged with DCM (5 mL) and a stir bar was added DAST (0.092 mL, 0.69 mmol) at −78° C., which was followed by addition of 8-benzyl-6-hydroxy-2-(4-methyl-5-oxo-2,5-dihydrofuran-3-yl)-2,8-diazaspiro[4.5]decan-1-one (I-35, Step C) (165 mg, 0.46 mmol) in DCM. The mixture was stirred at −78° C. for 15 minutes, and then allowed to warm up to RT slowly. The reaction was quenched with aq NaHCO$_3$ and after 3 hours at RT it was extracted with DCM, dried over sodium sulfate, and purified by MPLC with hexane and EtOAc. Two spots were collected with the desired molecule weight in the ratio of 1:4. The less polar compound, which is the minor isomer, was designated as Isomer A, and the more polar major isomer was designated as Isomer B. LCMS: m/z 359 (M+H)$^+$.

Step B-1: 6-Fluoro-2-(4-methyl-5-oxo-2,5-dihydrofuran-3-yl)-2,8-diazaspiro[4.5]decan-1-one Isomer B, I-36B:

To a solution of Isomer B from Step A (100 mg, 0.28 mmol) in DCE (2 mL) was added ACE-Cl (0.15 mL, 1.4 mmol). The mixture was heated to 80° C. for 3 hours. The solvent was then removed, and the residue was pumped under high vacuum for 15 minutes. The residue was then dissolved in MeOH (5 mL) and heated to reflux for 30 minutes. LC showed formation of the desired product. The reaction was concentrated, and the crude product was purified by MPLC with a DCM and MeOH system to obtain Isomer B of the title compound (which is I-36B). LCMS: m/z 269 (M+H)$^+$.

Step B-2: 6-Fluoro-2-(4-methyl-5-oxo-2,5-dihydrofuran-3-yl)-2,8-diazaspiro[4.5]decan-1-one (Isomer A, I-36A): The title intermediate (which is I-36A) was prepared following the same method as described in Step B-1, but starting from Isomer A from Step A). LCMS: m/z 269 (M+H)$^+$.

Intermediates 37A and 37B

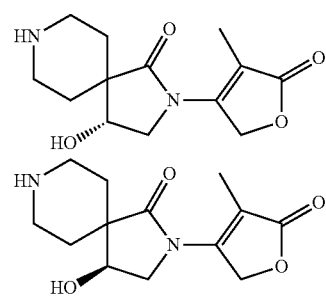

4-hydroxy-2-(4-methyl-5-oxo-2,5-dihydrofuran-3-yl)-2,8-diazaspiro[4.5]decan-1-one, Isomer A and Isomer B Step A: 1-tert-butyl 4-methyl 4-(2-((tert-butoxycarbonyl)amino)-1-hydroxyethyl)piperidine-1,4-dicarboxylate: To a solution of LDA (prepared by adding n-butyllithium (20.0 mL, 49.3 mmol) to diisopropylamine (5.16 mg, 51.0 mmol) in THF (40 mL) at 0° C., stirred for 30 min) was added 1-tert-butyl 4-methyl piperidine-1,4-dicarboxylate (4.00 g, 16.4 mmol) in TMEDA (15 mL, 99 mmol) drop-wise via syringe pump at −78° C. for 10 min. The mixture was stirred at the same temperature for 30 min, then tert-butyl (2-oxoethyl)carbamate (8.11 g, 51.0 mmol) in THF (20 mL) was added slowly by syringe pump for 15 min. The mixture was stirred at −78° C. for 30 min, quenched with saturated NH$_4$Cl at −78° C., warmed up to rt and diluted with EtOAc (200 mL). The organic layer was separated, and the aqueous layer was extracted with EtOAc (100 mL). The combined organic layers were washed with brine, dried (MgSO$_4$), and concentrated. The residue was purified by column chromatography (80 g, silical gel, MeOH/DCM, gradient 0-10%, monitor at 210 nm) to afford title compound. LC/MS: [(M+1)]$^+$=403

Step B: tert-Butyl 4-hydroxy-1-oxo-2,8-diazaspiro[4.5]decane-8-carboxylate: To a solution of 1-tert-butyl 4-methyl 4-(2-((tert-butoxycarbonyl)amino)-1-hydroxyethyl)piperidine-1,4-dicarboxylate (4000 mg, 9.94 mmol) in DCM (100 mL) was added TFA (23 mL, 298 mmol) at 0° C. and the resulting solution was stirred for 2 h. After removing the volatiles, it was put on high vacuum briefly to remove excess TFA, and the residue was dissolved in MeOH (100 mL), and potassium carbonate (13.7 g, 99 mmol) was added. The reaction mixture was heated at 60° C. for 2 h. After cooling to room temperature, aqueous NaHCO$_3$ (50 mL) was added to the reaction mixture. (BOC)$_2$O (6.51 g, 29.8 mmol) was added, and the reaction mixture was stirred overnight. The reaction mixture was extracted with DCM, dried with MgSO$_4$, and concentrated to give the crude product, which was purified by column chromatography (0-20% MeOH/DCM, monitor at 210 nm) to afford the title compound. LC/MS: [(M+1)]$^+$=271

Step C: tert-Butyl 4-hydroxy-2-(4-methyl-5-oxo-2,5-dihydrofuran-3-yl)-1-oxo-2,8-diazaspiro[4.5]decane-8-carboxylate, Isomer A and Isomer B

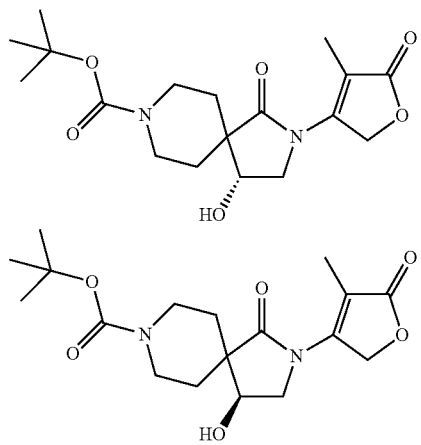

To a round bottom flask was charged tert-butyl 4-hydroxy-1-oxo-2,8-diazaspiro[4.5]decane-8-carboxylate (400 mg, 1.48 mmol), 4-methyl-5-oxo-2,5-dihydrofuran-3-yl trifluoromethanesulfonate (546 mg, 2.22 mmol), Pd$_2$(dba)$_3$ (33.9 mg, 0.037 mmol), Xantphos (64.2 mg, 0.111 mmol), and cesium carbonate (964 mg, 2.96 mmol). The flask was equipped with a condenser, vacuumed and back filled with N$_2$ and filled with dioxane (6 mL). The reaction mixture was heated at 90° C. overnight, and filtered through CELITE®. The filtrate was evaporated to give the crude product, which was purified by column chromatography (0-10% MeOH/DCM) to give the title compound as a racemate. LCMS: [(M+1)]$^+$=367. The racemic mixture was separated by SFC-HPLC, using the following conditions: chiralcel OJ, 21×250 mm, 10% MeOH+0.2 DEA, 50 mL/min to afford Isomer A (faster eluting enantiomer) LC/MS: [(M+1)]$^+$=367, and Isomer B (slower eluting enantiomer) LC/MS: [(M+1)]$^+$=367.

Step D: 4-hydroxy-2-(4-methyl-5-oxo-2,5-dihydrofuran-3-yl)-2,8-diazaspiro[4.5]decan-1-one, Isomer A and Isomer B: The title compounds were prepared from Isomers A and B of tert-Butyl 4-hydroxy-2-(4-methyl-5-oxo-2,5-dihydrofuran-3-yl)-1-oxo-2,8-diazaspiro[4.5]decane-8-carboxylate, respectively, using TFA in a similar fashion as described previously for 1-19. Isomer A: LC/MS: [(M+1)]$^+$=267; Isomer B: LC/MS: [(M+1)]$^+$=267.

Intermediate 38

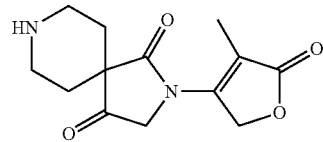 [SMILES: CC1=C(N2CC(=O)C3(CCNCC3)C2=O)COC1=O]

2-(4-Methyl-5-oxo-2,5-dihydrofuran-3-yl)-2,8-diazaspiro[4.5]decane-1,4-dione

Step A: tert-Butyl 2-(4-methyl-5-oxo-2,5-dihydrofuran-3-yl)-1,4-dioxo-2,8-diazaspiro[4.5]decane-8-carboxylate: To tert-butyl 4-hydroxy-2-(4-methyl-5-oxo-2,5-dihydrofuran-3-yl)-1-oxo-2,8-diazaspiro[4.5]decane-8-carboxylate (I-37, Step C) (200 mg, 0.546 mmol) in DCM (2.8 mL) was added sodium bicarbonate (68.8 mg, 0.819 mmol) and Dess-Martin periodinane (347 mg, 0.819 mmol). The reaction mixture was vigorously stirred for 1.5 h, then quenched with 10% Na$_2$S$_2$O$_3$, NaHCO$_3$, and stirred for 20 min. The aqueous layer was extracted with DCM, and the organic layers were washed with brine, dried, and concentrated to give the title compound. LC/MS: [(M+1)]$^+$=365;

Step B: 2-(4-Methyl-5-oxo-2,5-dihydrofuran-3-yl)-2,8-diazaspiro[4.5]decane-1,4-dione: The title compound was prepared from tert-Butyl 2-(4-methyl-5-oxo-2,5-dihydrofuran-3-yl)-1,4-dioxo-2,8-diazaspiro[4.5]decane-8-carboxylate in a similar fashion as described in I-19. LC/MS: [(M+1)]$^+$=265

Intermediates 39A and 39B

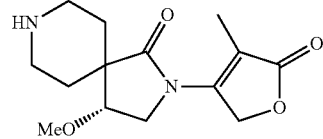

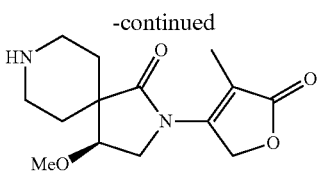

4-Methoxy-2-(4-methyl-5-oxo-2,5-dihydrofuran-3-yl)-2,8-diazaspiro[4.5]decan-1-one, Isomer A and Isomer B Step A: tert-Butyl 4-methoxy-2-(4-methyl-5-oxo-2,5-dihydrofuran-3-yl)-1-oxo-2,8-diazaspiro[4.5]decane-8-carboxylate (Enantiomer A and Enantiomer B): To a solution of tert-butyl 4-hydroxy-2-(4-methyl-5-oxo-2,5-dihydrofuran-3-yl)-1-oxo-2,8-diazaspiro[4.5]decane-8-carboxylate (100 mg, 0.273 mmol) in acetonitrile (1 mL) was added iodomethane (171 µL, 2.73 mmol) and silver oxide (69.6 mg, 0.300 mmol). The vial was sealed, wrapped with aluminum foil, and stirred at 58° C. for 15 h. The reaction mixture was filtered through CELITE®, concentrated to give the crude product, which was purified by column chromatography (0-10% MeOH/DCM) to afford the title compound as a mixture of enantiomers. LC/MS: [(M+1)]⁺=381. The racemic mixture was separated by SFC-HPLC, using the following conditions: chiralcel AD-H, 2×25 cm, 15% MeOH, 60 mL/min to afford faster eluting Enantiomer A: LC/MS: [(M+1)]⁺=381; and slower eluting Enantiomer B: LC/MS: [(M+1)]⁺=381

Step B: 4-methoxy-2-(4-methyl-5-oxo-2,5-dihydrofuran-3-yl)-2,8-diazaspiro[4.5]decan-1-one, Isomer A and Isomer B: The individual isomers of the title compound were prepared from each of the single Enantiomers from the previous step in a similar fashion as described for 1-19, Step B, using TFA. Isomer A (derived from Enantiomer A, Step A): LCMS: [(M+1)]⁺=281. Isomer B (derived from Enantiomer B, Step A): LC/MS: [(M+1)]⁺=281.

Intermediate 40

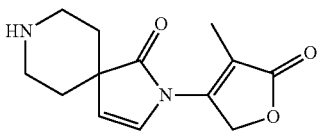 [SMILES: CC1=C(N2C=CC3(CCNCC3)C2=O)COC1=O]

2-(4-Methyl-5-oxo-2,5-dihydrofuran-3-yl)-2,8-diazaspiro[4.5]dec-3-en-1-one

Step A: tert-Butyl 2-(4-methyl-5-oxo-2,5-dihydrofuran-3-yl)-1-oxo-2,8-diazaspiro[4.5]dec-3-ene-8-carboxylate: To a solution of tert-butyl 4-hydroxy-2-(4-methyl-5-oxo-2,5-dihydrofuran-3-yl)-1-oxo-2,8-diazaspiro[4.5]decane-8-carboxylate (300 mg, 0.819 mmol) in DCM (8.2 mL) at 0° C. was added DBU (370 µA, 2.46 mmol), and XtalFluor-E® (562 mg, 2.46 mmol). The mixture was stirred overnight while warming up to rt, and quenched with aqueous NaHCO₃. The organic layer was separated and the aqueous layer was extracted with DCM (30 mL). The combined organic layers were dried (MgSO₄) and purified by column chromatography (0-100% EtOAc/hex) to give the title compound. LC/MS: [(M+1)]⁺=349

Step B: 2-(4-Methyl-5-oxo-2,5-dihydrofuran-3-yl)-2,8-diazaspiro[4.5]dec-3-en-1-one: The title compound was prepared from tert-Butyl 2-(4-methyl-5-oxo-2,5-dihydrofuran-3-yl)-1-oxo-2,8-diazaspiro[4.5]dec-3-ene-8-carboxylate using TFA in an analogous fashion to that described for making 1-19, Step B. LC/MS: [(M+1)]⁺=249.

Intermediate 41

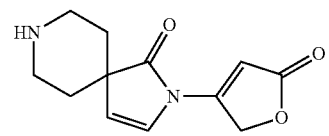 [SMILES: O=C1C=C(N2C=CC3(CCNCC3)C2=O)CO1]

2-(5-oxo-2,5-dihydrofuran-3-yl)-2,8-diazaspiro[4.5]dec-3-en-1-one

Step A: tert-Butyl 4-hydroxy-1-oxo-2-(5-oxo-2,5-dihydrofuran-3-yl)-2,8-diazaspiro[4.5]decane-8-carboxylate: To a round bottom flask was charged tert-butyl 4-hydroxy-1-oxo-2,8-diazaspiro[4.5]decane-8-carboxylate (300 mg, 1.11 mmol), 4-bromofuran-2(5H)-one (271 mg, 1.66 mmol), Pd(OAc)₂ (24.9 mg, 0.111 mmol), Xantphos (96 mg, 0.166 mmol), and K₂CO₃ (307 mg, 2.22 mmol). The flask was sealed, vacuumed and back filled with N₂ and filled with dioxane (4.5 mL) and H₂O (60.0 µL, 3.33 mmol). The reaction mixture was heated at 90° C. overnight, then filtered through CELITE®, and evaporated to give the crude product, which was purified by column chromatography (0-10% MeOH/DCM) to give the title compound. LC/MS: [(M+1)]⁺=353

Step B: tert-Butyl 1-oxo-2-(5-oxo-2,5-dihydrofuran-3-yl)-2,8-diazaspiro[4.5]dec-3-ene-8-carboxylate: To a solution of tert-butyl 4-hydroxy-1-oxo-2-(5-oxo-2,5-dihydrofuran-3-yl)-2,8-diazaspiro[4.5]decane-8-carboxylate (210 mg, 0.596 mmol) in DCM (6 mL) at 0° C. was added DBU (269 µA, 1.79 mmol), and XtalFluor-E® (409 mg, 1.79 mmol). The reaction mixture was stirred overnight while warming up to rt, then quenched with aqueous NaHCO₃. The organic layer was separated and the aqueous layer was extracted with DCM (30 mL). The combined organic layers were dried (MgSO₄) and purified by column chromatography (0-100% EtOAc/hex) to give the title compound. LCMS: [(M+1)]⁺=335;

Step C: 2-(5-oxo-2,5-dihydrofuran-3-yl)-2,8-diazaspiro[4.5]dec-3-en-1-one: The title compound was prepared from tert-Butyl 1-oxo-2-(5-oxo-2,5-dihydrofuran-3-yl)-2,8-diazaspiro[4.5]dec-3-ene-8-carboxylate using TFA in an analogous fashion to that described for 1-19, Step B. LC/MS: [(M+1)]⁺=235

Intermediate 42

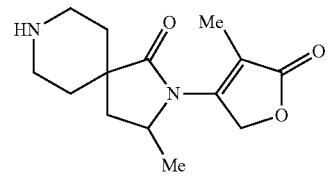 [SMILES: CC1=C(N2C(=O)C3(CCNCC3)CC2C)COC1=O]

3-methyl-2-(4-methyl-5-oxo-2,5-dihydrofuran-3-yl)-2,8-diazaspiro[4.5]decan-1-one The title compound was prepared in two steps in an analogous fashion to that described for 3-methyl-2-(5-oxo-2,5-dihydrofuran-3-yl)-2,8-diazaspiro[4.5]decan-1-one (I-22), except starting from 4-methyl-5-oxo-2,5-dihydrofuran-3-yl-trifluoromethanesulfonate (I-9). LC-MS (IE, m/z): 265 (M+1)$^+$.

Intermediate 43

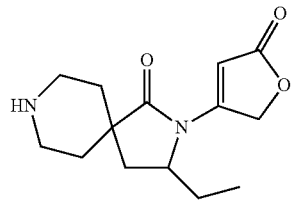 [SMILES: CCC1CC2(CCNCC2)C(=O)N1C1=CC(=O)OC1]

3-ethyl-2-(5-oxo-2,5-dihydrofuran-3-yl)-2,8-diazaspiro[4.5]decan-1-one

Step A: 1-tert-butyl 4-ethyl 4-(2-bromoallyl)piperidine-1,4-dicarboxylate: Lithium diisopropylamide (29.1 mL, 58.3 mmol) was added dropwise at −78° C. To a solution of 1-tert-butyl 4-ethyl piperidine-1,4-dicarboxylate (9.56 mL, 38.9 mmol) in THF (200 mL), and stirred at this temperature for 50 min. 2,3-Dibromoprop-1-ene (5.47 mL, 56.0 mmol) in THF (10 mL) was added to the reaction mixture slowly and the resulting mixture was stirred for 1.5 hr at −78° C. The reaction mixture was quenched with NH$_4$Cl solution (15 mL) and was allowed to warm to room temperature and the aqueous layer was extracted with EtOAc (30 mL×3). The combined organics were washed with brine (30 mL), dried over MgSO$_4$ and concentrated to get the crude product which was purified by silica gel column chromatography (RediSep 220 g Gold column) using (0-30) % EtOAc/Hexanes as mobile phase to give the title compound.

Step B: 1-tert-butyl 4-ethyl 4-(2-methylenebutyl)piperidine-1,4-dicarboxylate: To a solution of 1-tert-butyl 4-ethyl 4-(2-bromoallyl)piperidine-1,4-dicarboxylate (5.0 g, 13.3 mmol) in THF (80 mL) in a sealed tube was added BINAP (3.31 g, 5.32 mmol), diethylzinc (15.95 mL, 15.95 mmol) and Pd(OAc)$_2$ (0.597 g, 2.66 mmol) and the resulting mixture was degassed and heated for 16 hours at 100° C. The reaction mixture was evaporated to remove solvent under reduced pressure and the crude product was purified by silica gel column chromatography (RediSep 220 g Gold column) using (0-30) % EtOAc/Hexanes as mobile phase and the title compound was isolated.

Step C: 1-tert-butyl 4-ethyl 4-(2-oxobutyl)piperidine-1,4-dicarboxylate: Potassium tetrahydroxydioxoosmium (0.041 g, 0.111 mmol) was added to a solution of 1-tert-butyl 4-ethyl 4-(2-methylenebutyl)piperidine-1,4-dicarboxylate (1.0 g, 3.07 mmol) in acetone (20 mL) and water (20 mL) and stirred for 10 min. Solid sodium periodate (2.62 g, 12.26 mmol) was added in four portions during 1 hour and the reaction temperature was maintained below 40° C. using an ice-bath. The resulting mixture was stirred for 1 hour at room temperature. At this point LCMS showed incomplete reaction. Another 0.036 eq. of potassium tetrahydroxydioxoosmium (0.041 g, 0.111 mmol) was added and the mixture was then stirred at rt for 2 hours. LCMS after 2 hours showed completion of the reaction. The suspension was filtered and filtrate was concentrated to remove acetone, and the aqueous layer was extracted with DCM (15 mL×3). The combined organic layers were washed with 10% Na$_2$S$_2$O$_3$ solution (20 ml×2), dried over anhydrous Na$_2$SO$_4$, filtered, then concentrated to get the crude product which was purified by silica gel column chromatography (80 g RediSep Gold column) using (0-35) % EtOAc/Hexanes as mobile phase and the title compound was isolated.

Step D: tert-butyl 3-ethyl-1-oxo-2,8-diazaspiro[4.5]decane-8-carboxylate: To a stirred solution of 1-tert-butyl 4-ethyl 4-(2-oxobutyl)piperidine-1,4-dicarboxylate (0.78 g, 2.38 mmol) in ethanol (24 mL) in a sealed tube was added ammonium acetate (2.39 g, 31.0 mmol), sodium cyanoborohydride (0.422 g, 6.72 mmol) and magnesium sulfate (1.577 g, 13.10 mmol) and the resulting mixture was heated for 16 hours at 80° C. The reaction mixture was filtered over CELITE® to remove MgSO$_4$ and the filtrate was concentrated. The residue was re-dissolved in DCM (20 mL) and washed with saturated NaHCO$_3$ (10 ml), water (10 mL) and brine (10 mL). The organic layer was dried over anhydrous MgSO$_4$ filtered, concentrated, then purified by silica gel column chromatography (40 g RediSep Gold column) using (0-10) % MeOH/EtOAc to give the title compound.

Steps E and F: 3-ethyl-2-(5-oxo-2,5-dihydrofuran-3-yl)-2,8-diazaspiro[4.5]decan-1-one: The title compound was prepared in two steps from tert-butyl 3-ethyl-1-oxo-2,8-diazaspiro[4.5]decane-8-carboxylate in an analogous fashion as described for 3-methyl-2-(5-oxo-2,5-dihydrofuran-3-yl)-2,8-diazaspiro[4.5]decan-1-one (I-22).

Intermediate 44

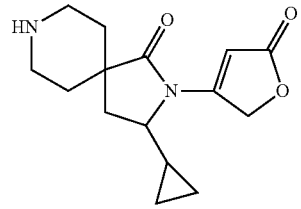 [SMILES: O=C1C=C(N2C(=O)C3(CCNCC3)CC2C2CC2)CO1]

3-cyclopropyl-2-(5-oxo-2,5-dihydrofuran-3-yl)-2,8-diazaspiro[4.5]decan-1-one

Step A: 1-tert-butyl 4-ethyl 4-(2-cyclopropylallyl)piperidine-1,4-dicarboxylate: 1-tert-butyl 4-ethyl 4-(2-bromoallyl)piperidine-1,4-dicarboxylate (1.0 g, 2.66 mmol), potassium cyclopropyltrifluoroborate (0.413 g, 2.79 mmol), cesium carbonate (2.60 g, 7.97 mmol) and [1,1'-bis(diphenylphosphino)ferrocene]dichloropalladium(II) (0.058 g, 0.080 mmol) were taken up in toluene (14 mL) and water (1.39 mL) in a microwave vial, degassed and heated at 80° C. overnight. The reaction mixture was cooled and LC/MS was taken which showed almost completion of reaction. The reaction mixture was diluted with EtOAc and water. Aqueous layer was extracted with EtOAc (2×), the combined organic layers were dried over anhydrous MgSO$_4$, filtered, concentrated, and purified by silica gel column chromatography (RediSep Gold, 80 g) using (0-30) % EtOAc/Hexanes as mobile phase to afford the title compound.

3-cyclopropyl-2-(5-oxo-2,5-dihydrofuran-3-yl)-2,8-diazaspiro[4.5]decan-1-one The title compound was prepared from 1-tert-butyl 4-ethyl 4-(2-cyclopropylallyl)piperidine-1,4-dicarboxylate in four steps in an analogous fashion as described for 3-ethyl-2-(5-oxo-2,5-dihydrofuran-3-yl)-2,8-diazaspiro[4.5]decan-1-one (I-43).

Intermediate 45

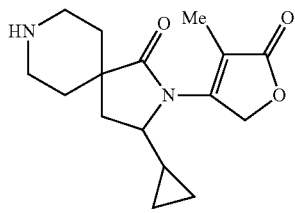 [SMILES: CC1=C(N2C(=O)C3(CCNCC3)CC2C2CC2)COC1=O]

3-cyclopropyl-2-(4-methyl-5-oxo-2,5-dihydrofuran-3-yl)-2,8-diazaspiro[4.5]decan-1-one The title compound was prepared in an analogous fashion to 1-44, but using 4-methyl-5-oxo-2,5-dihydrofuran-3-yltrifluoromethanesulfonate.

Intermediate 46

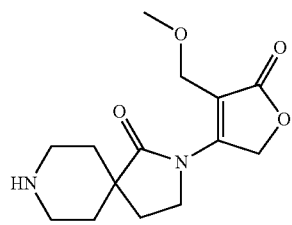 [SMILES: COCC1=C(N2CCC3(CCNCC3)C2=O)COC1=O]

2-(4-(methoxymethyl)-5-oxo-2,5-dihydrofuran-3-yl)-2,8-diazaspiro[4.5]decan-1-one Step A: tert-butyl 2-(4-bromo-5-oxo-2,5-dihydrofuran-3-yl)-1-oxo-2,8-diazaspiro[4.5]decane-8-carboxylate: tert-butyl 1-oxo-2-(5-oxo-2,5-dihydrofuran-3-yl)-2,8-diazaspiro[4.5]decane-8-carboxylate (I-16, Step A) (2.73 g, 8.12 mmol) was dissolved in DCM (70 mL) and was treated with N-bromosuccinimide (1.73 g, 9.74 mmol) at 25° C. and the resulting mixture was stirred overnight at room temperature. The next day, the reaction mixture was diluted with DCM and was washed with water and brine then dried over $Na_2SO_4$. Removing solvent gave crude product that was purified by silica gel column chromatography (80 g RediSep Gold Column) using (25-80) % EtOAc/Hexanes as mobile phase to afford the title compound.

Step B: tert-butyl 1-oxo-2-(5-oxo-4-vinyl-2,5-dihydrofuran-3-yl)-2,8-diazaspiro[4.5]decane-8-carboxylate: tert-butyl 2-(4-bromo-5-oxo-2,5-dihydrofuran-3-yl)-1-oxo-2,8-diazaspiro[4.5]decane-8-carboxylate (2.2 g, 5.30 mmol), potassium trifluoro(vinyl)borate (1.06 g, 7.95 mmol), [1,1'-bis(diphenylphosphino)ferrocene]dichloropalladium(II) (0.345 g, 0.530 mmol) and potassium phosphate tribasic (10.60 g, 10.60 mmol) were taken up in THF (44.1 mL) in a sealed tube, de-gassed and the resulting mixture was heated overnight at 70° C. The reaction mixture was cooled to room temperature and then was diluted with EtOAc and water. After separation of layers, the aqueous layer was extracted with EtOAc (2×). The combined organic layers were dried over anhydrous $MgSO_4$, filtered, concentrated and purified by silica gel column chromatography using (30-100) % EtOAc/hexanes as mobile phase to provide the title compound.

Step C: tert-butyl 2-(4-formyl-5-oxo-2,5-dihydrofuran-3-yl)-1-oxo-2,8-diazaspiro[4.5]decane-8-carboxylate: tert-butyl 1-oxo-2-(5-oxo-4-vinyl-2,5-dihydrofuran-3-yl)-2,8-diazaspiro[4.5]decane-8-carboxylate (1.6 g, 4.4 mmol) was dissolved in acetone (36 mL) and water (36 mL), then $K_2OsO_4 \cdot 2H_2O$ was added and the mixture was stirred for ~5 min. Solid sodium periodate (3.77 g, 17.6 mmol) was added in 4 portions during 1 hour and the reaction temperature was maintained below 40° C. using an ice-bath. The resulting mixture was stirred for 1 hour at room temperature. LCMS after 2 hours showed complete consumption of starting material. The suspension was filtered and the filtrate was concentrated to remove acetone. The aqueous layer was extracted with DCM (3×). Combined organic layers were washed with 10% $Na_2S_2O_3$ solution (2×), dried over anhydrous $Na_2SO_4$, filtered, concentrated to obtain the title compound, which was taken to the next step without further purification.

Step D: tert-butyl 2-(4-(hydroxymethyl)-5-oxo-2,5-dihydrofuran-3-yl)-1-oxo-2,8-diazaspiro[4.5]decane-8-carboxylate: tert-butyl 2-(4-formyl-5-oxo-2,5-dihydrofuran-3-yl)-1-oxo-2,8-diazaspiro[4.5]decane-8-carboxylate (1.18 g, 3.24 mmol) was dissolved in THF (13 mL) and MeOH (13 mL) and the mixture was cooled to −78° C. and stirred for 15 min. Sodium borohydride (0.147 g, 3.89 mmol) was added in two equal portions and the resulting mixture was stirred for ~15 min. at −78° C. LC-MS after 15 minutes stirring at −78° C. showed complete consumption of starting material. The reaction mixture was diluted with ethyl acetate and quenched with aqueous ammonium chloride solution at −78° C. The aqueous layer was extracted with EtOAc (2×), combined organic layers were washed with water, brine, then dried ($MgSO_4$) and filtered, and the solvent was evaporated under reduced pressure to obtain the product, which was taken to the next step without purification.

Step E: tert-butyl 2-(4-(methoxymethyl)-5-oxo-2,5-dihydrofuran-3-yl)-1-oxo-2,8-diazaspiro[4.5]decane-8-carboxylate: tert-butyl 2-(4-(hydroxymethyl)-5-oxo-2,5-dihydrofuran-3-yl)-1-oxo-2,8-diazaspiro[4.5]decane-8-carboxylate (0.42 g, 1.15 mmol), silver oxide (0.292 g, 1.26 mmol) and methyl iodide (0.358 mL, 5.73 mmol) were taken up in DCM (5 mL) and stirred over night at room temperature under nitrogen. Additional silver oxide (0.292 g, 1.26 mmol) and methyl iodide (0.358 mL, 5.73 mmol) were added to the mixture with DCE (8 mL) and the resulting mixture was heated at 54° C. overnight. The reaction mixture was filtered through CELITE® to remove silver oxide, concentrated, and purified by silica gel column chromatography (40 g RediSep Gold column) using (20-80) % EtOAc/DCM as mobile phase to afford the title compound.

Step F: 2-(4-(methoxymethyl)-5-oxo-2,5-dihydrofuran-3-yl)-2,8-diazaspiro[4.5]decan-1-one: The title compound was prepared from tert-butyl 2-(4-(methoxymethyl)-5-oxo-2,5-dihydrofuran-3-yl)-1-oxo-2,8-diazaspiro[4.5]decane-8-carboxylate in an analogous fashion as described for 3-methyl-2-(5-oxo-2,5-dihydrofuran-3-yl)-2,8-diazaspiro[4.5]decan-1-one (I-22, last step).

Intermediate 47

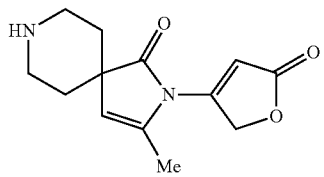

3-methyl-2-(5-oxo-2,5-dihydrofuran-3-yl)-2,8-diazaspiro[4.5]dec-3-en-1-one

Step A: 1-tert-Butyl 4-methyl 4-(2-((tert-butoxycarbonyl)amino)-1-hydroxypropyl)piperidine-1,4-dicarboxylate: To a solution of LDA (prepared by adding n-BuLi (27.7 mL, 55.5 mmol) to diisopropylamine (8.04 mL, 57.3 mmol) in THF (40 mL) at 0° C., stir for 30 min) was added 1-tert-butyl 4-methyl piperidine-1,4-dicarboxylate (4500 mg, 18.5 mmol) in TMEDA (16.6 mL, 111 mmol) dropwise via syringe pump at −78° C. for 20 min. The mixture was stirred at the same temperature for 30 min, and (S)-tert-butyl (1-oxopropan-2-yl)carbamate (9931 mg, 57.3 mmol) in THF (20 mL) was added slowly by syringe pump for 20 min. The mixture was stirred at −78° C. for 30 min, and quenched with saturated NH4Cl at −78° C., warmed up to rt and diluted with EtOAc (200 mL). The organic layer was separated, and the aqueous layer was extracted with EtOAc (100 mL). The combined organic layers were washed with brine, dried (MgSO4), and concentrated. The residue was purified by column chromatography (MeOH/DCM, gradient 0-10%) to afford the title compound. LC/MS: [(M+1)]+=417

Step B: tert-Butyl 4-hydroxy-3-methyl-1-oxo-2,8-diazaspiro[4.5]decane-8-carboxylate: To a solution of 1-tert-butyl 4-methyl 4-(2-((tert-butoxycarbonyl)amino)-1-hydroxypropyl)piperidine-1,4-dicarboxylate (8000 mg, 19.2 mmol) in DCM (190 mL) was added TFA (44.4 mL, 576 mmol) at 0° C. and the resulting solution was stirred for 2 h. After removing the volatiles, high vacuum was applied briefly to remove excess TFA, and the residue was dissolved in MeOH (190 mL), and K2CO3 (26.5 g, 192 mmol) was added. The reaction mixture was heated at 60° C. for 2 h. After cooling to room temperature, saturated NaHCO3 solution (60 mL) was added, followed by (BOC)2O (12.6 g, 57.6 mmol). The reaction mixture was stirred overnight, and extracted with DCM. The organic layer was dried with MgSO4, and concentrated to give the crude product, which was purified by column chromatography (0-20% MeOH/DCM, monitored at 210 nM) to give the title compound. LCMS: [(M+1)]+=285

Step C: tert-Butyl 4-hydroxy-3-methyl-1-oxo-2-(5-oxo-2,5-dihydrofuran-3-yl)-2,8-diazaspiro[4.5]decane-8-carboxylate: To a round bottom flask was charged tert-butyl 4-hydroxy-3-methyl-1-oxo-2,8-diazaspiro[4.5]decane-8-carboxylate (1000 mg, 3.52 mmol), 4-bromofuran-2(5H)-one (860 mg, 5.28 mmol), Pd(OAc)2 (79 mg, 0.352 mmol), Xantphos (305 mg, 0.528 mmol), and K2CO3 (972 mg, 7.03 mmol). The flask was sealed, vacuumed and back filled with N2 and filled with dioxane (14 mL) and water (190 μL, 10.6 mmol). The reaction mixture was heated at 90° C. overnight, and filtered through CELITE®. The filtrate was evaporated to give the crude product, which was purified by column chromatography (0-10% MeOH/DCM, came out at 6% MeOH/DCM, followed by another column with 0-100% EtOAc/hex) to give the title compound. LCMS: [(M+1)]+=367

Step D: tert-butyl 4-iodo-3-methyl-1-oxo-2-(5-oxo-2,5-dihydrofuran-3-yl)-2,8-diazaspiro[4.5]decane-8-carboxylate: To a solution of the compound of step C (370 mg, 1.01 mmol) in toluene (20 mL) at rt was added PPh3 (397 mg, 1.515 mmol), imidazole (137 mg, 2.02 mmol), and I2 (384 mg, 1.515 mmol). The mixture was stirred for 10 h at 100° C., and quenched with NaHCO3 aqueous solution. The organic layer was diluted with DCM, separated, and the aqueous layer was extracted with DCM. The combined organic layers were dried (MgSO4) and purified by column chromatography (0-100% EtOAc/hex) to give the title compound. LC/MS: [(M+1−56)]+=421

Step E: 4-iodo-3-methyl-2-(5-oxo-2,5-dihydrofuran-3-yl)-2,8-diazaspiro[4.5]decan-1-one: The compound of Step D (100 mg, 0.210 mmol) in DCM (1.1 mL) was treated with TFA (485 μL, 6.30 mmol) at 0° C. to remove the Boc group which provided the TFA salt after solvent evaporation. Then a 2 g Bond Elut SCX column was first rinsed with MeOH, load sample with MeOH, washed with MeOH dropwise to remove TFA, and finally rinsed with 2N NH3·MeOH to give the title compound as a free base. LC/MS: [(M+1)]+=377

Step F: 3-methyl-2-(5-oxo-2,5-dihydrofuran-3-yl)-2,8-diazaspiro[4.5]dec-3-en-1-one: To a solution of the compound of Step E (180 mg, 0.478 mmol) in THF (4.8 mL) at rt was added 10-ethyl-2,3,4,6,7,8,9,10-octahydropyrimido[1,2-a]azepine (polymer-bound, 1.15 mmol/g, 2.5 g resin). The reaction mixture was heated at 60° C. for 5 h on a shaker, then the resin was filtered off with a MeOH rinse, and the resulting mixture was evaporated to give the title compound. LCMS: [(M+1)]+=249

Intermediate 48

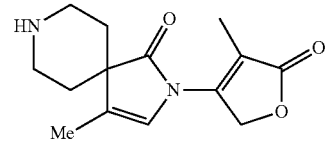 [SMILES: CC1=CN(C2=C(C)C(=O)OC2)C(=O)C12CCNCC2]

4-Methyl-2-(4-methyl-5-oxo-2,5-dihydrofuran-3-yl)-2,8-diazaspiro[4.5]dec-3-en-1-one Step A: tert-Butyl 2-(4-methyl-5-oxo-2,5-dihydrofuran-3-yl)-1,4-dioxo-2,8-diazaspiro[4.5]decane-8-carboxylate: To tert-butyl 4-hydroxy-2-(4-methyl-5-oxo-2,5-dihydrofuran-3-yl)-1-oxo-2,8-diazaspiro[4.5]decane-8-carboxylate (see example I-37A and I-37B, Step C, racemate prior to chiral HPLC separation)(200 mg, 0.546 mmol) in DCM (2.8 mL) was added sodium bicarbonate (68.8 mg, 0.819 mmol) and Dess-Martin periodinane (347 mg, 0.819 mmol). The reaction mixture was vigorously stirred for 1.5 h, then quenched with 10% Na2S2O3 and NaHCO3 aqueous solutions, and stirred for 20 min. The aqueous layer was extracted with DCM, and the organic layers were washed with brine, dried, and concentrated to give tert-butyl 2-(4-methyl-5-oxo-2,5-dihydrofuran-3-yl)-1,4-dioxo-2,8-diazaspiro[4.5]decane-8-carboxylate. LCMS: [(M+1)]+=365

Step B: tert-butyl 2-(4-methyl-5-oxo-2,5-dihydrofuran-3-yl)-1-oxo-4-(((trifluoromethyl)sulfonyl)oxy)-2,8-diazaspiro[4.5]dec-3-ene-8-carboxylate: To a flask containing tert-butyl 2-(4-methyl-5-oxo-2,5-dihydrofuran-3-yl)-1,4-dioxo-2,8-diazaspiro[4.5]decane-8-carboxylate (200 mg, 0.549 mmol) in THF (3 mL) was added NaHMDS (1.10 mL, 1 M in THF, 1.10 mmol) dropwise over 5 min at −78° C. The solution was stirred for 2 h, then N-phenylbis(trifluoromethanesulfonimide) (314 mg, 0.878 mmol) in THF (2 mL) was added dropwise over 5 min. The reaction mixture was stirred for 2 h at −78° C., then warmed to room temperature and stirred overnight. The reaction solution was quenched by the addition of saturated aq. NH$_4$Cl and extracted with EtOAc. The combined organic layers were dried (MgSO$_4$) and concentrated. The crude material was purified by column chromatography (0-10% MeOH/DCM) to afford the title compound. LC/MS: [(M+1)]$^+$=497

Step C: tert-butyl 4-methyl-2-(4-methyl-5-oxo-2,5-dihydrofuran-3-yl)-1-oxo-2,8-diazaspiro[4.5]dec-3-ene-8-carboxylate: tert-Butyl 2-(4-methyl-5-oxo-2,5-dihydrofuran-3-yl)-1-oxo-4-(((trifluoromethyl)sulfonyl)oxy)-2,8-diazaspiro[4.5]dec-3-ene-8-carboxylate (180 mg, 0.363 mmol) was dissolved in THF (3.6 mL), and Pd(Ph$_3$P)$_4$ (209 mg, 0.181 mmol) was added, followed by trimethylaluminum (3.6 mL, 7.25 mmol) at 0° C. This reaction was stirred at rt for 2 h before it was quenched with saturated aqueous NaHCO$_3$ solution at 0° C. (highly exothermic). This mixture was diluted with EtOAc, dried over Mg$_2$SO$_4$ and concentrated under reduced pressure. The crude material was purified by column chromatography (0-10% MeOH/DCM) to afford the title compound. LC/MS: [(M+1)]$^+$=363

Step D: 4-methyl-2-(4-methyl-5-oxo-2,5-dihydrofuran-3-yl)-2,8-diazaspiro[4.5]dec-3-en-1-one tert-Butyl 4-methyl-2-(4-methyl-5-oxo-2,5-dihydrofuran-3-yl)-1-oxo-2,8-diazaspiro[4.5]dec-3-ene-8-carboxylate (130 mg, 0.359 mmol) in DCM (1.8 mL) was treated with TFA (0.8 mL, 10.7 mmol) at 0° C. to remove the Boc group which provided the TFA salt. The TFA salt was loaded onto a 2 g Bond Elut SCX ion-exchange column with MeOH, then further washed with MeOH dropwise to remove TFA, and finally rinsed with 2 N NH$_3$MeOH to give the title compound as a free amine. LCMS: [(M+1)]$^+$=263

Intermediate 49

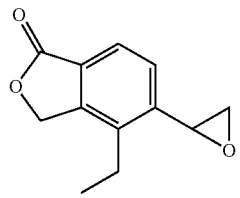

4-ethyl-5-oxiran-2-yl-2-benzofuran-1(3H)-one

Step A: 5-bromo-4-ethyl-2-benzofuran-1(3H)-one: A mixture of 5-bromo-4-vinyl-2-benzofuran-1(3H)-one (2.0 g, 8.37 mmol) and PdC (400 mg) in 50 mL of MeOH was stirred at rt. under H$_2$ (1 atm) overnight, and then filtered. The filtrate was concentrated. The resulting oil was purified by column chromatography to give 5-bromo-4-ethyl-2-benzofuran-1(3H)-one.

Step B: 4-ethyl-5-vinyl-2-benzofuran-1(3H)-one: A mixture of 5-bromo-4-ethyl-2-benzofuran-1(3H)-one (1.81 g, 7.51 mmol), potassium vinyltrifluoroborate (1.21 g, 9.01 mmol) and Pd(dppf)Cl$_2$ (200 mg) in 20 mL of TEA and 20 mL of EtOH was heated to reflux under N$_2$ overnight and then concentrated. The resulting material was purified by column chromatography to give 4-ethyl-5-vinyl-2-benzofuran-1(3H)-one.

Step C: 4-ethyl-5-oxiran-2-yl-2-benzofuran-1(3H)-one: To a solution of 4-ethyl-5-vinyl-2-benzofuran-1(3H)-one (1.1 g, 5.85 mmol) in 50 mL of DCM was slowly added mCPBA (3.60 g, 85% purity, 17.6 mmol) in 50 mL of DCM at 0° C. The mixture was warmed to room temperature, and then stirred for 3 days. The mixture was washed with aqueous Na$_2$SO$_3$ until KI paper didn't change color. The organic layers were combined, washed with brine and concentrated. The residue was purified by column chromatography to give 4-ethyl-5-oxiran-2-yl-2-benzofuran-1(3H)-one. $^1$H-NMR (400 MHz, CDCl$_3$) δ ppm 7.75 (d, J=8.6 Hz, 1H), 7.41 (d, J=7.8 Hz, 1H), 5.30 (s, 2H), 4.11-4.13 (m, 1H), 3.23-3.25 (m, 1H), 2.75-2.82 (m, 2H), 2.70-2.72 (m, 1H), 1.27 (t, J=7.4 Hz, 3H).

Intermediate 50

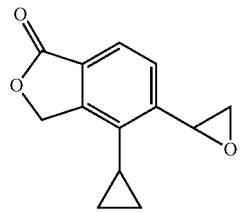 [SMILES: O=C1OCc2c1ccc(C1CO1)c2C1CC1]

4-cyclopropyl-5-oxiran-2-yl-2-benzofuran-1(3H)-one

Step A: 5-bromo-4-iodo-2-benzofuran-1(3H)-one: To a cooled (0° C.) solution of 5-bromo-2-benzofuran-1(3H)-one (50 g, 0.235 mol) in trifluoromethanesulfonic acid (400 mL) was added N-iodosuccinimide (55.5 g, 0.247 mol). The resulting mixture was stirred at room temperature overnight, then poured slowly into ice water (2 L), filtered and the filtrate extracted with EtOAc. The combined organic layers were washed with water and brine, dried and concentrated to give 5-bromo-4-iodo-2-benzofuran-1(3H)-one.

Step B: 5-bromo-4-vinyl-2-benzofuran-1(3H)-one: A mixture of 5-bromo-4-iodo-2-benzofuran-1(3H)-one (1 g, 2.95 mmol), potassium vinyltrifluoroborate (474 mg, 3.54 mmol) and Pd(dppf)Cl$_2$ (200 mg) in 20 mL of TEA and 20 mL of EtOH was heated to reflux under N$_2$ for 2 hours. TLC showed complete reaction. Most of the solvent was removed, and the residue was dissolved in EtOAc (100 mL). The solution was washed with 0.1 N HCl, sodium bicarbonate, and brine, dried over sodium sulfate, filtered and concentrated to provide 5-bromo-4-vinyl-2-benzofuran-1(3H)-one.

Step C: 5-bromo-4-cyclopropyl-2-benzofuran-1(3H)-one: To a cooled (0° C.) mixture of 5-bromo-4-vinyl-2-benzofuran-1(3H)-one (2.2 g, 9.21 mol) and Pd(OAc)$_2$ (100 mg) in EtOAc (50 mL) was added a solution of CH$_2$N$_2$ in ether (100 mL) slowly. The resulting mixture was stirred at room temperature overnight, then quenched with acetic acid, filtered and the filtrate washed with water and brine, dried and concentrated to provide title compound.

Step D: 4-cyclopropyl-5-vinyl-2-benzofuran-1(3H)-one: A mixture of 5-bromo-4-cyclopropyl-2-benzofuran-1(3H)-one (760 mg, 3.004 mmol), potassium vinyltrifluoroborate (805 mg, 6.01 mmol) and Pd(dppf)Cl$_2$ (100 mg) in 20 mL of TEA and 20 mL of EtOH was heated to reflux under $N_2$ for 8 hours. After TLC showed complete reaction, then most of the solvent was removed and the residue was dissolved in EtOAc (100 mL). The solution was washed with 0.1 N HCl, sodium bicarbonate, and brine, dried over sodium sulfate, filtered and concentrated. The resulting oil was purified by column chromatography to give the title compound.

Step E: 4-cyclopropyl-5-oxiran-2-yl-2-benzofuran-1(3H)-one: To a solution of 4-cyclopropyl-5-vinyl-2-benzofuran-1(3H)-one (440 mg, 2.2 mmol) in 50 mL of DCM was slowly added mCPBA (1.14 g, 6.6 mmol) in 50 mL of DCM at 0° C. After warming to room temperature, the mixture was stirred for 12 hours. The mixture was washed with aqueous $Na_2SO_3$ until KI paper didn't change color. The organic layers were combined, washed with brine and then concentrated. The residue was purified via prep-TLC to give the title compound. $^1$H-NMR (400 MHz, $CDCl_3$) δ ppm 7.77 (d, J=8.6 Hz, 1H), 7.39 (d, J=7.8 Hz, 1H), 5.39 (s, 2H), 4.43-4.45 (m, 1H), 3.26-3.28 (m, 1H), 2.68-2.70 (m, 1H), 1.94-2.01 (m, 1H), 1.08-1.12 (m, 2H), 0.65-0.75 (m, 2H).

Intermediate 51

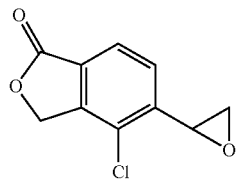 [SMILES: O=C1OCc2c1ccc(C1CO1)c2Cl]

4-chloro-5-oxiran-2-yl-2-benzofuran-1(3H)-one

Step A: 2-chloro-3-(hydroxymethyl)phenol: To a solution of 2-chloro-3-hydroxybenzaldehyde (8.10 g, 51.7 mmol) in MeOH was added $NaBH_4$ (1.96 g, 51.7 mmol) at 0° C. The reaction was allowed to stir for 30 minutes. The reaction was then diluted with EtOAc (400 mL), washed with water and brine, dried over sodium sulfate, and concentrated. The crude product was used in Step B without further purification.

Step B: 4-bromo-2-chloro-3-(hydroxymethyl)phenol: To a flask charged with 2-chloro-3-(hydroxymethyl)phenol and a stir bar was added NBS (10.8 g, 60.5 mmol) and TFA (50 mL). The reaction was allowed to stir for 16 hours at RT, then the solvent was removed under vacuum. The residue was re-dissolved in EtOAc, washed with water, and purified by silica gel flash chromatography. A pair of regio-isomers was collected from the separation. The less polar spot was the desired 4-bromo-2-chloro-3-(hydroxymethyl)phenol according to NMR analysis.

Step C: 4-chloro-5-hydroxy-2-benzofuran-1(3H)-one: To a flask charged with 4-bromo-2-chloro-3-(hydroxymethyl)phenol (2.44 g, 10.3 mmol) and a stir bar, was added CuCN (2.76 g, 30.8 mmol) and DMF (25 mL). The flask was fitted with a condenser and purged three times with Nitrogen. he solution was then heated to 145° C. for 2 hours. At that point, water (0.555 mL, 30.8 mmol) was added to the reaction via a syringe, and the reaction was kept at 100° C. for another 24 hours. The reaction was cooled to RT, diluted with DCM (100 mL), and filtered through a pad of CELITE® to remove the solids. The filtrate was washed with saturated $NH_4OAc$, dried over sodium sulfate, concentrated and purified by silica gel flash chromatography to afford title compound.

Step D: 4-chloro-5-ethenyl-2-benzofuran-1(3H)-one: To a cold solution of 4-chloro-5-hydroxy-2-benzofuran-1(3H)-one (1.39 g, 7.53 mmol) in DCM (25 mL) was added Hunig's Base (3.29 mL, 18.8 mmol) and trifluoromethanesulfonic anhydride (2.54 mL, 15.1 mmol). The mixture was allowed to stir for 16 hours. Analysis by TLC showed complete consumption of all SM. The reaction was diluted with hexane and washed with water. The solution was dried with sodium sulfate, concentrated, and purified by flash chromatography on a silica column. The solvent was removed under reduced pressure to give intermediate triflate. LC-MS (M+1=317). To the triflate was added a stir bar, potassium vinyltrifluoroborate (1.33 g, 9.90 mmol), $PdCl_2(dppf)$ (0.243 g, 0.332 mmol), triethylamine (1.89 mL, 13.3 mmol), and iso-propanol (50 mL). The mixture was purged three times with nitrogen, and heated to 60° C. for 2 hours. TLC showed complete reaction at that point. Most of the solvent was removed under vacuum. The crude residue was diluted with EtOAc (200 mL), washed with brine, dried over sodium sulfate, adsorbed onto silica gel, and purified by flash chromatography to give the title compound.

Step E: 4-chloro-5-oxiran-2-yl-2-benzofuran-1(3H)-one: To a solution of 4-chloro-5-ethenyl-2-benzofuran-1(3H)-one (1.1 g, 5.7 mmol) in DCM (40 mL) was added mCPBA (1.9 g, 8.5 mmol). The solution was allowed to stir at RT for 16 hours. Analysis by TLC and LC showed formation of the desired product. The reaction was diluted with DCM (200 mL), washed with aqueous $Na_2S_2O_3$ and $Na_2CO_3$, dried over sodium sulfate, concentrated, and purified by silica gel flash chromatography to afford title compound. $^1$H-NMR (500 MHz, $CDCl_3$) δ ppm 7.86 (d, J=8.0 Hz, 1H), 7.48 (d, J=8.0 Hz, 1H), 5.34 (s, 2H), 4.33 (m, 1H), 3.33 (m, 1H), 2.75 (m, 1H).

Intermediate 52

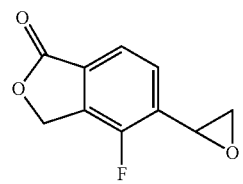 [SMILES: O=C1OCc2c1ccc(C1CO1)c2F]

4-Fluoro-5-oxiran-2-yl-2-benzofuran-1(3H)-one

Step A: 5-Bromo-4-fluoro-2-benzofuran-1(3H)-one: A solution of n-BuLi (40 mL, 100 mmol) was added dropwise to a solution of diisopropylamine (10.6 g, 105 mmol) in 150 mL of THF at −70° C. The mixture was stirred at 0° C. for 15 minutes and then cooled to −70° C. again. A solution of 4-bromo-3-fluorobenzoic acid (10 g, 45.7 mmol, in 50 mL of THF) was added dropwise. The resulting mixture was stirred at −70° C. for 1 hour then $CH_2O$ gas (generated by heating 5.1 g of Para formaldehyde to 200° C.) was bubbled into the mixture. The resulting mixture was stirred at −70° C. for 1 hour then allowed to warm to room temperature and stirred for another 2 hours. HCl gas was bubbled into the suspension for 15 minutes to give a solution. The mixture was diluted with 1 L of EtOAc and washed subsequently with water, saturated $Na_2CO_3$ and brine, dried over anhydrous $Na_2SO_4$ and concentrated to give 5-bromo-4-fluoro-2-benzofuran-1(3H)-one. $^1$H-NMR (400 MHz, $CDCl_3$) δ ppm 7.72-7.75 (m, 1H), 7.58 (d, J=8.0 Hz, 1H), 5.36 (s, 2H).

Step B: 4-fluoro-5-vinyl-3H-isobenzofuran-1-one: A mixture of 5-bromo-4-fluoro-2-benzofuran-1(3H)-one (5.0 g, 21.6 mmol), potassium vinyltrifluoroborate (4.4 g, 32.5 mmol) and Pd(dppf)Cl$_2$ (500 mg) in 100 mL of TEA and 100 mL of EtOH was heated to reflux under N$_2$ for 4 hrs and then concentrated. The resulting oil was purified by column chromatography to give 4-fluoro-5-vinyl-3H-isobenzofuran-1-one. $^1$H-NMR (400 MHz, CDCl$_3$) δ ppm 7.67-7.68 (m, 2H), 6.90-6.97 (m, 1H), 6.00 (d, J=17.2 Hz, 1H), 5.60 (d, J=11.0 Hz, 1H), 5.35 (s, 2H).

Step C: 4-fluoro-5-oxiranyl-3H-isobenzofuran-1-one: To a solution of 4-fluoro-5-vinyl-3H-isobenzofuran-1-one (4.0 g, 17.3 mmol) in 100 mL of DCM was slowly added mCPBA (6.0 g, 85% purity, 34.6 mmol) in 50 mL of DCM at 0° C. After warming to room temperature, the mixture was stirred overnight. The mixture was washed with aqueous Na$_2$SO$_3$ until KI paper didn't change color. The organic layers were washed with brine and then concentrated. The residue was purified by column chromatography to give 4-fluoro-5-oxiranyl-3H-isobenzofuran-1-one. $^1$H-NMR (400 MHz, CDCl$_3$) δ ppm 7.71 (d, J=7.8 Hz, 1H), 7.37-7.40 (m, 1H), 5.37 (s, 2H), 4.21-4.22 (m, 1H), 3.25-3.27 (m, 1H), 2.80-2.82 (m, 1H).

Intermediate 53

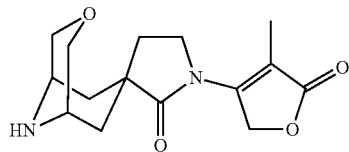 [SMILES: CC1=C(N2CCC3(CC4COCC(C3)N4)C2=O)COC1=O]

(1R,3'r,5S)-1'-(4-methyl-5-oxo-2,5-dihydrofuran-3-yl)-3-oxa-9-azaspiro[bicyclo[3.3.1]nonane-7,3'-pyrrolidin]-2'-one Step A: (1R,5S,E)-tert-butyl 7-(1-cyano-2-methoxy-2-oxoethylidene)-3-oxa-9-azabicyclo[3.3.1]nonane-9-carboxylate: A solution of methyl 2-cyanoacetate (4.39 mL, 49.7 mmol), (1R,5S)-tert-butyl 7-oxo-3-oxa-9-azabicyclo[3.3.1]nonane-9-carboxylate (8 g, 33.2 mmol), ammonium acetate (3.83 g, 49.7 mmol), and acetic acid (7.59 ml, 133 mmol) in toluene (100 ml) was heated at 150° C. overnight and the water generated was separated by Dean-Stark trap. After evaporating the solvent the residue was dissolved in ethyl acetate (200 mL) and the solution was washed with saturated sodium bicarbonate, dried over sodium sulfate, concentrated and the residue was purified on silica gel column using ethyl acetatehexane as eluting solvents to give the title compound. LCMS: (M+1-100)$^+$: 223.01.

Step B: (1R,5S,7s)-tert-butyl 7-(1-cyano-2-methoxy-2-oxoethyl)-7-vinyl-3-oxa-9-azabicyclo[3.3.1]nonane-9-carboxylate: To a suspension of (1R,5S,E)-tert-butyl 7-(1-cyano-2-methoxy-2-oxoethylidene)-3-oxa-9-azabicyclo[3.3.1]nonane-9-carboxylate (10.82 g, 33.6 mmol) and copper(I) iodide (6.39 g, 33.6 mmol) in tetrahydrofuran at 0° C. was added vinylmagnesium bromide (50.3 ml, 50.3 mmol) slowly over 2 h. The resulting mixture was stirred from 0° C. to rt for 2 h. The reaction was quenched by saturated ammonium chloride (300 mL), the mixture was extracted with ethyl acetate three times, the combined organic phase was dried over sodium sulfate then concentrated, and the residue was purified on silica gel using ethyl acetatehexane as eluting solvents to give the title compound. LCMS: (M+23)$^+$: 372.94.

Step C: 2-((1R,5S,7s)-9-(tert-butoxycarbonyl)-7-vinyl-3-oxa-9-azabicyclo[3.3.1]nonan-7-yl)-2-cyanoacetic acid: To a solution of (1R,5S,7s)-tert-butyl 7-(1-cyano-2-methoxy-2-oxoethyl)-7-vinyl-3-oxa-9-azabicyclo[3.3.1]nonane-9-carboxylate (1.3 g, 3.7 mmol) in a mixture of tetrahydrofuran (10 ml), methanol (3 ml) and water (3 ml) was added lithium hydroxide (18.55 ml, 18.55 mmol). The resulting solution was stirred at rt for 2 h. After removing the volatiles the alkaline phase was acidified at 0° C. with 1N HCl to pH 4. The mixture was then extracted with 30% isopropanol/methylene chloride (3×100 mL), and the combined organic phase was dried over sodium sulfate and concentrated to give the title compound. LCMS: (M-100+1)$^+$: 237.04.

Step D: (1R,5S,7r)-tert-butyl 7-(cyanomethyl)-7-vinyl-3-oxa-9-azabicyclo[3.3.1]nonane-9-carboxylate: A solution of 2-((1R,5S,7s)-9-(tert-butoxycarbonyl)-7-vinyl-3-oxa-9-azabicyclo[3.3.1]nonan-7-yl)-2-cyanoacetic acid (1.10 g, 3.27 mmol) in DMF (10 mL) was heated at 130° C. for 20 min. After cooling to rt the reaction mixture was partitioned between ethyl acetate (200 mL) and brine, the organic phase was washed with brine three time, dried over sodium sulfate then concentrated, and the residue was purified on silica gel column using ethyl acetate/hexane as eluting solvents to give the title compound. LCMS: (M-100+1)$^+$: 193.08.

Step E: (1R,5S,7r)-tert-butyl 7-(cyanomethyl)-7-formyl-3-oxa-9-azabicyclo[3.3.1]nonane-9-carboxylate: To a solution of (1R,5S,7r)-tert-butyl 7-(cyanomethyl)-7-vinyl-3-oxa-9-azabicyclo[3.3.1]nonane-9-carboxylate (0.66 g, 2.257 mmol) in dioxane (10 ml) and water (3 ml) was added sodium periodiate (1.931 g, 9.03 mmol) and osmium tetroxide (0.035 ml, 0.113 mmol). The resulting mixture was stirred at rt overnight. Next, thiosulphate (2 g) was added and the mixture was stirred at rt for 0.5 h. The reaction mixture was filtered and the filtrate was partitioned between methylene chloride and saturated sodium bicarbonate, and the alkaline phase was extracted with methylene chloride (3×100 mL). The combined organic phase was dried over sodium sulfate and concentrated to give the title compound. LCMS: (M-100+1)$^+$: 195.09.

Step F: (1R,5S,7r)-9-(tert-butoxycarbonyl)-7-(cyanomethyl)-3-oxa-9-azabicyclo[3.3.1]nonane-7-carboxylic acid: To a solution of (1R,5S,7r)-tert-butyl 7-(cyanomethyl)-7-formyl-3-oxa-9-azabicyclo[3.3.1]nonane-9-carboxylate (613 mg, 2.083 mmol) in tert-BuOH (10 ml) and water (5 ml) was added sodium dihydrogen phosphate (750 mg, 6.25 mmol) and 2-methyl-2 butene (1.098 ml, 10.41 mmol). The solution was cooled to 0° C. and sodium chlorite (565 mg, 6.25 mmol) was added by portions. The reaction solution was stirred at 0° C. for 1 h. Additional sodium dihydrogen phosphate (750 mg, 6.25 mmol), 2-methyl-2 butene (1.098 ml, 10.41 mmol) and sodium chlorite (565 mg, 6.25 mmol) was added. The reaction mixture was left to stir at 0° C. for 2 h before being quenched by addition of 1 N HCl to pH 4. Next, the mixture was diluted in water (100 mL) and was extracted with methylene chloride (3×100 mL) while maintaining pH 4 by 1 N HCl. The combined organic phase was dried over sodium sulfate and concentrated to give the title compound. LCMS: (M+23)$^+$: 333.03.

Step G: (1R,5S,7r)-9-tert-butyl 7-methyl 7-(cyanomethyl)-3-oxa-9-azabicyclo[3.3.1]nonane-7,9-dicarboxylate: To a solution of (1R,5S,7r)-9-(tert-butoxycarbonyl)-7-(cyanomethyl)-3-oxa-9-azabicyclo[3.3.1]nonane-7-carboxylic acid (646 mg, 2.082 mmol) in methanol (10 ml) was added TMS-diazomethane (5.20 ml, 10.41 mmol) dropwise until there was no bubble generation, and then the reaction was quenched by addition of acetic acid (a few drops). The mixture was concentrated to give the title compound. LC/MS: (M+23)⁺: 346.98.

Step H: (1R,5S,7r)-9-tert-butyl 7-methyl 7-(2-aminoethyl)-3-oxa-9-azabicyclo[3.3.1]nonane-7,9-dicarboxylate: A mixture of (1R,5S,7r)-9-tert-butyl 7-methyl 7-(cyanomethyl)-3-oxa-9-azabicyclo[3.3.1]nonane-7,9-dicarboxylate (0.58 g, 1.788 mmol) and platinum(IV) oxide (0.082 g, 0.358 mmol) in methanol (10 ml) and acetic acid (10 ml) was hydrogenated at 45 Psi over the weekend. After filtration through CELITE® under nitrogen, the filtrate was concentrated to give the title compound. LC/MS: (M+1)⁺: 329.04.

Step I: (1R,3'r,5S)-tert-butyl 2'-oxo-3-oxa-9-azaspiro[bicyclo[3.3.1]nonane-7,3'-pyrrolidine]-9-carboxylate: A mixture of (1R,5S,7r)-9-tert-butyl 7-methyl 7-(2-aminoethyl)-3-oxa-9-azabicyclo[3.3.1]nonane-7,9-dicarboxylate (0.59 g, 1.797 mmol) and potassium carbonate (1.490 g, 10.78 mmol) in methanol (50 ml) was heated at reflux for 4 h. After evaporating the solvent, the residue was partitioned between methylene chloride and water, and the aqueous phase was extracted with methylene five times. The combined organic phase was dried over sodium sulfate and concentrated to give the title compound. LCMS: (M+23)⁺: 319.03.

Step J: (1R,3'r,5S)-tert-butyl 1'-(4-methyl-5-oxo-2,5-dihydrofuran-3-yl)-2'-oxo-3-oxa-9-azaspiro[bicyclo[3.3.1]nonane-7,3'-pyrrolidine]-9-carboxylate: To a mixture of (1R,3'r,5S)-tert-butyl 2'-oxo-3-oxa-9-azaspiro[bicyclo[3.3.1]nonane-7,3'-pyrrolidine]-9-carboxylate (0.42 g, 1.417 mmol) and 4-methyl-5-oxo-2,5-dihydrofuran-3-yl trifluoromethanesulfonate (0.454 g, 1.842 mmol) in toluene (15 ml) was added potassium carbonate (0.588 g, 4.25 mmol), xantphos (0.328 g, 0.567 mmol), and water (0.077 ml, 4.25 mmol). The mixture was flushed with nitrogen for 20 min before addition of palladium (II) acetate (0.064 g, 0.283 mmol). The resulting mixture was heated at 70° C. overnight. After filtration the residue was purified on silica gel column using ethyl acetatehexane to give the title compound. LC/MS: (M+1)⁺: 393.24.

Step K: (1R,3'r,5S)-1'-(4-methyl-5-oxo-2,5-dihydrofuran-3-yl)-3-oxa-9-azaspiro[bicyclo[3.3.1]nonane-7,3'-pyrrolidin]-2'-one: To a solution of (1R,3'r,5S)-tert-butyl 1'-(4-methyl-5-oxo-2,5-dihydrofuran-3-yl)-2'-oxo-3-oxa-9-azaspiro[bicyclo[3.3.1]nonane-7,3'-pyrrolidine]-9-carboxylate (0.22 g, 0.561 mmol) in methylene chloride (4 mL) was added trifluororoacetic acid (4 ml, 51.9 mmol), and the resulting solution was stirred at rt for 2 h. After removing the volatiles the residue was basified on an ion exchange column washing with methanol followed by eluting with 1N ammonia in methanol to give the title compound. LC/MS: (M+1)⁺: 293.21.

Intermediate 54

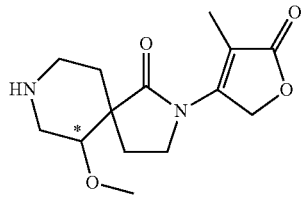 [SMILES: COC1CNCCC12CCN(C1=C(C)C(=O)OC1)C2=O]

6-methoxy-2-(4-methyl-5-oxo-2,5-dihydrofuran-3-yl)-2,8-diazaspiro[4.5]decan-1-one (CIS, Faster)

Step A: ethyl 1-benzyl-4-(cyanomethyl)-3-oxopiperidine-4-carboxylate: Into a 250-mL 3-necked round-bottom flask was placed a solution of ethyl 1-benzyl-3-oxopiperidine-4-carboxylate (10 g, 38.27 mmol, 1.00 equiv) in tetrahydrofuran (80 mL). This was followed by the addition of a solution of KHMDS in tetrahydrofuran (42 mL, 1M) dropwise with stirring at 0° C., and 30 min later, 2-bromoacetonitrile (6.89 g, 57.44 mmol, 1.50 equiv) was added dropwise with stirring at 0° C. The resulting solution was stirred for 4 h at room temperature. The resulting mixture was concentrated under vacuum. The residue was applied onto a silica gel column and eluted with ethyl acetate/petroleum ether to give the title compound.

Step B: ethyl 4-(2-aminoethyl)-1-benzyl-3-hydroxypiperidine-4-carboxylate: Into a 10000-mL 4-necked round-bottom flask was placed a solution of ethyl 1-benzyl-4-(cyanomethyl)-3-oxopiperidine-4-carboxylate (180 g, 599.30 mmol) in acetic acid/methanol (1:1, 5.4 L) and platinum oxide (27 g, 118.90 mmol). The flask was then flushed and charged with hydrogen and stirred overnight at room temperature. After filtration under nitrogen through CELITE®, the filtrate was concentrated under vacuum to give the title compound.

Step C: 8-benzyl-6-hydroxy-2,8-diazaspiro[4.5]decan-1-one: Into a 10000-mL 3-necked round-bottom flask was placed a solution of ethyl 4-(2-aminoethyl)-1-benzyl-3-hydroxypiperidine-4-carboxylate (220 g, 718.02 mmol, 1.00 equiv) in methanol (2000 mL) and ammonia (2000 mL). The resulting solution was stirred overnight at 45° C. The resulting mixture was concentrated under vacuum. The residue was applied onto a silica gel column and eluted with dichloromethane/methanol to obtain the title compound.

Step D: cis-tert-butyl 6-hydroxy-2-(4-methyl-5-oxo-2,5-dihydrofuran-3-yl)-1-oxo-2,8-diazaspiro[4.5]decane-8-carboxylate: Into a 2000-mL 3-necked round-bottom flask purged and maintained with an inert atmosphere of nitrogen was placed a solution of 8-benzyl-6-hydroxy-2,8-diazaspiro[4.5]decan-1-one (46.3 g, 177.85 mmol, 1.00 equiv), Cs₂CO₃ (115.9 g, 354.62 mmol, 1.99 equiv), Xantphos (6.17 g, 10.66 mmol, 0.06 equiv), Pd₂(dba)₃ (5.52 g, 6.03 mmol, 0.03 equiv) and 4-methyl-5-oxo-2,5-dihydrofuran-3-yl trifluoromethanesulfonate (56.92 g, 231.23 mmol, 1.30 equiv) in dioxane (900 mL). The resulting solution was stirred overnight at 80° C. The resulting mixture was cooled and concentrated under vacuum. The residue was diluted with 1000 mL of water, then extracted with ethyl acetate. The organic layers were combined, washed with 1000 mL of water and 1000 mL of brine, dried over anhydrous sodium sulfate and concentrated under vacuum. The residue was applied onto a silica gel column and eluted with ethyl acetate to give of trans-tert-butyl 6-hydroxy-2-(4-methyl-5-oxo-2,5-dihydrofuran-3-yl)-1-oxo-2,8-diazaspiro[4.5]decane-8-carboxylate, LC/MS: (M+1)⁺: 357; ¹H-NMR (300 MHz, CDCl₃, ppm): δ 7.33-7.26 (5H, m), 5.27-5.25 (2H, m), 4.04-3.96 (2H, m), 3.75-3.72 (1H, m), 3.58 (2H, d, J=2.4 Hz), 2.88-2.75 (3H, m), 2.55-2.50 (1H, m), 2.40-2.12 (3H, m), 2.09-2.00 (4H, m), 1.57-1.55 (1H, m). and cis-tert-butyl 6-hydroxy-2-(4-methyl-5-oxo-2,5-dihydrofuran-3-yl)-1-oxo-2,8-diazaspiro[4.5]decane-8-carboxylate. LC/MS: (M+1)⁺: 357; ¹H-NMR (300 MHz, CDCl₃, ppm): δ 7.33-7.26 (5H, m), 5.27-5.25 (2H, m), 4.06-3.94 (3H, m), 3.61-3.50 (2H, m), 2.93-2.81 (1H, m), 2.79-2.74 (1H, m), 2.57-2.48 (1H, m), 2.19-2.12 (2H, m), 2.03-2.02 (3H, m), 1.97-1.85 (2H, m), 1.68-1.58 (2H, m).

Step D: tert-butyl 6-hydroxy-2-(4-methyl-5-oxo-2,5-dihydrofuran-3-yl)-1-oxo-2,8-diazaspiro[4.5]decane-8-carboxylate (CIS): To a solution of 8-benzyl-6-hydroxy-2-(2-methyl-3-oxocyclopent-1-en-1-yl)-2,8-diazaspiro[4.5]decan-1-one (CIS) (10 g, 28.2 mmol) and di-tert-butylcarbonate (7.21 ml, 31.0 mmol) in methanol (50 ml) was added palladium on carbon (1.501 g, 1.411 mmol), and the resulting mixture was subjected to hydrogenation at 45 Psi at rt over the weekend. The suspension was filtered through CELITE® under nitrogen, the filtrate was concentrated and the residue was purified on silica gel using ethyl acetatehexane as eluting solvents to give the title compound. LC/MS: (M+1)+: 367.17.

Step E: tert-butyl 6-methoxy-2-(4-methyl-5-oxo-2,5-dihydrofuran-3-yl)-1-oxo-2,8-diazaspiro[4.5]decane-8-carboxylate (CIS, faster) and tert-butyl 6-methoxy-2-(4-methyl-5-oxo-2,5-dihydrofuran-3-yl)-1-oxo-2,8-diazaspiro[4.5]decane-8-carboxylate (CIS, slower): To the mixture of tert-butyl 6-hydroxy-2-(4-methyl-5-oxo-2,5-dihydrofuran-3-yl)-1-oxo-2,8-diazaspiro[4.5]decane-8-carboxylate (CIS) (2 g, 5.46 mmol) and silver oxide (1.391 g, 6.00 mmol) in acetonitrile (50 mL) was added methyl iodide (3.41 ml, 54.6 mmol). The mixture was heated at 60° C. in a sealed tube overnight. After it cooled to rt, the mixture was filtered and the filtrate was concentrated and the residue was purified by silica gel chromatography using ethyl acetatehexane to give tert-butyl 6-methoxy-2-(4-methyl-5-oxo-2,5-dihydrofuran-3-yl)-1-oxo-2,8-diazaspiro[4.5]decane-8-carboxylate (CIS, racemate). LC/MS: (M+1)+: 380.99. The racemate was further separated on an AD chiral column give tert-butyl 6-methoxy-2-(4-methyl-5-oxo-2,5-dihydrofuran-3-yl)-1-oxo-2,8-diazaspiro[4.5]decane-8-carboxylate (faster eluting, CIS), LC/MS: (M+1)+: 381.05, and tert-butyl 6-methoxy-2-(4-methyl-5-oxo-2,5-dihydrofuran-3-yl)-1-oxo-2,8-diazaspiro[4.5]decane-8-carboxylate (slower eluting, CIS). LC/MS: (M+1)+: 381.01.

Step F: 6-methoxy-2-(4-methyl-5-oxo-2,5-dihydrofuran-3-yl)-2,8-diazaspiro[4.5]decan-1-one (CIS, faster): To a solution of tert-butyl 6-methoxy-2-(4-methyl-5-oxo-2,5-dihydrofuran-3-yl)-1-oxo-2,8-diazaspiro[4.5]decane-8-carboxylate (CIS, faster) (2.17 g, 5.70 mmol) in methylene chloride (7 mL) was added trifluoroacetic (7 mL, 91 mmol) and the resulting solution was stirred at rt for 2 h. After concentration the residue was basified on ion exchange column washing with methanol first, then eluted with 1 N ammonia in methanol to give 6-methoxy-2-(4-methyl-5-oxo-2,5-dihydrofuran-3-yl)-2,8-diazaspiro[4.5]decan-1-one (CIS, faster). LC/MS: (M+1)+: 281.11.

In the following Examples and above Intermediates, isomer "A" and isomer "B," (e.g., Isomer 6A and 6B, and the like), refer to the faster eluting and slower eluting diastereomers, respectively, based on the observed elution order of the individual diastereomers upon separation from its isomer mixture. Except for a defined chiral center in the parent isomer mixture, absolute stereochemistry of each of the separated isomers was not determined unless stated otherwise.

In examples where absolute stereochemistry of each of the separated isomers was not determined, an asterisk (*) may be used in the associated chemical structure drawing that indicates the location of the unassigned chiral center.

EXAMPLE 1

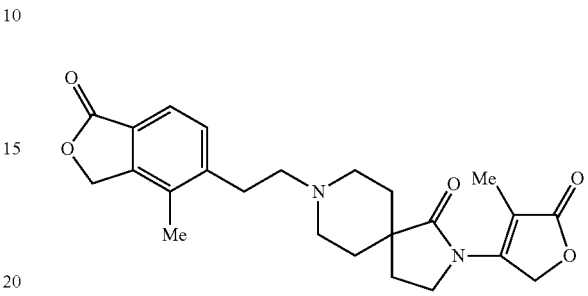

8-(2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one A mixture of (4-Methyl-1-oxo-1,3-dihydro-2-benzofuran-5-yl)acetaldehyde (I-3) (100 mg, crude) and 2-(4-methyl-5-oxo-2,5-dihydrofuran-3-yl)-2,8-diazaspiro[4.5]decan-1-one (I-16) (145 mg, 0.58 mmol) in THF (5 mL) was stirred at rt for 2 hours and then NaBH(OAc)₃ (167 mg, 0.79 mmol) was added to the mixture, which was further stirred at 50° C. for 3 hours. After quenching with saturated NH₄Cl aq, the mixture was extracted with EtOAc and organic layer was dried over Na₂SO₄. Solvent was removed under reduced pressure and the residue was purified by prep-TLC (EtOAc/MeOH: 1/1) and prep-HPLC to give the title product. MS (ESI) m/z: 425 (M+H+); ¹H NMR (400 MHz, MeOD): δ 7.69 (d, J=7.6 Hz, 1H), 7.50 (d, J=7.6 Hz, 1H), 5.38 (s, 2H), 5.27-5.25 (m, 2H), 4.20-4.14 (m, 2H), 3.83-3.80 (m, 1H), 3.68-3.66 (m, 1H), 3.42-3.38 (m, 2H), 3.33-3.23 (m, 4H), 2.41 (s, 3H), 2.39-2.30 (m, 2H), 2.24-2.17 (m, 2H), 2.10-2.03 (m, 5H).

The following compounds in Table 1 were prepared in an analogous fashion to EXAMPLE 1 starting from piperidine and aldehyde intermediates prepared as described above.

TABLE 1

| Example | Intermediates | EXAMPLE STRUCTURE/NAME | Characterization |
|---|---|---|---|
| 2 | 5, 22A | (S)-8-((R)-2-methoxy-2-(4-methyl-1-oxo-1,3-dihydroisobenzofuran-5-yl)ethyl)-3-methyl-2-(5-oxo-2,5-dihydrofuran-3-yl)-2,8-diazaspiro[4,5]decan-1-one | LC/MS, (M + 1)+: 455 |

TABLE 1-continued

| Example | Intermediates | EXAMPLE STRUCTURE/NAME | Characterization |
|---|---|---|---|
| 3 | 1, 16 | 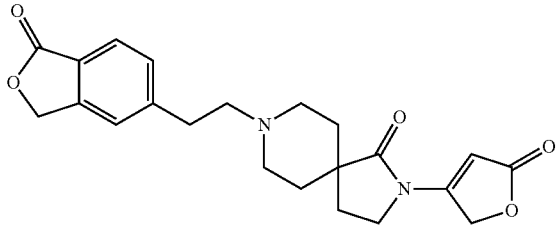<br>8-[2-(1-oxo-1,3-dihydro-2-benzofuran-5-yl)ethyl]-2-(5-oxo-2,5-dihydrofuran-3-yl)-2,8-diazaspiro[4.5]decan-1-one | LC/MS, $(M + 1)^+$: 397 |
| 4 | 3, 22A | 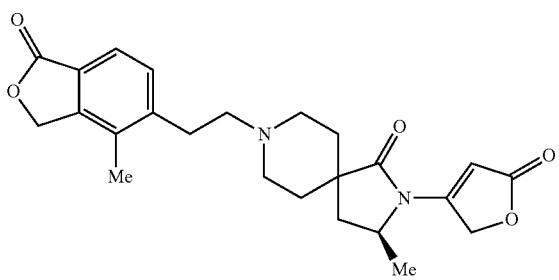<br>(S)-3-methyl-8-(2-(4-methyl-1-oxo-1,3-dihydroisobenzofuran-5-yl)ethyl)-2-(5-oxo-2,5-dihydrofuran-3-yl)-2,8-diazaspiro[4.5]decan-1-one | LC/MS, $(M + 1)^+$: 425 |

EXAMPLE 5

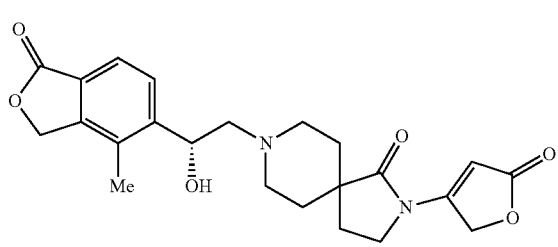 [SMILES: Cc1c([C@@H](O)CN2CCC3(CC2)CCN(C2=CC(=O)OC2)C3=O)ccc2c1COC2=O]

8-[(2R)-2-hydroxy-2-(4-methyl-1-oxo-1,3-dihydro-2-benzofuran-5-yl)ethyl]-2-(5-oxo-2,5-dihydrofuran-3-yl)-2,8-diazaspiro[4.5]decan-1-one: 2-(5-oxo-2,5-dihydrofuran-3-yl)-2,8-diazaspiro[4.5]decan-1-one (I-16, 200 mg, 0.846 mmol) was combined with 4-methyl-5-[(2R)-oxiran-2-yl]-2-benzofuran-1(3H)-one (I-4B) (177 mg, 0.931 mmol) in ethanol (5 mL) and heated in a microwave apparatus at 145° C. for 3 hours. The solvent was removed and the residue was purified by preparative TLC, eluting with 25% methanol/EtOAc to afford the title compound. LC-MS (IE, m/z): 427 (M+1)$^+$.

EXAMPLE 6

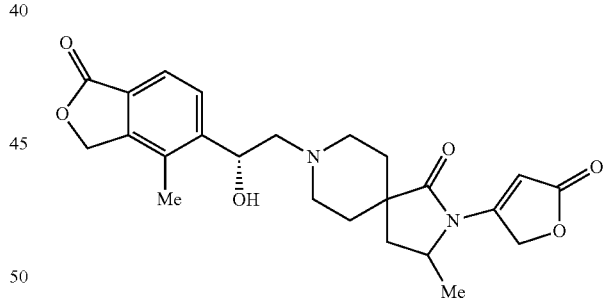

8-((R)-2-Hydroxy-2-(4-methyl-1-oxo-1,3-dihydroisobenzofuran-5-yl)ethyl)-3-methyl-2-(5-oxo-2,5-dihydrofuran-3-yl)-2,8-diazaspiro[4.5]decan-1-one 3-Methyl-2-(5-oxo-2,5-dihydrofuran-3-yl)-2,8-diazaspiro[4.5]decan-1-one (I-22, 0.257 mmol) was dissolved in ethanol (3 mL), and treated with diisopropylethylamine (135 µA, 0.771 mmol) followed by (R)-4-methyl-5-(oxiran-2-yl)isobenzofuran-1(3H)-one (I-4B, 73.3 mg, 0.385 mmol). The mixture was heated at 80° C. in a sealed tube for 12 hours. The reaction mixture was then cooled to room temperature and concentrated. The resulting crude product was purified by column chromatography eluting with a 0-20% MeOH/EtOAc gradient to give the title product as a mixture of diastereomers. LC-MS (IE, m/z): 441.3 (M+1)$^+$.

EXAMPLE 6A and 6B (Separated Single Isomers)

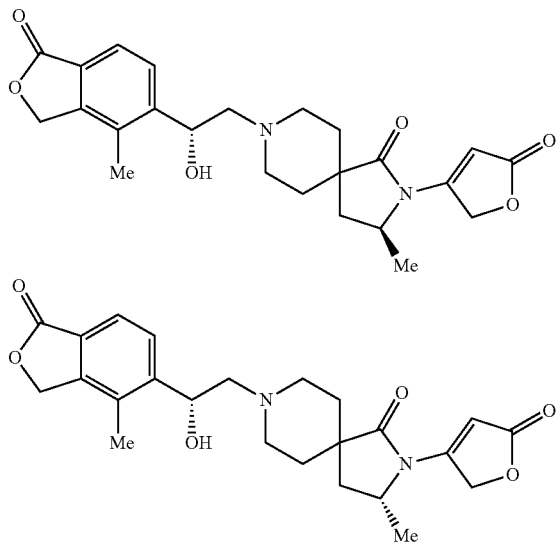

(R)-8-((R)-2-hydroxy-2-(4-methyl-1-oxo-1,3-dihydroisobenzofuran-5-yl)ethyl)-3-methyl-2-(5-oxo-2,5-dihydrofuran-3-yl)-2,8-diazaspiro[4.5]decan-1-one; and
(S)-8-((R)-2-Hydroxy-2-(4-methyl-1-oxo-1,3-dihydroisobenzofuran-5-yl)ethyl)-3-methyl-2-(5-oxo-2,5-dihydrofuran-3-yl)-2,8-diazaspiro[4.5]decan-1-one (separated isomers A and B):

The product of Example 6 was resolved using SFC eluting with 30% MeOH (0.2% DEA)/CO₂ on Chiralcel OD column to give Isomer 6A (faster eluting): LC-MS (IE, m/z): 441.3; and Isomer 6B (slower eluting): LC-MS (IE, m/z): 441.3 (M+1)⁺.

EXAMPLE 7

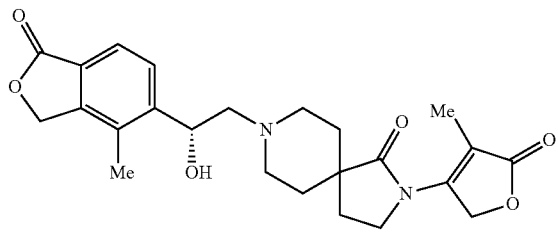 [SMILES: CC1=C(N2CCC3(CCN(C[C@H](O)c4ccc5c(c4C)COC5=O)CC3)C2=O)COC1=O]

8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one: A solution of 2-(4-methyl-5-oxo-2,5-dihydrofuran-3-yl)-2,8-diazaspiro[4.5]decan-1-one (I-17, 6.00 g, 24.0 mmol) and 4-methyl-5-[(2R)-oxiran-2-yl]-2-benzofuran-1(3H)-one (I-4B, 5.93 g, 31.2 mmol) in ethanol (20 mL) in a sealed tube was heated at 95° C. overnight. After concentration, the residue was purified on silica gel column using methanol/dichloromethane, then precipitated from methanol to give the title compound. LC/MS, (M+1)⁺: 440.93. ¹HNMR (500 MHz, CDCl₃), δ7.845-7.809(m, 2H), 5.290-5.278(m, 4H), 5.139-5.112(m, 1H), 4.072-4.044(t, J=7.1 Hz, 2H), 3.190-3.167(m, 1H), 2.876-2.859(m, 1H), 2.636-2.604(m, 2H), 2.468-2.421(m, 1H), 2.311 (s, 3H), 2.350-2.328 (m, 1H), 2.193-2.165(t, J=7.1 Hz, 2H), 2.101-2.039(m, 5H), 1.668-1.618(m, 2H).

EXAMPLE 8

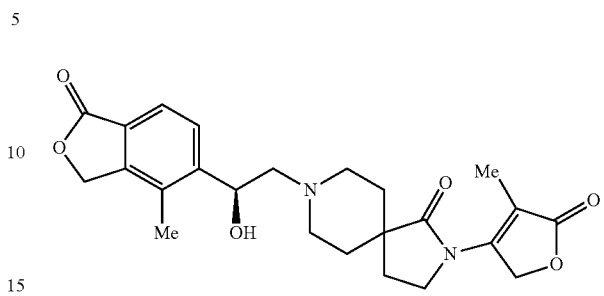

8-[(2S)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one: To a solution of 2-(4-methyl-5-oxo-2,5-dihydrofuran-3-yl)-2,8-diazaspiro[4.5]decan-1-one (I-17, 10 mg, 0.040 mmol) in ethanol (2 mL) in a microwave tube was added (S)-4-methyl-5-(oxiran-2-yl)isobenzofuran-1(3H)-one (I-4A, 9.9 mg, 0.052 mmol)) and the resulting solution was heated at 140° C. in microwave for 3 h. After concentration, the residue was purified by preparative TLC using 30% methanol/ethyl acetate to give the title compound. LC/MS, (M+1)⁺: 441.00, ¹HNMR (500 MHz, CDCl₃), δ7.840-7.804(m, 2H), 5.304-5.240(m, 4H), 5.134-5.107(m, 1H), 4.066-4.038(t, J=7.1Hz, 2H), 3.185-3.161(m, 1H), 2.8885-2.862(m, 1H), 2.629-2.568 (m, 2H), 2.462-2.416(m, 1H), 2.305 (s, 3H), 2.344-2.323(m, 1H), 2.197-2.158(t, J=7.1 Hz, 2H), 2.108-2.033(m, 5H), 1.661-1.604(m, 2H).

EXAMPLE 9

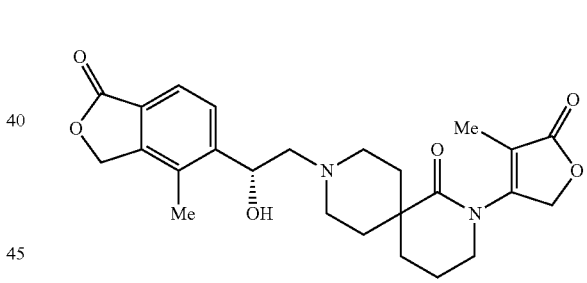

9-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-9-azoniaspiro[5.5]undecane To a solution of 2-(4-Methyl-5-oxo-2,5-dihydrofuran-3-yl)-2,9-diazaspiro[5.5]undecan-1-one (1-19, 50 mg, 0.19 mmol) in ethanol (2 mL) in a microwave tube was added (S)-4-methyl-5-(oxiran-2-yl)isobenzofuran-1(3H)-one (I-4B, 43.2 mg, 0.227 mmol)) and the resulting solution was heated at 145° C. in microwave for 35 min. After concentration, the residue was purified by preparative TLC (2000 Mm, 8% MeOH/EtOAc) to give the title compound as a free base. The free base was converted to the HCl salt by adding 1 M HCl in ether (189 Ml, 0.189 mmol) and concentrating to dryness. LC/MS, (M+1)⁺: 455

The following compounds in Table 2 were prepared in an analogous fashion to EXAMPLES 5-9 starting from the indicated piperidine and epoxide intermediates prepared as described above.

TABLE 2

| Example | Intermediates | EXAMPLE STRUCTURE/NAME | Characterization |
|---|---|---|---|
| 10 | 4B, 14 | 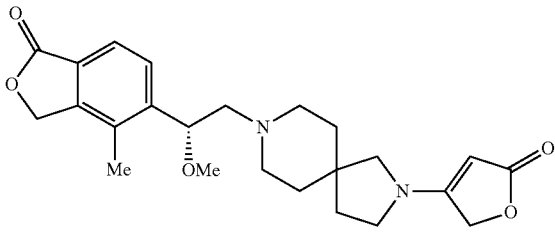<br>5-{(1R)-1-hydroxy-2-[2-(5-oxo-2,5-dihydrofuran-3-yl)-2,8-diazaspiro[4.5]dec-8-yl]ethyl}-4-methyl-2-benzofuran-1(3H)-one | LC/MS, $(M + 1)^+$: 413 |
| 11<br>12 | 4B, 26 | 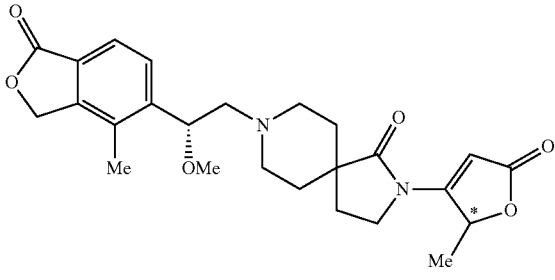<br>8-[(2R)-2-hydroxy-2-(4-methyl-1-oxo-1,3-dihydro-2-benzofuran-5-yl)ethyl]-2-(2-methyl-5-oxo-2,5-dihydrofuran-3-yl)-2,8-diazaspiro[4.5]decan-1-one<br>chiral SFC separation using Chiralpak AS column<br>Ex 11: fast eluting isomer; Ex 12: slow eluting isomer | LC/MS, $(M + 1)^+$: 441 for each isomer |
| 13<br>14 | 4B, 27 | 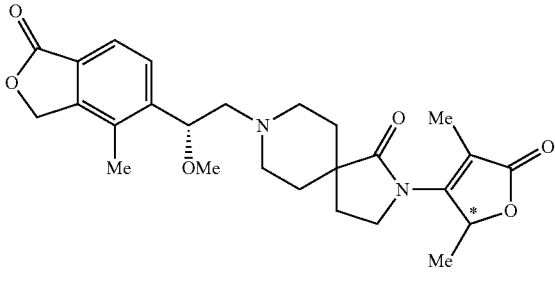<br>2-(2,4-dimethyl-5-oxo-2,5-dihydrofuran-3-yl)-8-[(1R)-2-hydroxy-2-(4-methyl-1-oxo-1,3-dihydro-2-benzofuran-5-yl)ethyl]-2,8-diazaspiro[4.5]decan-1-one,<br>chiral SFC separation using Chiralcel OD-H column<br>13: fast eluting enantiomer; 14: slow eluting enantiomer | LC/MS, $(M + 1)^+$: 455 for each isomer |
| 15 | 4B, 20 | 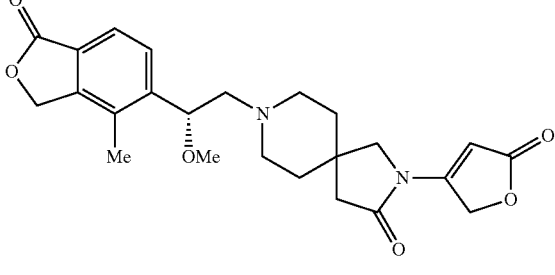<br>8-[(2R)-2-hydroxy-2-(4-methyl-1-oxo-1,3-dihydro-2-benzofuran-5-yl)ethyl]-2-(5-oxo-2,5-dihydrofuran-3-yl)-2,8-diazaspiro[4.5]decan-3-one | LC/MS, $(M + 1)^+$: 427 |

TABLE 2-continued

| Example | Intermediates | EXAMPLE STRUCTURE/NAME | Characterization |
|---|---|---|---|
| 16 | 4B, 21 | 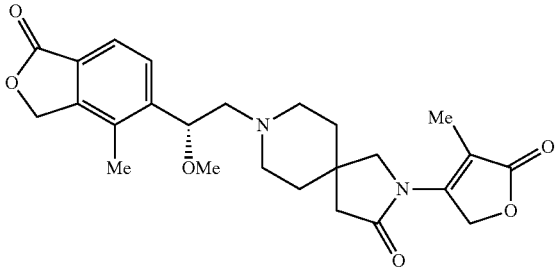<br>8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-3-one | LC/MS, (M + 1)+: 441 |
| 17 | 4B, 23 | 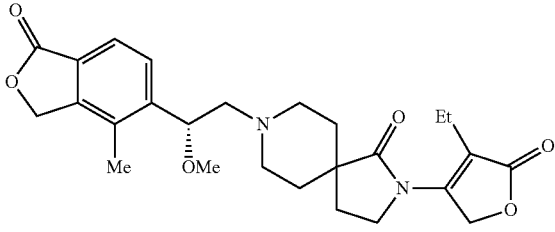<br>2-(4-ethyl-5-oxo-2,5-dihydrofuran-3-yl)-8-[(2R)-2-hydroxy-2-(4-methyl-1-oxo-1,3-dihydro-2-benzofuran-5-yl)ethyl]-2,8-diazaspiro[4.5]decan-1-one | LC/MS, (M + 1)+: 455 |
| 18 | 4B, 31 | 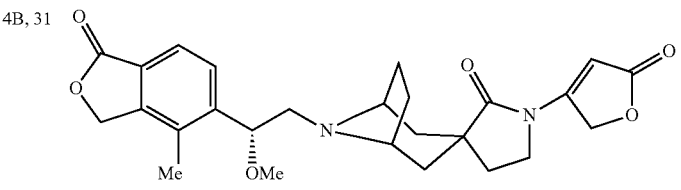<br>(1R,3r,5S)-8-[(2R)-2-hydroxy-2-(4-methyl-1-oxo-1,3-dihydro-2-benzofuran-5-yl)ethyl]-1'-(5-oxo-2,5-dihydrofuran-3-yl)-2'H-spiro[8-azabicyclo[3.2.1]octane-3,3'-pyrrolidin]-2'-one | LC/MS, (M + 1)+: 453 |
| 19 | 4B, 30 | 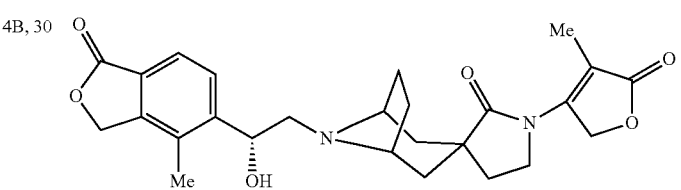<br>(1R,3r,5S)-8-[(2R)-2-hydroxy-2-(4-methyl-1-oxo-1,3-dihydro-2-benzofuran-5-yl)ethyl]-1'-(4-methyl-5-oxo-2,5-dihydrofuran-3-yl)-2'H-spiro[8-azabicyclo[3.2.1]octane-3,3'-pyrrolidin]-2'-one | LC/MS, (M + 1)+ 467 |

TABLE 2-continued

| Example | Intermediates | EXAMPLE STRUCTURE/NAME | Characterization |
|---|---|---|---|
| 20 | 4B, 32 | 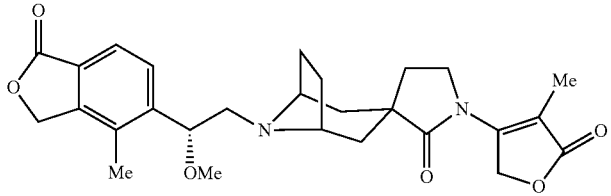<br>(1R,3s,5S)-8-((R)-2-hydroxy-2-(4-methyl-1-oxo-1,3-dihydroisobenzofuran-5-yl)ethyl)-1'-(4-methyl-5-oxo-2,5-dihydrofuran-3-yl)-8-azaspiro[bicyclo[3.2.1]octane-3,3'-pyrrolidin]-2'-one | LC/MS, $(M + 1)^+$: 467 |
| 21 | 4A, 16 | 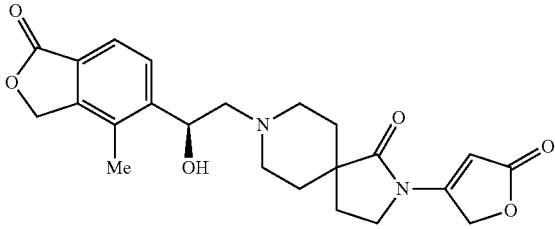<br>8-[(2S)-2-hydroxy-2-(4-methyl-1-oxo-1,3-dihydro-2-benzofuran-5-yl)ethyl]-2-(5-oxo-2,5-dihydrofuran-3-yl)-2,8-diazaspiro[4.5]decan-1-one | LC/MS, $(M + 1)^+$: 427 |
| 22 | 4B, 29 | 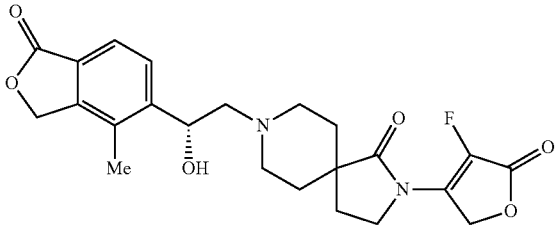<br>2-(4-fluoro-5-oxo-2,5-dihydrofuran-3-yl)-8-[(2R)-2-hydroxy-2-(4-methyl-1-oxo-1,3-dihydro-2-benzofuran-5-yl)ethyl]-1-oxo-2-aza-8-azoniaspiro[4.5]decane | LC/MS, $(M + 1)^+$: 445 |
| 23 | 4B, 18 | 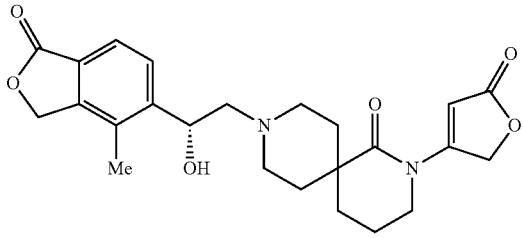 [SMILES: CC1=C(N2CCCC3(CCN(C[C@H](O)c4ccc5c(c4C)COC5=O)CC3)C2=O)COC1=O]<br>9-[(2R)-2-hydroxy-2-(4-methyl-1-oxo-1,3-dihydro-2-benzofuran-5-yl)ethyl]-1-oxo-2-(5-oxo-2,5-dihydrofuran-3-yl)-2-aza-9-azoniaspiro[5.5]undecane | LC/MS, $(M + 1)^+$: 441 |

TABLE 2-continued

| Example | Intermediates | EXAMPLE STRUCTURE/NAME | Characterization |
|---|---|---|---|
| 24 | 4B, 15 | 9-[(2R)-2-hydroxy-2-(4-methyl-1-oxo-1,3-dihydro-2-benzofuran-5-yl)ethyl]-2-(5-oxo-2,5-dihydrofuran-3-yl)-2-aza-9-azoniaspiro[5.5]undecane | LC/MS, $(M + 1)^+$: 427 |
| 25 | 4B, 28 | 2-(4-chloro-5-oxo-2,5-dihydrofuran-3-yl)-8-[(2R)-2-hydroxy-2-(4-methyl-1-oxo-1,3-dihydro-2-benzofuran-5-yl)ethyl]-1-oxo-2-aza-8-azoniaspiro[4.5]decane | LC/MS, $(M + 1)^+$: 461, 463 |
| 26 | 4B, 35 polar | 6-hydroxy-8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane | LC/MS, $(M + 1)^+$: 457 |
| 27 28 | 4B, 36B | 6-fluoro-8-((R)-2-hydroxy-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one; SFC separation using Chiralcel IA column 27: faster eluting single isomer; 28: slower eluting single isomer | LC/MS, $(M + 1)^+$: 459 for each isomer |

TABLE 2-continued

| Example | Intermediates | EXAMPLE STRUCTURE/NAME | Characterization |
|---|---|---|---|
| 29 30 | 4B, 42 | (R)-8-((R)-2-hydroxy-2-(4-methyl-1-oxo-1,3-dihydroisobenzofuran-5-yl)ethyl)-3-methyl-2-(4-methyl-5-oxo-2,5-dihydrofuran-3-yl)-2,8-diazaspiro[4.5]decan-1-one, and (S)-8-((R)-2-hydroxy-2-(4-methyl-1-oxo-1,3-dihydroisobenzofuran-5-yl)ethyl)-3-methyl-2-(4-methyl-5-oxo-2,5-dihydrofuran-3-yl)-2,8-diazaspiro[4.5]decan-1-one; SFC separation using Chiralpak AS-H column 29: faster eluting single isomer; 30: slower eluting single isomer | LC/MS, $(M + 1)^+$: 455 for each isomer |
| 31 | 4B, 25 | 2-(4-cyclopropyl-5-oxo-2,5-dihydrofuran-3-yl)-8-[(2R)-2-hydroxy-2-(4-methyl-1-oxo-1,3-dihydro-2-benzofuran-5-yl)ethyl]-2,8-diazaspiro[4.5]decan-1-one | LC/MS, $(M + 1)^+$: 467 |
| 32 33 | 4B, 37A 4B, 37B | 4-hydroxy-8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane, Two single isomers, stereochemistry at lactam hydroxy not determined | LC/MS, $(M + 1)^+$: 457 for each isomer |
| 34 35 | 4B, 39A 4B, 39B | 8-((R)-2-hydroxy-2-(4-methyl-1-oxo-1,3-dihydroisobenzofuran-5-yl)ethyl)-4-methoxy-2-(4-methyl-5-oxo-2,5-dihydrofuran-3-yl)-2,8-diazaspiro[4.5]decan-1-one Two single isomers, | LC/MS, $(M + 1)^+$: 471 for each isomer |

TABLE 2-continued

| Example | Intermediates | EXAMPLE STRUCTURE/NAME | Characterization |
|---|---|---|---|
| 36 | 4B, 38 | 8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1,4-dioxo-2-aza-8-azoniaspiro[4.5]decane | LC/MS, $(M + 1)^+$: 455 |
| 37 | 7B, 17 | 8-[(2S)-2-hydroxy-2-(6-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane, absolute chemistry presumed but not unambiguously determined | LC/MS, $(M + 1)^+$: 441 |
| 38 | 7A, 17 | 8-[(2R)-2-hydroxy-2-(6-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane, absolute chemistry presumed but not unambiguously determined | LC/MS, $(M + 1)^+$: 441 |
| 39 | 4B, 33A | (1R,3r,5S)-8-[(2R)-2-hydroxy-2-(4-methyl-1-oxo-1,3-dihydro-2-benzofuran-5-yl)ethyl]-5'-methyl-1'-(5-oxo-2,5-dihydrofuran-3-yl)-2'H-spiro[8-azabicyclo[3.2.1]octane-3,3'-pyrrolidin]-2'-one; two single isomers, stereochemistry at methyl lactam not established | LC/MS, $(M + 1)^+$: 467 for each isomer |
| 40 | 4B, 33B | | |

TABLE 2-continued

| Example | Intermediates | EXAMPLE STRUCTURE/NAME | Characterization |
|---|---|---|---|
| 41<br>42 | 4A, 33A<br>4A, 33B | (1R,3r,5S)-8-[(2S)-2-hydroxy-2-(4-methyl-1-oxo-1,3-dihydro-2-benzofuran-5-yl)ethyl]-5'-methyl-1'-(5-oxo-2,5-dihydrofuran-3-yl)-2'H-spiro[8-azabicyclo[3.2.1]octane-3,3'-pyrrolidin]-2'-one<br>two single isomers, | LC/MS,<br>(M + 1)⁺:<br>467 for<br>each<br>isomer |
| 43 | 4B, 40 | 8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]dec-3-ene | LC/MS,<br>(M + 1)⁺:<br>441 |
| 44 | 4B, 41 | (R)-8-(2-hydroxy-2-(4-methyl-1-oxo-1,3-dihydroisobenzofuran-5-yl)ethyl)-2-(5-oxo-2,5-dihydrofuran-3-yl)-2,8-diazaspiro[4.5]dec-3-en-1-one | LC/MS,<br>(M + 1)⁺:<br>425 |
| 45 | 4B, 34 | (1R,3's,5S)-9-[(2R)-2-hydroxy-2-(4-methyl-1-oxo-1,3-dihydro-2-benzofuran-5-yl)ethyl]-7-methyl-1'-(4-methyl-5-oxo-2,5-dihydrofuran-3-yl)-2'H-spiro[7,9-diazabicyclo[3.3.1]nonane-3,3'-pyrrolidin]-2'-one | LC/MS,<br>(M + 1)⁺:<br>496 |

| Example | Intermediates | EXAMPLE STRUCTURE/NAME | Characterization |
|---|---|---|---|
| 46 | 4A, 34 | (1R,3′s,5S)-9-[(2S)-2-hydroxy-2-(4-methyl-1-oxo-1,3-dihydro-2-benzofuran-5-yl)ethyl]-7-methyl-1′-(4-methyl-5-oxo-2,5-dihydrofuran-3-yl)-2′H-spiro[7,9-diazabicyclo[3.3.1]nonane-3,3′-pyrrolidin]-2′-one | LC/MS, (M + 1)$^+$: 496 |

EXAMPLE 47

8-[(2R)-2-fluoro-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one Step A: 8-[(2S)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one: To a suspension of 4-methyl-5-[(2S)-oxiran-2-yl]-2-benzofuran-1(3H)-one (I-4A)(200 mg, 1.05 mmol) and 2-(4-methyl-5-oxo-2,5-dihydrofuran-3-yl)-2,8-diazaspiro[4.5]decan-1-one (300 mg, 1.05 mmol) in 10 mL of EtOH was added DIPEA (271 mg, 2.10 mmol). The resulting mixture was stirred at 80° C. overnight, and then cooled to room temperature; the solvent was removed under vacuum. The residue was purified by flash chromatography (ethyl acetate: MeOH=20:1) to afford title compound. MS-ESI (m/z): 441 (M+1)

Step B: 8-[(2R)-2-fluoro-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one: To a solution of the product of Step A, (170 mg, 0.39 mmol) in 5 mL of DCM was added Et$_3$N.3HF (10 drops) and DAST (5 drops) at −78° C. The mixture was stirred overnight and quenched with aqueous NaHCO$_3$. The organic layer was separated and the aqueous was extracted with DCM. The combined organic layers were dried over anhydrous Na$_2$SO$_4$, filtered and the solvent was removed under vacuum, the residue was purified by preparative TLC (EtOAc: MeOH=1:1) to afford title compound. $^1$H NMR (400 MHz, CDCl$_3$): δ 7.81 (d, J=7.8 Hz, 1H), 7.61 (d, J=7.8 Hz, 1H), 6.02-5.88 (m, 1H), 5.28-5.22 (m, 4H), 4.01 (t, J=7.0 Hz, 2H), 3.06-2.85 (m, 3H), 2.73-2.61 (m, 1H), 2.46-2.38 (m, 2H), 2.31 (s, 3H), 2.11 (t, J=7.0 Hz, 2H), 2.05-1.96 (m, 5H), 1.55-1.50 (m, 2H). MS-ESI (m/z): 443 (M+1)$^+$.

EXAMPLE 48

8-[(2S)-2-fluoro-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one The title compound was prepared in an analogous fashion to that described immediately above for the synthesis of Example 47, except starting from 4-methyl-5-[(2R)-oxiran-2-yl]-2-benzofuran-1(3H)-one (I-4B). $^1$H NMR (400 MHz, CDCl$_3$): δ 7.81 (d, J=7.8 Hz, 1H), 7.61 (d, J=7.8 Hz, 1H), 6.02-5.88 (m, 1H), 5.28-5.23 (m, 4H), 4.01 (t, J=7.0 Hz, 2H), 3.05-2.86 (m, 3H), 2.73-2.61 (m, 1H), 2.46-2.38 (m, 2H), 2.31 (s, 3H), 2.13 (t, J=7.0 Hz, 2H), 2.05-1.96 (m, 5H), 1.55-1.50 (m, 2H). MS-ESI (m/z): 443 (M+1)$^+$.

EXAMPLE 49

8-[(2R)-2-methoxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane Step A: (S)-8-(2-chloro-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one: To a solution of 8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one (Example 7) (1.1 g, 2.5 mmol) and methanesulfonyl chloride (0.584 mL, 7.49 mmol) in DCM (30 mL) was added triethylamine (1.22 mL, 8.74 mmol) and N,N-dimethylpyridin-4-amine (0.031 g, 0.250 mmol) at −10 to −15° C. (ice-NaCl). The mixture was stirred at the same temperature for 20 min, quenched with NH$_4$Cl aqueous. The organic layer was separated, and the aqueous was extracted with DCM (30 mL). The combined organic layers were dried (MgSO$_4$) and concentrated under reduced pressure to give product was used in the next step without further purification. LCMS: 459.05 (M+1).

Step B: 8-[(2R)-2-methoxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane: One small piece of sodium metal in methanol (20 mL) was stirred until the sodium disappeared. The product of Step A (45 mg, 0.098 mmol) was added to the solution. The mixture was stirred at rt for 20 min. 3 mL 1 N HCl was added, and the mixture was concentrated. The residue was dissolved in DMSO, and was purified by Gilson reverse phase HPLC (3%-45% of 0.1% TFA-water in 0.1% TFA-AcCN) to give the title compound. $^1$HNMR (500 MHz), δ 7.82 (1 H, d, J=7.6 Hz), 7.70 (1 H, d, J=7.8 Hz), 5.42 (2 H, s), 5.28 (2 H, s), 5.20 (1 H, m), 4.15 (3 H, s), 3.50-3.90 (4 H, m), 3.12-3.50 (4 H, m), 2.45 (3 H, s), 2.15-2.37 (4 H, m), 2.07 (3 H, s), 1.95-2.05 (2 H, m). LC-MS 455.1 (M+1), 477.09 (M+23).

EXAMPLE 50

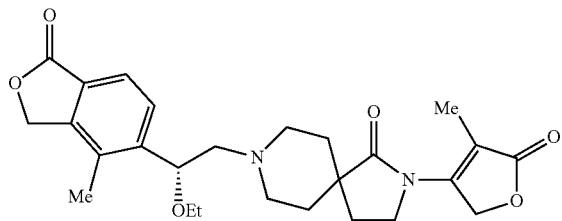 [SMILES: CCO[C@@H](CN1CCC2(CC1)CCN(C1=C(C)C(=O)OC1)C2=O)c1ccc2c(c1C)COC2=O]

8-[(2R)-2-ethoxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one The title compound was prepared using essentially the same procedure as Example 49 except for use of ethanol in place of methanol as the reaction solvent in Step B. LC-MS: 469.13 (M+1).

EXAMPLE 51

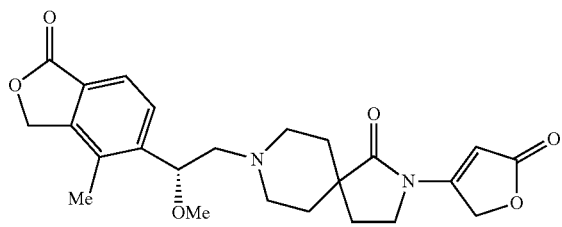 [SMILES: CO[C@@H](CN1CCC2(CC1)CCN(C1=CC(=O)OC1)C2=O)c1ccc2c(c1C)COC2=O]

8-[(2R)-2-methoxy-2-(4-methyl-1-oxo-1,3-dihydro-2-benzofuran-5-yl)ethyl]-2-(5-oxo-2,5-dihydrofuran-3-yl)-2,8-diazaspiro[4.5]decan-1-one The title compound was prepared using essentially the same procedure as Example 49, except starting from 8-[(2R)-2-hydroxy-2-(4-methyl-1-oxo-1,3-dihydro-2-benzofuran-5-yl)ethyl]-2-(5-oxo-2,5-dihydrofuran-3-yl)-2,8-diazaspiro[4.5]decan-1-one. LC-MS: 441 (M+1).

EXAMPLE 52

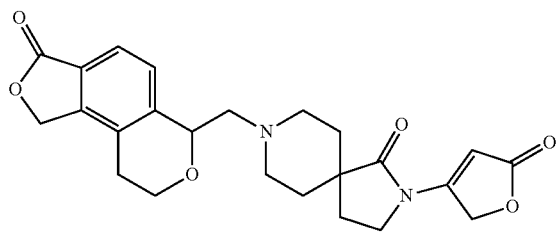 [SMILES: O=C1C=C(N2CCC3(CCN(CC4OCCc5c4ccc4c5COC4=O)CC3)C2=O)CO1]

1-oxo-2-(5-oxo-2,5-dihydrofuran-3-yl)-8-[3-oxo-3,6,8,9-tetrahydro-1H-furo[3,4-f]isochromen-6-yl)methyl]-2-aza-8-azoniaspiro[4.5]decane: (3-oxo-3,6,8,9-tetrahydro-1H-furo[3,4-f]isochromen-6-yl)methyl-4-methylbenzenesulfonate (I-8) (80 mg, 0.21 mmol) was combined with 2-(5-Oxo-2,5-dihydrofuran-3-yl)-2,8-diazaspiro[4.5]decan-1-one (I-16) (50.5 mg, 0.214 mmol) and triethylamine (30 μL, 0.21 mmol) in acetonitrile (2 mL) in a microwave tube and heated at 140° C. The solvent was removed and the residue was purified by MPLC eluting with 5% methanol/DCM to afford the title compound as a mixture of two enantiomers. LC-MS: 439 (M+1).

EXAMPLES 53A, 53B, 53C, 53D (Four Individual Isomers)

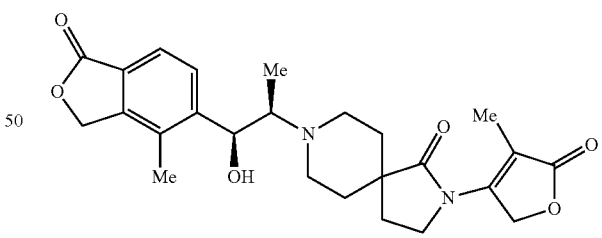

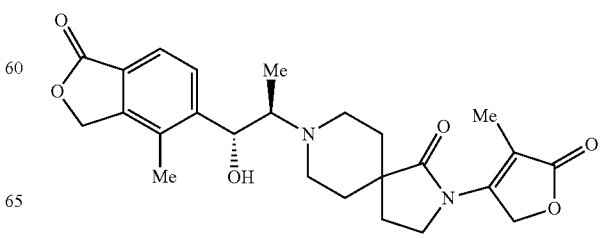

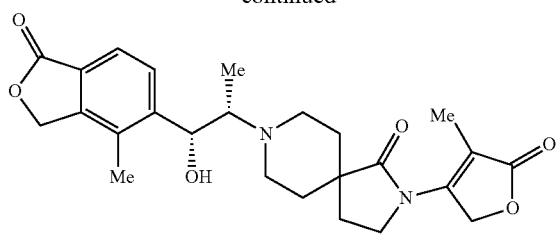

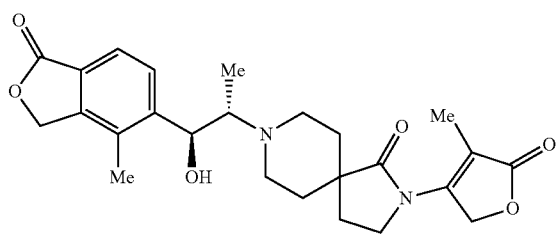

8-((1S,2R)-1-hydroxy-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one 8-((1R,2R)-1-hydroxy-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one 8-((1R,2S)-1-hydroxy-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one; and 8-((1S,2S)-1-hydroxy-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one (Separated to Four Single Isomers)

To 5-(1,2-dihydroxypropyl)-4-methylisobenzofuran-1(3H)-one (I-6) (300 mg, 1.35 mmol) and 2-(4-methyl-5-oxo-2,5-dihydrofuran-3-yl)-2,8-diazaspiro[4.5]decan-1-one (I-17) (405 mg, 1.62 mmol) in t-amyl alcohol (2.7 mL) was added 2-(dicyclohexylphosphino)-1-phenyl-1H-pyrrole (82 mg, 0.243 mmol) and ruthenium carbonyl (51.8 mg, 0.081 mmol). The reaction mixture was degassed and heated at 140° C. for two days. The reaction mixture was concentrated and purified by column chromatography (0-10% MeOH/DCM) to separate the syn and anti isomers. The resulting syn and anti isomers were then respectively purified by SFC-HPLC, using the following conditions: chiralpak AD, 30×250 mm, 65% MeOH+0.2% DEA, 70 mL/min to give four single isomers of the title compound. Absolute stereochemistry has not been assigned with certainty for each isomer at this time. They are designated as follows: Isomer 53A: faster eluting from MeOH column chromatography, faster eluting from SFC-HPLC; LC/MS: [(M+1)]$^+$=455. Isomer 53B: faster eluting from MeOH column chromatography, slower eluting from SFC-HPLC; LC/MS: [(M+1)]$^+$=455. Isomer 53C: slower eluting from MeOH column chromatography, faster eluting from SFC-HPLC; LC/MS: [(M+1)]$^+$=455. Isomer 53D: slower eluting from MeOH column chromatography, slower eluting from SFC-HPLC; LC/MS: [(M+1)]$^+$=455

EXAMPLE 54

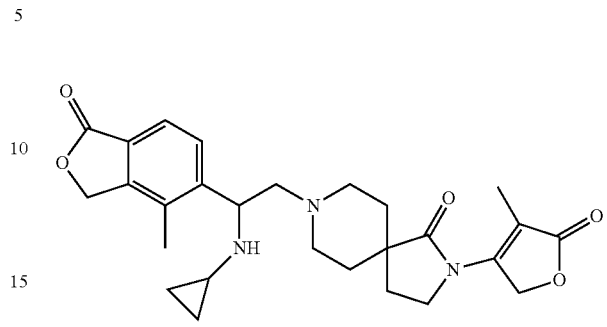

8-(2-(cyclopropylamino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one Step A: 8-(2-(4-methyl-1-oxo-1,3-dihydroisobenzofuran-5-yl)-2-oxoethyl)-2-(4-methyl-5-oxo-2,5-dihydrofuran-3-yl)-2,8-diazaspiro[4.5]decan-1-one 2-(4-methyl-5-oxo-2,5-dihydrofuran-3-yl)-2,8-diazaspiro[4.5]decan-1-one (I-17) (2 g, 7.99 mmol), 5-(2-Bromoacetyl)-4-methyl-3H-isobenzofuran-1-one (I-4B, method 2, step F) (2.150 g, 7.99 mmol) and N-ethyl-N-isopropylpropan-2-amine (3.48 mL, 19.98 mmol) in DCM (50 mL) were stirred overnight at rt. The mixture was washed with saturated ammonium chloride aqueous and brine, dried over MgSO$_4$, and concentrated under reduced pressure. The crude material was used in the next step without further purification. $^1$H-NMR (500 MHz, CDCl$_3$): δ ppm 7.83 (1H, d, J=7.8 Hz), 7.79 (1 H. , d, J=7.8 Hz), 5.34 (2 H, s), 5.32 (2 H, s), 5.26 (2 H, s), 4.03 (2 H, t, J=7.0 Hz), 3.71 (1 H, m), 3.15 (1 H, m), 2.94 (2 H, m), 2.47 (2 H, t, J=7.0 Hz), 2.42 (3 H, s), 2.17 (2 H, m), 2.07 (3 H, s), 2.02 (2 H, m), 1.58 (2 H, m). LCMS 438.9 (M+1).

Step B: 8-(2-(cyclopropylamino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one: To a mixture of 8-(2-(4-methyl-1-oxo-1,3-dihydroisobenzofuran-5-yl)-2-oxoethyl)-2-(4-methyl-5-oxo-2,5-dihydrofuran-3-yl)-2,8-diazaspiro[4.5]decan-1-one (25 mg, 0.057 mmol) and cyclopropanamine (6.5 mg, 0.114 mmol) in anhydrous 5% HOAc/THF (1 mL) was added NaCNBH$_3$ (18 mg, 0.28 mmol). The reaction was sealed and shaken at ambient temperature for 16 h. LCMS showed that the product was formed. The reaction was quenched with water (0.5 mL) and the solvent was evaporated under reduced pressure. The residue was dissolved in DMSO (1.5 mL) and filtered. The crude product was purified by using reversed-phase HPLC (Acetonitrile with 0.1% TFA: water with 0.1% TFA from 10% to 60%) to give the title compound. LC-MS (IE, m/z): 480 [M+1]$^+$.

The Examples in the Table 3 below were prepared in a similar fashion to 8-(2-(cyclopropylamino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one above (Example 54, Step B) starting from 8-(2-(4-methyl-1-oxo-1,3-dihydroisobenzofuran-5-yl)-2-oxoethyl)-2-(4-methyl-5-oxo-2,5-dihydrofuran-3-yl)-2,8-diazaspiro[4.5]decan-1-one (Example 54, Step B) and the indicated amines.

TABLE 3

| EXAMPLE | Amine | Structure | Characterization LC-MS |
|---|---|---|---|
| 55 | 2,2-difluoro ethanamine | 8-(2-((2,2-difluoroethyl)amino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one | 504 (M + H)+ |
| 56 | Cyclo butanamine | 8-(2-(cyclobutylamino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one | 494 (M + H)+ |
| 57 | azetidine | 8-(2-(azetidin-1-yl)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one | 480 (M + H)+ |
| 58 | 2-methoxy ethanamine | 8-(2-((2-methoxyethyl)amino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one | 498 (M + H)+ |

TABLE 3-continued

| EXAMPLE | Amine | Structure | Characterization LC-MS |
|---|---|---|---|
| 59 | 3-amino propane-nitrile | 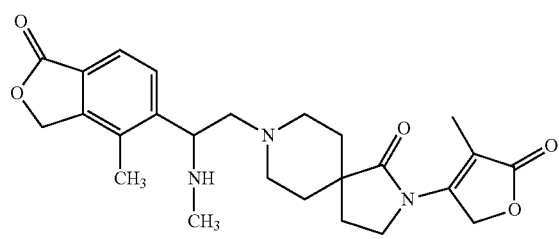<br>3-((1-(4-methyl-1-oxo-1,3-dihydroisobenzofuran-5-yl)-2-(2-(4-methyl-5-oxo-2,5-dihydrofuran-3-yl)-1-oxo-2,8-diazaspiro[4.5]decan-8-yl)ethyl)amino)propanenitrile | 493 (M + H)+ |

EXAMPLE 60

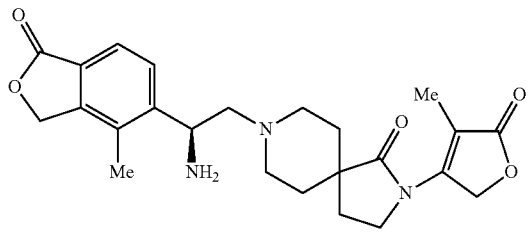 [SMILES: CC1=C(N2CCC3(CCN(C[C@@H](N)c4ccc5c(c4C)COC5=O)CC3)C2=O)COC1=O]

8-[2-(methylamino)-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one To a mixture of 8-(2-(4-methyl-1-oxo-1,3-dihydroisobenzofuran-5-yl)-2-oxoethyl)-2-(4-methyl-5-oxo-2,5-dihydrofuran-3-yl)-2,8-diazaspiro[4.5]decan-1-one (25 mg, 0.057 mmol) and methyl amine (4 mg, 0.114 mmol) in anhydrous THF was added Ti(O-iPr)$_4$(35 µL, 0.114 mmol). The reaction was sealed and shaken at ambient temperature for 16 hr. To this reaction, EtOH (200 proof, 0.5 mL) was added followed by adding NaBH$_4$ (11 mg, 0.171 mmol) portion-wise within 30 min. The reaction was shaken for 3 hr and quenched with water (0.5 mL). The reaction was partitioned between EtOAc (4 mL×2) and ammonium (2N, 1.5 mL). The organic phase was combined and evaporated under reduced pressure. The residue was dissolved in DMSO (1.5 mL) and filtered. The crude product was purified by using reversed-phase HPLC (Acetonitrile with 0.1% TFA: water with 0.1% TFA from 10% to 60%) to give the title compound. LC-MS (IE, m/z): 454 [M+1]+.

EXAMPLE 61

(S)-8-(2-amino-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one Step A: (S)-8-(2-azido-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one: To a suspension of 8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one (Example 7, 300 mg, 0.68 mmol) and diphenylphosphoryl azide (578 mg, 1.36 mmol) in a mixed solvent of toluene and dichloromethane (v:v, 10:1, 11 mL) was added DBU (310 mg, 1.36 mmol). The reaction mixture was stirred at 35° C. for 20 h. The solvent was removed by evaporation and the residue was purified by flash column chromatography (0-100% ethyl acetate in petroleum ether gradient) to afford the title compound. $^1$H NMR (400 MHz, CDCl$_3$): δ 7.32 (d, J=8.0 Hz, 1H), 7.50 (d, J=8.0 Hz, 1H), 5.20 (s, 2H), 5.18 (s, 2H), 4.94 (dd, J=4.0 Hz, 9.2 Hz, 1H), 3.94 (t, J=6.8 Hz, 2H), 2.88-2.85 (m, 2H), 2.72-2.67 (m, 1H), 2.54-2.50 (m, 1H), 2.42-2.39 (m, 1H), 2.33-2.27 (m, 4H), 2.04 (t, J=6.8 Hz, 2H), 1.95 (s, 3H), 1.94-1.87 (m, 2H), 1.51-1.47 (m, 2H); MS-ESI (m/z): 466 (M+1)+.

Step B: (S)-8-(2-amino-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one: To a solution of (S)-8-(2-azido-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one (200 mg, 0.43 mmol) in a mixed solvent of tetrahydrofuran and water (v:v, 12:1, 20 mL) was added triphenylphosphine (225 mg, 0.86 mmol) under nitrogen atmosphere. The reaction mixture was stirred at room temperature for 18 h. The solvent was removed by evaporation and the residue was purified by preparative TLC (dichloromethane: methanol=10:1) to afford the title compound as a solid.

$^1$H NMR (400 MHz, CDCl$_3$): δ 7.86 (d, J=7.6 Hz, 1H), δ 7.53 (d, J=7.6 Hz, 1H), 5.24 (s, 2H), 5.22 (s, 2H), 4.50 (dd, J=4.0 Hz, 8.8 Hz, 1H), 3.98 (t, J=6.8 Hz, 2H), 3.04-3.01 (m, 1H), 2.81-2.78 (m, 1H), 2.40-2.34 (m, 2H), 2.30 (s, 3H), 2.18-2.08 (m, 4H), 2.01 (s, 3H), 2.00-1.95 (m, 2H), 1.51-1.47 (m, 2H); MS-ESI (m/z): 440 (M+1)+.

EXAMPLE 62

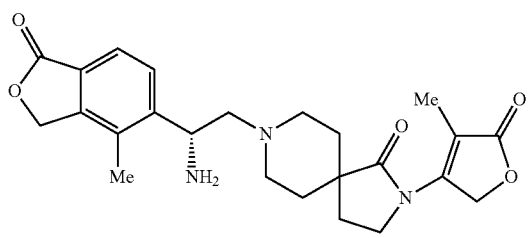 [SMILES: CC1=C(N2CCC3(CCN(C[C@H](N)c4ccc5c(c4C)COC5=O)CC3)C2=O)COC1=O]

(R)-8-(2-amino-2-(4-methyl-1-oxo-1,3-dihydroisobenzofuran-5-yl)ethyl)-2-(4-methyl-5-oxo-2,5-dihydrofuran-3-yl)-2,8-diaz aspiro[4.5]decan-1-one Step A: (R)-8-(2-azido-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one: To a suspension of 8-[(2S)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one (Example 8, 500 mg, 1.13 mmol) and diphenylphosphoryl azide (643 mg, 1.36 mmol) in a mixed solvent of toluene and dichloromethane (v:v, 10:1, 11 mL) was added DBU (343 mg, 2.26 mmol). The reaction mixture was stirred at 35° C. for 20 h. The solvent was removed by evaporation and the residue was purified by flash column chromatography (0-100% ethyl acetate in petroleum ether) to afford the title compound. $^1$H NMR (400 MHz, CDCl$_3$): δ 7.78 (d, J=8.0 Hz, 1H), 7.55 (d, J=8.0 Hz, 1H), 5.26 (s, 2H), 5.23 (s, 2H), 4.99 (dd, J=4.0 Hz, 9.2 Hz, 1H), 4.00 (t, J=6.8 Hz, 2H), 2.95-2.87 (m, 2H), 2.78-2.73 (m, 1H), 2.60-2.57 (m, 1H), 2.48-2.43 (m, 1H), 2.33 (s, 3H), 2.10 (t, J=6.8 Hz, 2H), 2.03-1.86 (m, 6H), 1.51-1.48 (m, 2H); MS-ESI (m/z): 466 (M+1)$^+$.

Step C: (R)-8-(2-amino-2-(4-methyl-1-oxo-1,3-dihydroisobenzofuran-5-yl)ethyl)-2-(4-methyl-5-oxo-2,5-dihydrofuran-3-yl)-2,8-diazaspiro[4,5]decan-1-one: To a solution of (R)-8-(2-azido-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one (250 mg, 0.54 mmol) in a mixed solvent of tetrahydrofuran and water (v:v, 12:1, 20 mL) was added triphenylphosphine (283 mg, 1.08 mmol) under nitrogen atmosphere. The reaction mixture was stirred at room temperature for 18 h. The solvent was removed by evaporation and the residue was purified by preparative TLC (dichloromethane: methanol=10:1) to afford the title compound. $^1$H NMR (400 MHz, Methanol-d4): δ 7.80 (d, J=8.0 Hz, 1H), δ 7.66 (d, J=8.0 Hz, 1H), 5.40 (s, 2H), 5.24 (s, 2H), 4.73 (dd, J=4.0 Hz, 8.8 Hz, 1H), 4.09 (t, J=6.8 Hz, 2H), 3.30-3.21 (m, 1H), 2.98-2.91 (m, 1H), 2.87-2.81 (m, 1H), 2.70-2.66 (m, 1H), 2.55-2.47 (m, 2H), 2.40 (s, 3H), 2.18-2.07 (m, 4H), 2.00 (s, 3H), 1.74-1.68 (m, 2H). MS-ESI (m/z): 440 (M+1)$^+$.

EXAMPLE 63

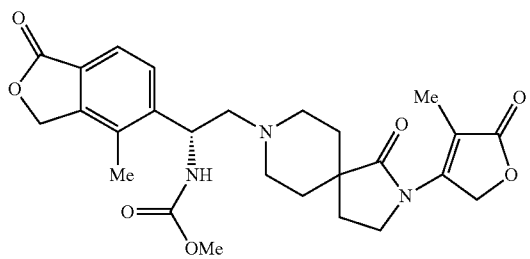 [SMILES: COC(=O)N[C@@H](CN1CCC2(CC1)CCN(C1=C(C)C(=O)OC1)C2=O)c1ccc2c(c1C)COC2=O]

Methyl {(1R)-1-(4-methyl-1-oxo-1,3-dihydro-2-benzofuran-5-yl)-2-[2-(4-methyl-5-oxo-2,5-dihydrofuran-3-yl)-1-oxo-2,8-diaz aspiro[4.5]dec-8-yl] ethyl}carbamate To a solution of (R)-8-(2-amino-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one (Example 62) (35 mg, 0.08 mmol) and triethylamine (17 µL, 0.12 mmol) in dichloromethane (2 mL) was added methyl chloroformate (11 mg, 0.12 mmol) at 0° C. under nitrogen atmosphere. The reaction mixture was allowed to warm to room temperature and stir for 2 h. TLC indicated half of starting material remained. The reaction mixture was re-cooled to 0° C. and triethylamine (17 µL, 0.12 mmol) was added thereto, followed by methyl chloroformate (11 mg, 0.12 mmol). The reaction mixture was allowed to warm to room temperature and stirred for another 2 h. TLC showed the reaction was complete. The resulting mixture was concentrated in vacuo. The residue was taken up into small amount of DCM and purified by preparative TLC (dichloromethane: methanol=15:1) to afford the title compound. MS-ESI (m/z): 498 (M+1)$^+$.

EXAMPLE 64

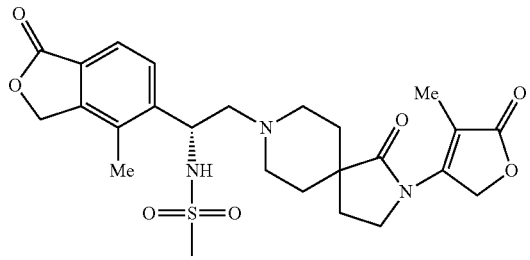 [SMILES: CC1=C(N2CCC3(CCN(C[C@H](NS(C)(=O)=O)c4ccc5c(c4C)COC5=O)CC3)C2=O)COC1=O]

(R)—N-(1-(4-methyl-1-oxo-1,3-dihydroisobenzofuran-5-yl)-2-(2-(4-methyl-5-oxo-2,5-dihydrofuran-3-yl)-1-oxo-2,8-diazaspiro[4.5]decan-8-yl)ethyl)methanesulfonamide To a solution of (R)-8-(2-amino-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one (30 mg, 0.068 mmol) and triethylamine (29 µL, 0.20 mmol) in DCM (2 mL) was added methanesulfonyl chloride (5.3 µL, 0.068 mmol) at 0° C. under nitrogen atmosphere. The reaction mixture was allowed to warm to room temperature and stirred for 3 h. TLC indicated the reaction was complete. Evaporation of the solvent afforded the residue, which was taken up into small amount of DCM and purified by preparative TLC (dichloromethane: methanol=10:1) to give the title compound. $^1$H NMR (400 MHz, CDCl$_3$): δ 7.63 (dd, J=8.0 Hz, J=8.8 Hz, 2H), 5.30 (s, 2H), 5.15 (s, 2H), 4.95-4.92 (m, 1H), 4.00 (t, J=7.2 Hz, 2H), 2.94-2.91 (m, 1H), 2.82-2.78 (m, 1H), 2.72 (s, 3H), 2.65-2.59 (m, 1H), 2.42-2.39 (m, 1H), 2.38-2.24 (m, 4H), 2.21-2.18 (m, 1H), 2.07 (t, J=7.2 Hz, 2H), 1.92 (s, 3H), 1.86-1.72 (m, 2H), 1.52-1.47 (m, 2H). MS-ESI (m/z): 518 (M+1)$^+$.

EXAMPLE 65

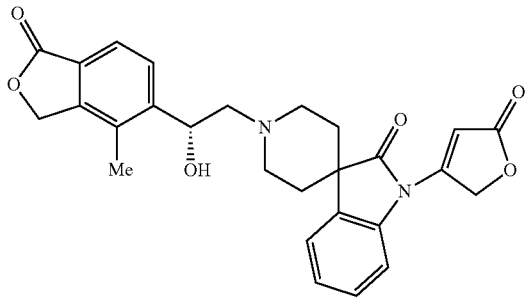 [SMILES: Cc1c([C@@H](O)CN2CCC3(CC2)C(=O)N(C2=CC(=O)OC2)c2ccccc23)ccc2c1COC2=O]

1'-[(2R)-2-hydroxy-2-(4-methyl-1-oxo-1,3-dihydro-2-benzofuran-5-yl)ethyl]-2-oxo-1-(5-oxo-2,5-dihydrofuran-3-yl)-1,2-dihydrospiro[indole-3,4'-piperidinium]

Step A: (R)-1'-(2-hydroxy-2-(4-methyl-1-oxo-1,3-dihydroisobenzofuran-5-yl)ethyl)spiro[indoline-3,4'-piperidin]-2-one: Commercially available spiro[indoline-3,4'-piperidin]-2-one hydrochloride (500 mg, 2.10 mmol) was combined with 4-methyl-5-[(2S)-oxiran-2-yl]-2-benzofuran-1(3H)-one (I-4A) (398 mg, 2.10 mmol) and DIEA (439 μL, 2.51 mmol) in ethanol (7 mL) and heated at 80° C. for 3 h. The reaction mixture was concentrated and purified by MPLC eluting first with 30% ethyl acetate hexanes and then with 10% methanol/DCM to afford the title compound which was a mixture of regioisomers. MS-ESI (m/z): 393 (M+1)$^+$;

Step B: 1'-[(2R)-2-hydroxy-2-(4-methyl-1-oxo-1,3-dihydro-2-benzofuran-5-yl)ethyl]-2-oxo-1-(5-oxo-2,5-dihydrofuran-3-yl)-1,2-dihydrospiro[indole-3,4'-piperidinium]: (R)-1'-(2-hydroxy-2-(4-methyl-1-oxo-1,3-dihydroisobenzofuran-5-yl)ethyl)spiro[indoline-3,4'-piperidin]-2-one (502 mg, 1.28 mmol), 4-bromofuran-2-one (250 mg, 1.53 mmol), cesium carbonate (625 mg, 1.92 mmol), Pd(dba)$_2$ (37 mg, 0.064 mmol), Xantphos (111 mg, 0.192 mmol), were combined in a microwave vial in 5 mL of toluene. The suspension was purged with nitrogen and heated at 90° C. overnight. The reaction mixture was filtered through CELITE® washing with ethyl acetate and the filtrate was concentrated. The crude product was purified by MPLC using an ethyl acetate hexanes gradient first, then 10% methanol/DCM to elute the product. In order to separate the desired product from impurities and regioisomers, the residue was further purified by preparative TLC (10% methanol/DCM) and by SFC HPLC using a chiralcel OD column. MS-ESI (m/z): 475 (M+1)$^+$.

The following compounds in Table 4 were prepared in an analogous fashion to EXAMPLES 5-9 starting from the indicated piperidine and epoxide intermediates prepared as described above. In instances where mixtures of isomers were produced, SFC chiral HPLC was employed to separate the isomers using the HPLC column indicated.

TABLE 4

| EXAMPLE | Intermediates | EXAMPLE STRUCTURE/NAME | Characterization |
|---|---|---|---|
| 66 67 | 4B, 43 | (S)-3-ethyl-8-((R)-2-hydroxy-2-(4-methyl-1-oxo-1,3-dihydroisobenzofuran-5-yl)ethyl)-2-(5-oxo-2,5-dihydrofuran-3-yl)-2,8-diazaspiro[4.5]decan-1-one, and (R)-3-ethyl-8-((R)-2-hydroxy-2-(4-methyl-1-oxo-1,3-dihydroisobenzofuran-5-yl)ethyl)-2-(5-oxo-2,5-dihydrofuran-3-yl)-2,8-diazaspiro[4.5]decan-1-one; 66: faster eluting diastereomer, 67: slower eluting diastereomer from chiral SFC separation eluting with AS-H (2X15 cm) column | LC/MS, (M + 1)$^+$: 455 for each isomer |
| 68 69 | 4B, 44 | (S)-3-cyclopropyl-8-((R)-2-hydroxy-2-(4-methyl-1-oxo-1,3-dihydroisobenzofuran-5-yl)ethyl)-2-(5-oxo-2,5-dihydrofuran-3-yl)-2,8-diazaspiro[4.5]decan-1-one, and (R)-3-cyclopropyl-8-((R)-2-hydroxy-2-(4-methyl-1-oxo-1,3-dihydroisobenzofuran-5-yl)ethyl)-2-(5-oxo-2,5-dihydrofuran-3-yl)-2,8-diazaspiro[4.5]decan-1-one, 68: faster eluting diastereomer, 69: slower eluting diastereomer from chiral SFC separation using Chiralpak AS column | LC/MS, (M + 1)$^+$: 467 for each isomer |

TABLE 4-continued

| EXAMPLE | Intermediates | EXAMPLE STRUCTURE/NAME | Characterization |
|---|---|---|---|
| 70 | 4B, 45 | 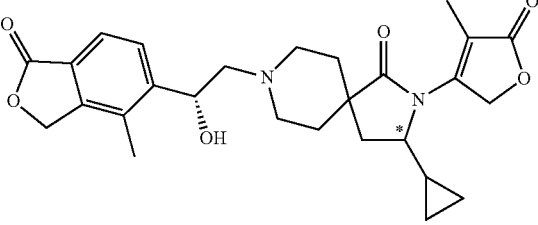  3-cyclopropyl-8-((R)-2-hydroxy-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one, slower eluting diastereomer from chiral SFC separation using Chiralcel AS column | LC/MS, $(M + 1)^+$: 481 |
| 71 | 4B, 46 | 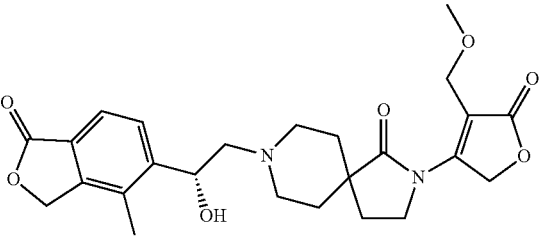  (R)-8-(2-hydroxy-2-(4-methyl-1-oxo-1,3-dihydroisobenzofuran-5-yl)ethyl)-2-(4-(methoxymethyl)-5-oxo-2,5-dihydrofuran-3-yl)-2,8-diazaspiro[4.5]decan-1-one | LC/MS, $(M + 1)^+$: 471 |
| 72 | 4B, 47 | 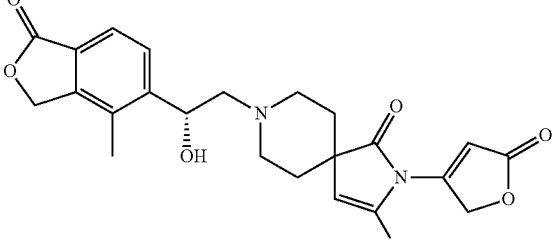  (R)-8-(2-hydroxy-2-(4-methyl-1-oxo-1,3-dihydroisobenzofuran-5-yl)ethyl)-3-methyl-2-(5-oxo-2,5-dihydrofuran-3-yl)-2,8-diazaspiro[4.5]dec-3-en-1-one | LC/MS, $(M + 1)^+$: 439 |
| 73 | 4B, 48 | 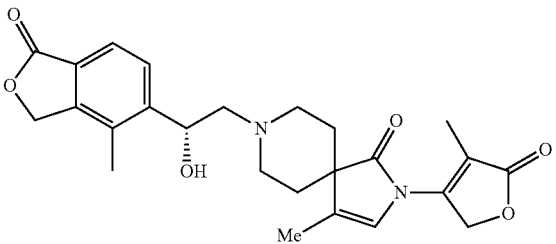  (R)-8-(2-hydroxy-2-(4-methyl-1-oxo-1,3-dihydroisobenzofuran-5-yl)ethyl)-4-methyl-2-(4-methyl-5-oxo-2,5-dihydrofuran-3-yl)-2,8-diazaspiro[4.5]dec-3-en-1-one | LC/MS, $(M + 1)^+$: 453 |

TABLE 4-continued

| EXAMPLE | Intermediates | EXAMPLE STRUCTURE/NAME | Characterization |
|---|---|---|---|
| 74 75 | 49, 17 | 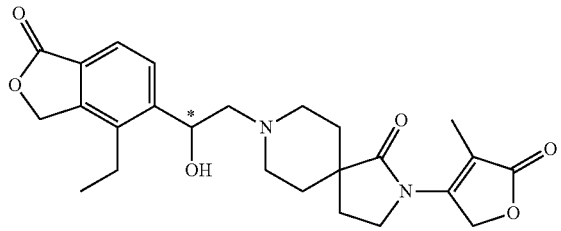<br>(S)-8-(2-(4-ethyl-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one, and (R)-8-(2-(4-ethyl-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one; 74: faster eluting, 76: slower eluting, SFC Column: Chiralpak AD-3 | LC/MS, (M + 1)+: 455 for each isomer |
| 76 77 | 50, 17 | 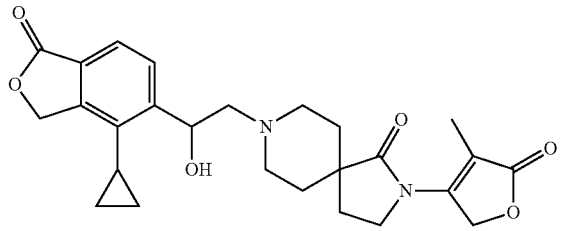<br>(S)-8-(2-(4-cyclopropyl-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one, and (R)-8-(2-(4-cyclopropyl-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one,; 76: faster eluting, 77: slower eluting, SFC Column: Chiralpak AD-3 | LC/MS, (M + 1)+: 467 for each isomer |
| 78 79 | 51, 17 | 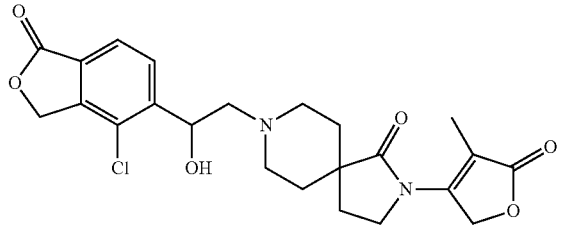<br>(S)-8-(2-(4-cyclopropyl-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one, and (R)-8-(2-(4-chloro-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one; 78: faster eluting, 79: slower eluting, SFC Column: Chiralpak AD-3 | LC/MS, (M + 1)+: 461 for each isomer |
| 80 81 | 52, 17 | 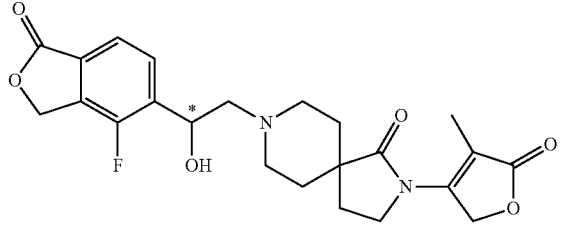<br>8-(2-(4-fluoro-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one; 80: faster eluting, 81: slower eluting, SFC Chiral chromatography | LC/MS, (M + 1)+: 445 for each isomer |

TABLE 4-continued

| EXAMPLE | Intermediates | EXAMPLE STRUCTURE/NAME | Characterization |
|---|---|---|---|
| 82 | 4B, 53 | (1R,3'R,5S)-9-((R)-2-hydroxy-2-(4-methyl-1-oxo-1,3-dihydroisobenzofuran-5-yl)ethyl)-1'-(4-methyl-5-oxo-2,5-dihydrofuran-3-yl)-3-oxa-9-azaspiro[bicyclo[3.3.1]nonane-7,3'-pyrrolidin]-2'-one | LC/MS, (M + 1)+: 483 |
| 83 | 4B, 54 (cis) | 8-((R)-2-hydroxy-2-(4-methyl-1-oxo-1,3-dihydroisobenzofuran-5-yl)ethyl)-6-methoxy-2-(4-methyl-5-oxo-2,5-dihydrofuran-3-yl)-2,8-diazaspiro[4.5]decan-1-one | LC/MS, (M + 1)+: 471 |

EXAMPLE 84A and 84B (Separated Single Isomers)

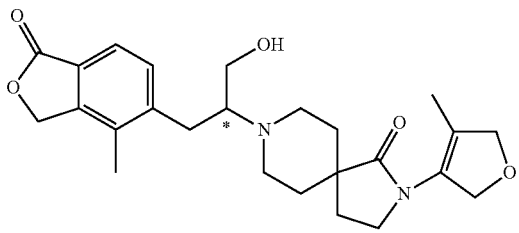 [SMILES: CC1=C(N2CCC3(CCN(C(CO)Cc4ccc5c(c4C)COC5=O)CC3)C2=O)COC1]

(S)-8-(1-hydroxy-3-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one and
(R)-8-(1-hydroxy-3-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one Step A: 5-(2,3-dihydroxypropyl)-4-methylisobenzofuran-1(3H)-one: To a solution of 4-methyl-5-prop-2-en-1-yl-2-benzofuran-1(3H)-one (see step A for 1-3), (2.00 g, 10.6 mmol) in acetone (30 mL) and water (10 mL) was added OsO₄ (0.27 g, 1.06 mmol) and NMO (6.70 g, 11.7 mmol), the solution was stirred at 25° C. for 18 h. The reaction mixture was diluted with water (30 mL) and the aqueous layer was extracted with CH₂Cl₂ (3×40 mL). The organic layers were combined, washed with brine (2×40 mL), dried with MgSO₄, filtered and concentrated. The residue was purified by flash column chromatography (0-10% methanol in dichloromethane) to give the title compound.

Step B: 5-(3-((tert-butyldimethylsilyl)oxy)-2-hydroxypropyl)-4-methylisobenzofuran-1(3H)-one: To a solution of 5-(2,3-dihydroxypropyl)-4-methylisobenzofuran-1(3H)-one (2.00 g, 9.0 mmol) in dry DMF (20 mL) was added imidazole (1.20 g, 18.0 mmol) and TBSCl (1.50 g, 9.9 mmol). After stirring at 25° C. for 2.5 h, the reaction mixture was diluted with CH₂Cl₂ (50 mL) and washed with H₂O (3×20 mL) and saturated NaHCO₃ (3×20 mL). The combined aqueous layers were extracted five times with CH₂Cl₂ (20 mL). The combined organic layers were washed with brine (3×30 mL), dried over Na₂SO₄, filtered and concentrated. The residue was purified by flash column chromatography (0-60% ethyl acetate in petroleum ether) to give the title compound.

Step C: 5-(3-((tert-butyldimethylsilyl)oxy)-2-oxopropyl)-4-methylisobenzofuran-1(3H)-one: To a solution of 5-(3-((tert-butyldimethylsilyl)oxy)-2-hydroxypropyl)-4-methylisobenzofuran-1(3H)-one (1.00 g, 3.0 mmol) in CH₂Cl₂ (30 mL) was added Dess-Martin periodinane (6.30 g, 15.0 mmol). After stirring at 25° C. for 12 h, the reaction mixture was filtered through a short pad of SiO₂ with CH₂Cl₂ (100 mL) as the eluting solvent. After concentrating, the residue was purified by flash column chromatography (0-60% ethyl acetate in petroleum ether) to give the title compound.

Step D: 8-(1-((tert-butyldimethylsilyl)oxy)-3-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one: To a solution of 5-(3-((tert-butyldimethylsilyl)oxy)-2-oxopropyl)-4-methylisobenzofuran-1(3H)-one (0.50 g, 1.5 mmol) in methanol (20 mL) was added 2-(4-methyl-5-oxo-2,5-dihydrofuran-3-yl)-2,8-diazaspiro[4.5]decan-1-one (I-17) (0.45 g, 1.8 mmol) and titanium(IV) isopropoxide (2.10 g, 7.5 mmol). After stirring at for room temperature 48 h, sodium cyanoborohydride (190 mg, 3.0 mmol) was added and the reaction mixture was stirred at room temperature for 20 h. The reaction mixture was quenched with water (10 mL), and the resulting inorganic precipitate was filtered off and washed with methanol (50 mL). The filtrate was then concentrated and the crude product was dissolved in ethyl acetate, filtered to remove the remaining inorganic solids, and concentrated. The residue was purified by flash column chromatography (0-10% methanol in dichloromethane) to give the title compound. LC-MS (ESI, m/z): 569 [M+1]$^+$.

Step E: 8-(1-hydroxy-3-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one: To a solution of 8-(1-(((tert-butyldimethylsilyl)oxy)-3-(4-methyl-1-oxo-1,3-dihydro isobenzofuran-5-yl)propan-2-yl)-2-(4-methyl-5-oxo-2,5-dihydrofuran-3-yl)-2,8-diazaspiro[4.5]decan-1-one (0.10 g, 0.18 mmol) in DCM (3 mL) was added trifluoroacetic acid (3 mL) at 0° C. After stirring at room temperature for 24 h, solvent was removed under reduced pressure and the residue was purified by preparative-HPLC to give the title compound, which was separated by SFC chiral chromatography into two single enantiomers Isomer A (faster eluting) and Isomer B (slower eluting. Column: CHIRALPAK AD 250×30 mm I.D., 20 μm; Mobile phase: Supercritical CO$_2$EtOH (0.2% NH$_3$H$_2$O)=45/55; Flow rate: 80 ml/min. For both isomers: LC-MS (ESI, m/z): 455 [M+1]$^+$.

EXAMPLE 85A and 85B (Separated Single Isomers)

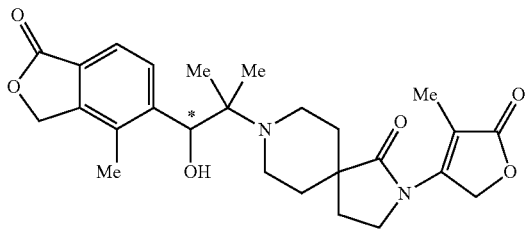 [SMILES: CC1=C(N2CCC3(CCN(C(C)(C)C(O)c4ccc5c(c4C)COC5=O)CC3)C2=O)COC1=O]

(S)-8-(1-hydroxy-2-methyl-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one, and
(R)-8-(1-hydroxy-2-methyl-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one Step A: 2,8-diazaspiro[4.5]decan-1-one: To a solution of tert-butyl 1-oxo-2,8-diazaspiro[4.5]decane-8-carboxylate (I-11) (5.0 g, 19.7 mmol) in methylene chloride (10 mL) was added trifluoroacetic acid (15.2 mL, 197 mmol) and the resulting solution was stirred at rt for 1 h. After evaporating the volatiles the residue was basified on ion exchange column washed with methanol followed by 1 N ammonia in methanol to give 2,8-diazaspiro[4.5]decan-1-one. LC/MS: (M+1)$^+$: 155.11

Step B: ethyl 2-methyl-2-(1-oxo-2,8-diazaspiro[4.5]decan-8-yl)propanoate: A mixture of 2,8-diazaspiro[4.5]decan-1-one (3.03 g, 19.65 mmol), triethylamine (5.48 ml, 39.3 mmol) and ethyl 2-bromo-2-methylpropanoate (5.77 ml, 39.3 mmol) was heated at 80° C. overnight. The reaction mixture was partitioned between methylene chloride (200 mL) and saturated sodium bicarbonate, the alkaline phase was extracted with methylene chloride (3×100 mL). The combined organic phase was dried over magnesium sulfate, concentrated and the residue was purified on silica gel using methanol/methylene chloride to give the title compound. LC/MS (M+1)$^+$: 269.4

Step C: 2-methyl-2-(1-oxo-2,8-diazaspiro[4.5]decan-8-yl)propanal: To a solution of ethyl 2-methyl-2-(1-oxo-2,8-diazaspiro[4.5]decan-8-yl)propanoate (3.77 g, 14.1 mmol) in toluene (100 mL) at −78° C. was added DIBAL-H (45.0 mL, 45.0 mmol) dropwise. After 2 h, the reaction was quenched by addition of methanol (10 mL) dropwise, after warmed to rt, 30 mL of saturated sodium sulfate solution was added and the mixture was vigorously stirred at rt for 1 h. After filtration, the filtrate and the filter cake were partitioned between DCM and saturated sodium bicarbonate, the alkaline phase was extracted with DCM three times, the combined organic phase was dried over sodium sulfate, concentrated to give the title compound. LC/MS (M+1+18)$^+$: 243.3; (M+1+32)$^+$: 257.4.

Step D: 4-methyl-5-(trimethylstannyl)isobenzofuran-1(3H)-one: The a solution of 4-methyl-1-oxo-1,3-dihydroisobenzofuran-5-yltrifluoromethanesulfonate (5.0 g, 16.9 mmol), lithium chloride (4.29 g, 101 mmol), and tetrakis(triphenylphosphine)palladium(0) (1.951 g, 1.688 mmol) in dioxane (30 ml) in sealed tube was degassed with nitrogen for 0.5 h before addition of hexamethylditin (5.25 mL, 25.3 mmol), the tube was sealed and heating at 100° C. overnight. After filtration through CELITE®, the filtrate was concentrated and the residue was purified silica gel column using ethyl acetatehexane to give 4-methyl-5-(trimethylstannyl)isobenzofuran-1(3H)-one. LC/MS: (M+1)$^+$: 308.99; 310.87; 312.78.

Step E: 5-bromo-4-methylisobenzofuran-1(3H)-one: To a solution of 4-methyl-5-(trimethylstannyl)isobenzofuran-1(3H)-one (4.37 g, 14.05 mmol) in DCM (20 mL) was added bromine (0.796 ml, 15.46 mmol) at 0° C. The reaction mixture was stirred at 0° C. for 0.5 h. Saturated thiosulfate solution was added and the mixture was extracted with methylene chloride (2×100 mL), the combined organic phase was dried over sodium sulfate, concentrated to give 5-bromo-4-methylisobenzofuran-1(3H)-one. LC/MS: (M+1)$^+$: 226.89; 228.89.

Step F: 5-bromo-4-methyl-1,3-dihydroisobenzofuran-1-ol: To a solution of 5-bromo-4-methylisobenzofuran-1(3H)-one (3.45 g, 15.19 mmol) in toluene (100 mL) at −78° C. was added DIBAL-H (21.27 mL, 21.27 mmol) dropwise. After stirring at −78° C. for 2 h, the reaction was quenched by methanol at −78° C., then warmed to rt, then 20 mL of saturated sodium sulfate was added and the mixture was vigorously stirred at rt for 30 min. Next, the mixture was filtered and washed with ethyl acetate. The filtrate was washed with saturated sodium bicarbonate, dried over sodium sulfate, then concentrated to give the title compound. LC/MS: (M−17)$^+$: 210.92; 212.91.

Step G: ((5-bromo-4-methyl-1,3-dihydroisobenzofuran-1-yl)oxy)(tert-butyl)dimethylsilane
A solution of TBS-Cl (3.63 g, 24.10 mmol) in methylene chloride (15 mL) was added to a solution of 5-bromo-4-methyl-1,3-dihydroisobenzofuran-1-ol (2.76 g, 12.1 mmol) and imidazole (1.72 g, 25.3 mmol) in methylene chloride (80 mL) at 0° C., the resulting solution was stirred at rt overnight. The mixture was partitioned between DCM and water, the water phase was extracted with methylene chloride and the combined organic phase was dried over sodium sulfate then concentrated, and the residue was purified on silica gel column using ethyl acetatehexane to give the title compound. LC/MS: (M−131)$^+$: 210.91; 212.91.

Step H: 8-(1-(1-(((tert-butyldimethylsilyl)oxy)-4-methyl-1,3-dihydroisobenzofuran-5-yl)-1-hydroxy-2-methylpropan-2-yl)-2,8-diazaspiro[4.5]decan-1-one: To a solution of ((5-bromo-4-methyl-1,3-dihydroisobenzofuran-1-yl)oxy)(tert-butyl)dimethylsilan (3.9 g, 11.36 mmol) in tetrahydrofuran (50 ml) at −78° C. was added N-butyllithium (5.00 ml, 12.50 mmol). After 15 min, 2-methyl-2-(1-oxo-2,8-diazaspiro[4.5]decan-8-yl)propanal (0.892 g, 3.98 mmol) was added in one portion. The resulting solution was stirred at −78° C. for 3.5 h before being quenched by addition of methanol (6 mL) and saturated sodium bicarbonate (100 mL). The mixture was extracted with 30% isopropanol/methylene chloride (3×100 mL). The combined organic phase was dried over sodium sulfate, concentrated and the residue was purified on silica gel using methanol/methylene chloride to give the title compound. LC/MS: (M+1)$^+$: 489.15.

Step I: 8-(1-(1-(((tert-butyldimethylsilyl)oxy)-4-methyl-1,3-dihydroisobenzofuran-5-yl)-1-hydroxy-2-methylpropan-2-yl)-2-(4-methyl-5-oxo-2,5-dihydrofuran-3-yl)-2,8-diazaspiro[4.5]decan-1-one: To a mixture of 8-(1-(1-(((tert-butyldimethylsilyl)oxy)-4-methyl-1,3-dihydroisobenzofuran-5-yl)-1-hydroxy-2-methylpropan-2-yl)-2,8-diazaspiro[4.5]decan-1-one (1.35 g, 2.76 mmol), 4-methyl-5-oxo-2,5-dihydrofuran-3-yl trifluoromethanesulfonate (I-9) (0.884 g, 3.59 mmol) in toluene (40 mL) was added potassium carbonate (0.764 g, 5.52 mmol), Xantphos (0.320 g, 0.552 mmol), and water (0.149 mL, 8.29 mmol). The mixture was flushed with nitrogen for 20 min before addition of palladium (II) acetate (0.062 g, 0.276 mmol). The resulting mixture was heated at 70° C. overnight. After filtration the filtrate was concentrated and the residue was purified on silica gel column using methanol/methylene chloride as eluting solvents to give the title compound. LC/MS: (M+1−114)$^+$:471.22.

Step J: 8-(1-hydroxy-1-(1-hydroxy-4-methyl-1,3-dihydroisobenzofuran-5-yl)-2-methylpropan-2-yl)-2-(4-methyl-5-oxo-2,5-dihydrofuran-3-yl)-2,8-diazaspiro[4.5]decan-1-one: To a solution of the product of Step I (1.282 g, 2.192 mmol) in tetrahydrofuran (50 ml) was added TBAF (2.63 mL, 2.63 mmol) at 0° C., and the resulting solution was stirred at 0° C. for 2 h. After concentration, the residue was purified on TLC eluting with 10% MeOH/DCM to give the title compound. LC/MS: (M+1)$^+$: 471.20.

Step K: 8-(1-hydroxy-2-methyl-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one: To a solution of the product of Step J (340 mg, 0.723 mmol) in methylene chloride (30 mL) was added PCC (311 mg, 1.45 mmol) at 0° C. and the resulting solution was stirred at 0° C. for 2 h. The reaction mixture was partitioned between methylene chloride and saturated bicarbonate, and the alkaline phase was extracted with methylene chloride (3×50 mL). The combined organic phase was dried over sodium sulfate, concentrated and the residue was purified on TLC using 10% methanol/methylene chloride as developing solvents to give the title compound. LC/MS: (M+1)$^+$: 469.20.

Step L: 8-(1-hydroxy-2-methyl-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one (separated single isomers): The title compound (an isomer mixture) (100 mg, 0.213 mmol) was separated by SFC on OJ column to give two isomers. Isomer A (faster eluting): LC/MS: (M+1)$^+$: 469.25; $^1$HNMR (500 MHz, CDCl$_3$), δ 7.766-7.289 (m, 2H), 5.287 (s, 2H), 5.261(s, 2H), 5.139 (s, 1H), 4.072-4.044(t, J=7.1 Hz, 2H), 3.190-3.088(m, 2H), 2.545-2.506(m, 2H), 2.341(s, 3H), 2.191-2.162(m, 2H), 2.066-2.037(m, 2H), 1.695-1.670(m, 2H), 0.985(s, 3H), 0.956(s, 3H). Isomer B (slower eluting), LC/MS: (M+1)$^+$: 469.25. $^1$HNMR (500 MHz, CDCl$_3$), δ7.825-7.768(m, 2H), 5.289(s, 2H), 5.262(s, 2H), 5.138(s, 1H), 4.073-4.044(t, J=6.9 Hz, 2H), 3.191-3.086(m, 2H), 2.592-2.502(m, 2H), 2.341(s, 3H), 2.191-2.162(m, 2H), 2.066-2.037(m, 2H), 1.695-1.670(m, 2H), 0.985(s, 3H), 0.956(s, 3H).

The following Thallium Flux Assay and/or the Electrophysiology Assay were performed on each of the final product compounds in the Examples unless otherwise noted in an Example.

Thallium Flux Assay

Cell Culture Conditions—HEK293 cells stably expressing hROMK (hK$_{ir}$1.1) were grown at 37° C. in a 10% CO$_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./CO$_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100×after solubilization in 1 mL water. Store at 4° C.
  FluxOR™ Chloride-free Buffer (Component E)—5× Concentrate
  Potassium sulfate (K$_2$SO$_4$) Concentrate (Component F)—125 mM in water. Store at 4° C.
  Thallium sulfate (Tl$_2$SO$_4$) Concentrate (Component G)—50 mM in water. Store at 4° C.
  DMSO (dimethyl sulfoxide, Component H)—1 mL (100%)

Reagent Preparation: FluxOR Working Solutions
  1000× FluxOR™ Reagent: Reconstitute a vial of component A in 100 µl DMSO; Mix well; Store 10 µl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 mL of 1× FluxOR™ Assay Buffer; 1 mL of reconstituted component D; Store at 4° C.
  Loading Buffer (per microplate): 10 µl 1000× FluxOR™ Reagent; 100 µl component C; 10 mL Probenecid/Assay Buffer
  Compound Buffer (per microplate): 20 mL Probenecid/Assay Buffer; 0.3 mM ouabain (10 mM ouabain in water can be stored in amber bottle/aluminum foil at room temperature); Test compound
  1× FluxOR™ Chloride-Free Buffer: Prepare 1× working solution in water. Can be stored at room temperature
  Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium 0.3 mM Potassium). Store at 4° C. when not in use. If kept sterile, this solution is good for months.

Assay Protocol—The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 μA at 20,000 cells/well) in 384-well PDL coated Microplates
2. Allow cells to adhere overnight in humidified 37° C./10% $CO_2$ incubator
3. Completely remove cell growth media from microplate and replace with 25 μl loading buffer
4. Incubate Microplate at room temperature, protected form light, for 90 min
5. Remove loading buffer and replace with 25 μl 1× Assay Buffer±test compound.
6. Incubate microplate at room temperature, protected from light, for 30 min
7. At FLIPR-Tetra 384: Add stimulant (Thallium/Potassium) solution to microplate and monitor fluorescence. Excitation=400 nm, Emission=460 & 580 nm. Collect data for 10 min.

Data Calculation—The fluorescence intensity of wells containing 3 μM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 μM in this assay. Alternatively, the control could be another compound (outside the scope of Formula I) that has an $IC_{50}$ potency in this assay of less than 1 μM.

Electrophysiology Assay

Block of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 mL of Versene (Invitrogen 15040-066) for approximately 6 min at 37° C. and suspended in 10 mL of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 mL of bath solution and placed in the IonWorks instrument. The intracellular solution consisted of (in mM): 80 K gluconate, 40 KCl, 20 KF, 3.2 $MgCl_2$, 3 EGTA, 5 Hepes, pH 7.4. Electrical access to the cytoplasm was achieved by perforation in 0.13 mg/mL amphotericin B for 4 min. Amphotericin B (Sigma A-4888) was prepared as a 40 mg/mL solution in DMSO. Voltage protocols and current recordings were performed using the IonWorks HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control can be any compound of Formulas I-V of the present invention, preferably with an $IC_{50}$ potency of less than 1 μM in this assay. Alternatively, the control could be another compound (outside the scope of Formulas I-V) that has an $IC_{50}$ potency in this assay of less than 1 μM.

Data collected for compounds in the Examples of the present invention using the Thallium Flux Assay and the Electrophysiology Assay are shown in Table 5 below. All of the tested final product compounds in the Examples (diastereomeric mixtures and individual diastereomers) had $IC_{50}$ potencies less than 1 μM in one or both of the Thallium Flux Assay and the Electrophysiology Assay.

TABLE 5

| EXAMPLE No. | Thallium Flux $IC_{50}$ (μM) | Electrophysiology $IC_{50}$ (μM) |
|---|---|---|
| 1 | 0.01 | |
| 2 | 0.05 | |
| 3 | 0.29 | 0.07 |
| 5 | 0.03 | 0.004 |
| 6 | 0.03 | |
| 6A | 0.02 | |
| 6B | 0.01 | |
| 7 | 0.02 | 0.01 |
| 8 | 0.03 | |
| 9 | 0.01 | 0.01 |
| 10 | 0.20 | 0.03 |
| 11 | 0.12 | 0.02 |
| 12 | 0.14 | 0.03 |
| 13 | 0.49 | 0.06 |
| 14 | 0.38 | 0.10 |
| 15 | 0.17 | 0.05 |
| 16 | 0.11 | |
| 17 | 0.08 | 0.02 |
| 18 | 0.02 | 0.004 |
| 19 | 0.04 | |
| 20 | 0.01 | |
| 21 | 0.37 | 0.39 |
| 22 | 0.03 | 0.004 |
| 23 | 0.02 | 0.01 |
| 24 | 0.24 | 0.62 |
| 25 | 0.01 | 0.01 |
| 26 | 0.23 | |
| 27 | 0.21 | |
| 28 | 0.19 | |
| 29 | 0.07 | |
| 30 | 0.02 | 0.02 |
| 31 | 0.04 | |
| 34 | 0.09 | |
| 35 | 0.07 | |
| 36 | 0.03 | |
| 37 | 0.03 | |

TABLE 5-continued

| EXAMPLE No. | Thallium Flux IC$_{50}$ (μM) | Electrophysiology IC$_{50}$ (μM) |
|---|---|---|
| 38 | 0.02 | |
| 39 | 0.02 | |
| 40 | 0.02 | |
| 41 | 0.24 | |
| 42 | 0.10 | |
| 43 | 0.03 | |
| 44 | 0.04 | |
| 45 | 0.16 | |
| 46 | 0.14 | |
| 47 | 0.04 | |
| 48 | 0.02 | |
| 49 | 0.04 | |
| 50 | 0.03 | |
| 51 | 0.31 | 0.02 |
| 52 | 0.35 | 0.06 |
| 53A | 0.01 | |
| 53B | 0.05 | |
| 53C | 0.01 | 0.01 |
| 53D | 0.07 | |
| 54 | 0.15 | |
| 55 | 0.25 | |
| 56 | 0.37 | |
| 57 | 0.32 | |
| 58 | 0.22 | |
| 59 | 0.21 | |
| 60 | 0.10 | |
| 65 | 0.04 | |
| 66 | 0.01 | 0.02 |
| 67 | 0.02 | 0.02 |
| 69 | 0.02 | 0.03 |
| 70 | 0.34 | |
| 71 | 0.07 | |
| 72 | 0.03 | |
| 73 | 0.08 | |
| 74 | 0.20 | |
| 75 | 0.03 | 0.01 |
| 76 | 0.01 | 0.01 |
| 77 | 0.24 | |
| 78 | 0.27 | |
| 79 | 0.01 | 0.003 |
| 80 | 0.05 | 0.01 |
| 81 | 0.19 | |
| 82 | 0.18 | |
| 83 | 0.04 | 0.05 |
| 84A | 0.06 | |
| 84B | 0.07 | |
| 85A | 0.12 | |
| 85B | 0.01 | |

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneuously hypertensive rats (SHR):

Spontaneously hypertensive rats (SHR, male, 6 months, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. HCTZ (25 mg/kg/day, PO) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis. Example numbers 5, 7, 9 and 43 were evaluated at PO, QD doses at one or more doses within the range of 0.3 to 10 mg/kg and resulted in typical reductions in daily (24 h) mean systolic blood pressure ranging from 6 mmHg to 24 mmHg at the doses used by the last day of the studies.

The Spontaneously Hypertensive Rat Assay is well known and often used in the art as an experimental model simulating human hypertension (see, e.g., Lerman, L. O., et al., *J Lab Clin Med*, 2005; 146:160-173).

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A method for the treatment of one or more disorders selected from hypertension, acute heart failure, chronic heart failure or pulmonary arterial hypertension in a patient in need thereof by administering to the patient a therapeutically effective amount of a compound having structural Formula I

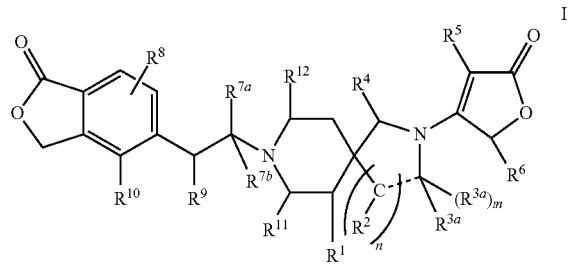

or a pharmaceutically acceptable salt thereof wherein:
$R^1$ is —H, halo, —OH, or —OC$_{1-3}$alkyl;
m is an integer selected from zero ($R^{3b}$ is absent) and 1 ($R^{3b}$ is present);
n is an integer selected from 1 or 2;
$R^2$ is independently selected at each occurrence from —H, =O (oxo), —OH, —C$_{1-3}$alkyl or —OC$_{1-3}$alkyl, provided that when n is 2, then at least one $R^2$ is —H;
$R^{3a}$ is —H, =O, —C$_{3-4}$cycloalkyl or —C$_{1-3}$alkyl optionally substituted with —OCH$_3$ or 1 to 3 of —F, provided that only one of $R^2$ or $R^{3a}$ can be =O, $R^{3b}$ is —H or —$C_{1-3}$alkyl, or $R^{3b}$ is absent when $R^{3a}$ is =O or when the dashed bond is a double bond or an aromatic bond;

$R^4$ is —H or =O;

$R^5$ is (a) —H, (b) halo, (c) —$C_{1-3}$alkyl optionally substituted with —O—$C_{1-3}$alkyl, or (d) —$C_{3-6}$cycloalkyl;

$R^6$ is —H or —$C_{1-3}$alkyl;

$R^{7a}$ is —H or —$C_{1-3}$alkyl optionally substituted with —OH, —OCH$_3$ or 1 to 3 of —F;

$R^{7b}$ is —H or —$C_{1-3}$alkyl;

$R^8$ is —H, halo or —$C_{1-3}$alkyl;

$R^9$ is —H, —F, —OH, —OC$_{1-3}$alkyl, —CH$_2$OH, —NH—$R^{13}$ or

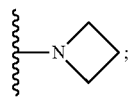

$R^{10}$ is —H, halo, —CN, —$C_{3-4}$ cycloalkyl, or —$C_{1-3}$alkyl optionally substituted with 1 to 3 of —F;

or $R^9$ is —O— and is joined together with $R^{10}$ to represent —CH$_2$—CH$_2$—O—;

$R^{11}$ is —H, —CH$_2$OH, —CH$_2$OCH$_3$, or —$C_{1-3}$alkyl optionally substituted with 1 to 3 of —F;

$R^{12}$ is —H, —CH$^2$OH, —CH$^2$OCH$^3$, or —$C^{1-3}$alkyl optionally substituted with 1 to 3 of —F;

or $R^{11}$ and $R^{12}$ are joined together to represent —CH$_2$—CH$_2$—, —CH$_2$—N(CH$_3$)—CH$_2$— or —CH$_2$OCH$_2$—;

$R^{13}$ is —H, —(CH$_2$)$_{0-2}$—$C_{3-6}$cycloalkyl, —(CH$_2$)$_{1-2}$—OC$_{3-6}$cycloalkyl, —(CH$_2$)$_{1-2}$—OC$_{3-6}$cycloalkyl, —(CH$_2$)$_{1-2}$—OC$_{1-3}$alkyl, —(CH$^2$)$_{1-2}$—CN, —C(O)OC$_{1-3}$alkyl, —SO$_2$CH$_3$ or —$C_{1-3}$alkyl optionally substituted with one to three of —F; and the dashed bond ("- - -") represents a single, double or aromatic bond, provided that (A) when n is 2, then the dashed bond is a single bond and m is 1; and (B) when n is 1 and
(i) m is 1, or
(ii) $R^{3a}$ is =O and m is zero,
then the dashed bond is a single bond; and (C) when n is 1, m is zero, $R^2$ is not =O and $R^{3a}$ is not =O, then the dashed bond is a double bond.

2. The method of claim 1 wherein the compound has structural Formula II or III or a pharmaceutically acceptable salt thereof:

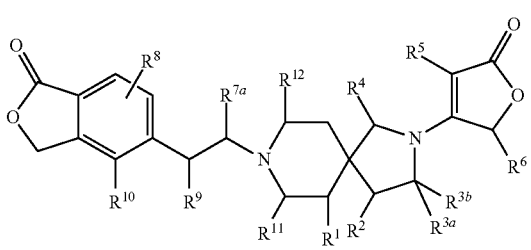

II

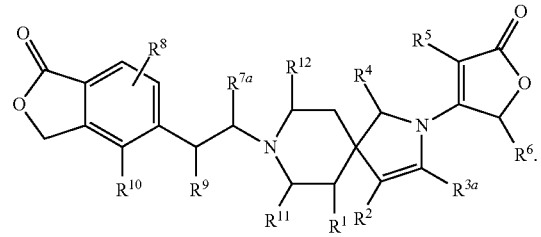

III

3. The method of claim 2 wherein: $R^{3a}$ is —H or —CH$_3$; $R^4$ is =O; $R^5$ is —H or —CH$_3$; $R^{7a}$ is —H or CH$_3$; $R^9$ is —H, —OH, —OCH$_3$ or —NH$_2$; and $R^{10}$ is —H or —CH$_3$.

4. The method of claim 3 wherein $R^9$ is —OH; and $R^{10}$ is —CH$_3$.

5. The method of claim 1 wherein the compound has structural Formula IV or a pharmaceutically acceptable salt thereof:

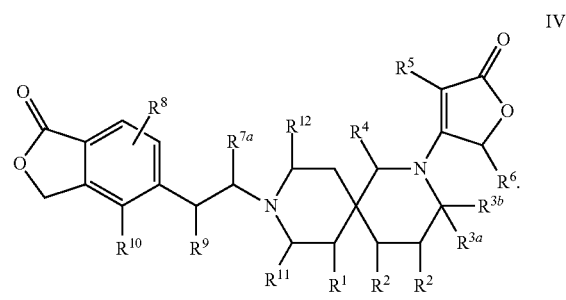

IV

6. The method of claim 5 wherein: $R^{3a}$ is —H or —CH$_3$; $R^4$ is =O; $R^5$ is —H or —CH$_3$; $R^{7a}$ is —H or CH$_3$; $R^9$ is —H, —OH, —OCH$_3$ or —NH$_2$; and $R^{10}$ is —H or —CH$_3$.

7. The method of claim 6 wherein $R^9$ is —OH; and $R^{10}$ is —CH$_3$.

8. The method of claim 1 wherein the compound is:

8-(2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one;

(S)8-((R)-2methoxy 2(4-methyl-1-oxo-1,3-dihydroisobenzofuran-5-yl)ethyl)-3-methyl-2-(5-oxo-2,5-dihydrofuran-3-yl)-2,8-diazaspiro[4.5]decan-1-one;

8-[2-(1-oxo-1,3-dihydro-2-benzofuran-5-yl)ethyl]-2-(5-oxo-2,5-dihydrofuran-3-yl)-2,8-diazaspiro[4.5]decan-1-one;

(S)-3-methyl-8-(2-(4-methyl-1-oxo-1,3-dihydroisobenzofuran-5-yl)ethyl)-2-(5-oxo-2,5-dihydrofuran-3-yl)-2,8-diazaspiro[4.5]decan-1-one;

8-[(2R)-2-hydroxy-2-(4-methyl-1-oxo-1,3-dihydro-2-benzofuran-5-yl)ethyl]-2-(5-oxo-2,5-dihydrofuran-3-yl)-2,8-diazaspiro[4.5]decan-1-one;

(R)-8-((R)-2-hydroxy-2-(4-methyl-1-oxo-1,3-dihydroisobenzofuran-5-yl)ethyl)-3-methyl-2-(5-oxo-2,5-dihydrofuran-3-yl)-2,8-diazaspiro[4.5]decan-1-one;

(S)-8-((R)-2-hydroxy-2-(4-methyl-1-oxo-1,3-dihydroisobenzofuran-5-yl)ethyl)-3-methyl-2-(5-oxo-2,5-dihydrofuran-3-yl)-2,8-diazaspiro[4.5]decan-1-one:

8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one;

8-[(2S)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one;

9-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-9-azoniaspiro[5.5]undecane;

5-{(1R)-1-hydroxy-2-[2(5-oxo-2,5-dihydrofuran-3-yl)-2,8-diazaspiro[4.5]dec-8-yl]ethyl}-4-methyl-2-benzofuran-1(3H)-one;

8-[(2R)-2-hydroxy-2-(4-methyl-1-oxo-1,3-dihydro-2-benzofuran-5-yl)ethyl]-2-(2-methyl-5-oxo-2,5-dihydrofuran-3-yl)-2,8-diazaspiro[4.5]decan-1-one;

2-(2,4-dimethyl-5-oxo-2,5-dihydrofuran-3-yl)-8-[(2R)-2-hydroxy-2-(4-methyl-1-oxo-1,3-dihydro-2-benzofuran-5-yl)ethyl]-2,8-diazaspiro[4.5]decan-1-one;

8-[(2R)-2-hydroxy-2-(4-methyl-1-oxo-1,3-dihydro-2-benzofuran-5-yl)ethyl]-2(5-oxo-2,5-dihydrofuran-3-yl)-2,8-diazaspiro[4.5]decan-3-one;

8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-3-one;

2-(4-ethyl-5-oxo-2,5-dihydrofuran-3-yl)-8-[(2R)-2-hydroxy-2-(4-methyl-1-oxo-1,3-dihydro-2-benzofuran-5-yl)ethyl]-2,8-diazaspiro[4.5]decan-1-one;

(1R,3r,5S)-8-[(2R)-2-hydroxy-2-(4-methyl-1-oxo-1,3-dihydro-2-benzofuran-5-yl)ethyl]-1'-(5-oxo-2,5-dihydrofuran-3-yl)-2'H-spiro[8-azabicyclo[3.2.1]octane-3,3'-pyrrolidin]-2'-one;

(1R,3r,5S)-8-[(2R)-2-hydroxy-2-(4-methyl-1-oxo-1,3-dihydro-2-benzofuran-5-yl)ethyl]-1'-(4-methyl-5-oxo-2,5-dihydrofuran-3-yl)-2'H-spiro[8-azabicyclo[3.2.1]octane-3,3'-pyrrolidin]-2'-one;

(1R,3s,5S)-8-((R)-2-hydroxy-2-(4-methyl-1-oxo-1,3-dihydroisobenzofuran-5-yl)ethyl)-1'-(4-methyl-5-oxo-2,5-dihydrofuran-3-yl)-8-azaspiro[bicyclo[3.2.1]octane-3,3'-pyrrolidin]-2'-one;

8-[(2S)-2-hydroxy-2-(4-methyl-1-oxo-1,3-dihydro-2-benzofuran-5-yl)ethyl]-2(5-oxo-2,5-dihydrofuran-3-yl)-2,8-diazaspiro[4.5]decan-1-one;

2-(4-fluoro-5-oxo-2,5-dihydrofuran-3-yl)-8-[(2R)-2-hydroxy-2-(4-methyl-1-oxo-1,3-dihydro-2-benzofuran-5-yl)ethyl]-1-oxo-2-aza-8-azoniaspiro[4.5]decane;

9-[(2R)-2-hydroxy-2-(4-methyl-1-oxo-1,3-dihydro-2-benzofuran-5-yl)ethyl]-1-oxo-2-(5-oxo-2,5-dihydrofuran-3-yl)-2-aza-9-azoniaspiro[5.5]undecane;

9-[(2R)-2-hydroxy-2-(4-methyl-1-oxo-1,3-dihydro-2-benzofuran-5-yl)ethyl]-2(5-oxo-2,5-dihydrofuran-3-yl)-2-aza-9-azoniaspiro[5.5]undecane;

2-(4-chloro-5-oxo-2,5-dihydrofuran-3-yl)-8-[(2R)-2-hydroxy-2-(4-methyl-1-oxo-1,3-dihydro-2-benzofuran-5-yl)ethyl]-1-oxo-2-aza-8-azoniaspiro[4.5]decane;

6-hydroxy-8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane;

6-fluoro-8-((R)-2-hydroxy-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one;

8-[(2R)-2-hydroxy-2-(4-methyl-1-oxo-1,3-dihydro-2-benzofuran-5-yl)ethyl]-3-methyl-2-(4-methyl-5-oxo-2,5-dihydrofuran-3-yl)-2,8-diazaspiro[4.5]decan-1-one;

2-(4-cyclopropyl-5-oxo-2,5-dihydrofuran-3-yl)-8-[(2R)-2-hydroxy-2-(4-methyl-1-oxo-1,3-dihydro-2-benzofuran-5-yl)ethyl]-2,8-diazaspiro[4.5]decan-1-one;

4-hydroxy-8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane;

8-((R)-2-hydroxy-2-(4-methyl-1-oxo-1,3-dihydroisobenzofuran-5-yl)ethyl)-4-methoxy-2-(4-methyl-5-oxo-2,5-dihydrofuran-3-yl)-2,8-diazaspiro[4.5]decan-1-one;

8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1,4-dioxo-2-aza-8-azoniaspiro[4.5]decane;

8-[(2S)-2-hydroxy-2-(6-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane;

8-[(2R)-2-hydroxy-2-(6-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane;

(1R,3r,5S)-8-[(2R)-2-hydroxy-2-(4-methyl-1-oxo-1,3-dihydro-2-benzofuran-5-yl)ethyl]-5'-methyl-1-(5-oxo-2,5-dihydrofuran-3-yl)-2'H-spiro[8-azabicyclo[3.2.1]octane-3,3'-pyrrolidin]-2'-one;

(1R,3r,5S)-8-[(2S)-2-hydroxy-2-(4-methyl-1-oxo-1,3-dihydro-2-benzofuran-5-yl)ethyl]-5'-methyl-1'-(5-oxo-2,5-dihydrofuran-3-yl)-2'H-spiro[8-azabicyclo[3.2.1]octane-3,3'-pyrrolidin]-2'-one;

8-[(2R)-2-hydroxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]dec-3-ene;

(R)-8-(2-hydroxy-2-(4-methyl-1-oxo-1,3-dihydroisobenzofuran-5-yl)ethyl)-2-(5-oxo-2,5-dihydrofuran-3-yl)-2,8-diazaspiro[4.5]dec-3-en-1-one;

(1R,3's,5S)-9-[(2R)-2-hydroxy-2-(4-methyl-1,3-dihydro-2-benzofuran-5-ypethyl]-7-methyl-1'-(4-methyl-5-oxo-2,5-dihydrofuran-3-yl)-2'H-spiro[7,9-diazabicyclo[3.3.1]nonane-3,3'-pyrrolidin]-2'-one;

(1R,3's,5S)-9-[(2S)-2-hydroxy-2-(4-methyl-1-oxo-1,3-dihydro-2-benzofuran-5-yl)ethyl]-7-methyl-1'-(4-methyl-5-oxo-2,5-dihydrofuran-3-yl)-2'H-spiro[7,9-diazabicyclo[3.3.1]nonane-3,3'-pyrrolidin]-2'-one;

8-[(2R)-2-fluoro-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one;

8-[(2S)-2-fluoro-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one;

8-[(2R)-2-methoxy-2-(4-methyl-1-oxo-1,3-dihydro-2-benzofuran-5-yl)ethyl]-2-(4-methyl-5-oxo-2,5-dihydrofuran-3-yl)-1-oxo-2-aza-8-azoniaspiro[4.5]decane;

8-[(2R)-2-ethoxy-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one;

8-[(2R)-2-methoxy-2-(4-methyl-1-oxo-1,3-dihydro-2-benzofuran-5-yl)ethyl]-2-(5-oxo-2,5-dihydrofuran-3-yl)-2,8-diazaspiro[4.5]decan-1-one;

1-oxo-2-(5-oxo-2,5-dihydrofuran-3-yl)-8-[(3-oxo-3,6,8,9-tetrahydro-1H-furo[3,4-f]isochromen-6-yl)methyl]-2-aza-8-azoniaspiro[4.5]decane;

8-(1-hydroxy-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one;

8-(2-(cyclopropylamino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one;

8-(2-((2,2-difluoroethyl)amino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5    ]decan-1-one;

8-(2-(cyclobutylamino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one;

8-(2-(azetidin-1-yl)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one;

8-(2-((2-methoxyethyl)amino)-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one;

3-((1-(4-methyl-1-oxo-1,3-dihydroisobenzofuran-5-yl)-2-(2-(4-methyl-5-oxo-2,5-dihydrofuran-3-yl)-1-oxo-2,8-diazaspiro[4.5]decan-8-yl)ethyl)amino)propanenitrile;

8-[2-(methylamino)-2-(4-methyl-1-oxo-1,3-dihydro-2-benzofuran-5-yl)ethyl]-2-(4-methyl-5-oxo-2,5-dihydrofuran-3-yl)-2,8-diazaspiro[4.5]decan-1-one;

(S)-8-(2-amino-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one;

(R)-8-(2-amino-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one;

Methyl {(1R)-1-(4-methyl-1-oxo-1,3-dihydro-2-benzofuran-5-yl)-2-[2-(4-methyl-5-oxo-2,5-dihydrofuran-3-yl)-1-oxo-2,8-diazaspiro[4.5]dec-8-yl]ethyl}carbamate;

(R)-N-(1-(4-methyl-1-oxo-1,3-dihydroisobenzofuran-5-yl)-2-(2-(4-methyl-5-oxo-2,5-dihydrofuran-3-yl)-1-oxo-2,8-diazaspiro[4.5]decan-8-yl)ethyl)methanesulfonamide;

1'-[(2R)-2-hydroxy-2-(4-methyl-1-oxo-1,3-dihydro-2-benzofuran-5-yl)ethyl]-2-oxo-1-(5-oxo-2,5-dihydrofuran-3-yl)-1,2-dihydrospiro[indole-3,4'-piperidinium];

3-ethyl-8-((R)-2-hydroxy-2-(4-methyl-1-oxo-1,3-dihydroisobenzofuran-5-yl)ethyl)-2-(5-oxo-2,5-dihydrofuran-3-yl)-2,8-diazaspiro[4.5]decan-1-one;

3-cyclopropyl-8-((R)-2-hydroxy-2-(4-methyl-1-oxo-1,3-dihydroisobenzofuran-5-yl)ethyl)-2-(5-oxo-2,5-dihydrofuran-3-yl)-2,8-diazaspiro[4.5]decan-1-one;

3-cyclopropyl-8-((R)-2-hydroxy-2-(4-methyl-1-oxo-1,3-dihydroisobenzofuran-5-yl)ethyl)-2-(4-methyl-5-oxo-2,5-dihydrofuran-3-yl)-2,8-diazaspiro[4.5]decan-1-one;

(R)-8-(2-hydroxy-2-(4-methyl-1-oxo-1,3-dihydroisobenzofuran-5-yl)ethyl)-2-(4-(methoxymethyl)-5-oxo-2,5-dihydrofuran-3-yl)-2,8-diazaspiro[4.5]decan-1-one;

(R)-8-(2-hydroxy-2-(4-methyl-1-oxo-1,3-dihydroisobenzofuran-5-yl)ethyl)-3-methyl-2-(5-oxo-2,5-dihydrofuran-3-yl)-2,8-diazaspiro[4.5]dec-3-en-1-one;

(R)-8-(2-hydroxy-2-(4-methyl-1-oxo-1,3-dihydroisobenzofuran-5-yl)ethyl)-4-methyl-2-(4-methyl-5-oxo-2,5-dihydrofuran-3-yl)-2,8-diazaspiro[4.5]dec-3-en-1-one;

8-(2-(4-ethyl-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one;

8-(2-(4-cyclopropyl-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one;

8-(2-(4-chloro-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one;

8-(2-(4-fluoro-1-oxo-1,3-dihydroisobenzofuran-5-yl)-2-hydroxyethyl)-2-(4-methyl-5-oxo-2,5-dihydrofuran-3-yl)-2,8-diazaspiro[4.5]decan-1-one;

(1R,3'R,5S)-9-((R)-2-hydroxy-2-(4-methyl-1-oxo-1,3-dihydroisobenzofuran-5-yl)ethyl)-1'-(4-methyl-5-oxo-2,5-dihydrofuran-3-yl)-3-oxa-9-azaspiro[bicyclo [3.3.1]nonane-7,3'-pyrrolidin]-2'-one;

8-((R)-2-hydroxy-2-(4-methyl-1-oxo-1,3-dihydroisobenzofuran-5-yl)ethyl)-6-methoxy-2-(4-methyl-5-oxo-2,5-dihydrofuran-3-yl)-2,8-diazaspiro[4.5]decan-1-one;

(S)-8-(1-hydroxy-3-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one;

(R)-8-(1-hydroxy-3-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one;

(S)-8-(1-hydroxy-2-methyl-1-(4-methyl-1-oxo-1,3-dihydroisobenzofuran-5-yl)propan-2-yl)-2-(4-methyl-5-oxo-2,5-dihydrofuran-3-yl)-2,8-diazaspiro[4.5]decan-1-one; and (R)-8-(1-hydroxy-2-methyl-1-(4-methyl-1-oxo-1,3-dihydroisobenzofuran-5-yl)propan-2-yl)-2-(4-methyl-5-oxo-2,5-dihydrofuran-3-yl)-2,8-diazaspiro [4.5]decan-1-one;

or a pharmaceutically acceptable salt thereof.

9. The method of claim 1 further comprising administering an active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, trandolapril, amiloride, spironolactone, epleranone, and triamterene, or a pro-drug thereof, or a pharmaceutically acceptable salt of any of the foregoing.

10. A method for inhibiting ROMK in a patient comprising administering to the patient a ROMK-inhibitory effective amount of a compound having structural Formula I

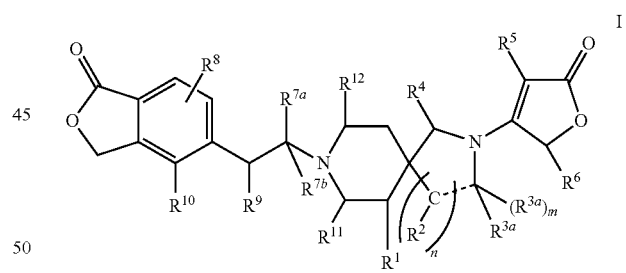

or a pharmaceutically acceptable salt thereof wherein:
$R^1$ is —H, halo, —OH, or —OC$_{1-3}$alkyl;
m is an integer selected from zero ($R^{3b}$ is absent) and 1 ($R^{3b}$ is present);
n is an integer selected from 1 or 2;
$R^2$ is independently selected at each occurrence from —H, =O (oxo), —OH, —C$_{1-3}$alkyl or —OC$_{1-3}$alkyl, provided that when n is 2, then at least one $R^2$ is —H;
$R^{3a}$ is —H, =O —C$_{3-4}$cycloalkyl or —C$_{1-3}$alkyl optionally substituted with —OCH$_3$ or 1 to 3 of —F, provided that only one of $R^2$ or $R^3$a can be =O,
$R^{3b}$ is —H or —C$_{1-3}$alkyl, or $R^{3b}$ is absent when $R^{3a}$ is =O or when the dashed bond is a double bond or an aromatic bond;
$R^4$ is —H or =O;

R$^5$ is (a) —H, (b) halo, (c) —C$_{1-3}$alkyl optionally substituted with —O—C$_{1-3}$alkyl, (d) —C$_{3-6}$cycloalkyl or (e) heterocycle optionally substituted with —C$_{1-3}$alkyl or halo;

R$^6$ is —H or —C$_{1-3}$alkyl;

R$^{7a}$ is —H or —C$_{1-3}$alkyl optionally substituted with —OH, —OCH$_3$ or 1 to 3 of —F;

R$^{7b}$ is —H or —C$_{1-3}$alkyl;

R$^8$ is —H, halo or —C$_{1-3}$alkyl;

R$^9$ is —H, —F, —OH, —OC$_{1-3}$alkyl, —CH$_2$OH, —NH—R$^{13}$ or

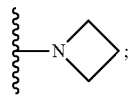

R$^{10}$ is —H, halo, —CN, —C$_{3-4}$cycloalkyl, or —C$_{1-3}$alkyl optionally substituted with 1 to 3 of —F;

or R$^9$ is —O— and is joined together with R$^{10}$ to represent —CH$_2$—CH$_2$—O—;

R$^{11}$ is —H, —CH$_2$OH, —CH$_2$OCH$_3$, or—C$_{1-3}$alkyl optionally substituted with 1 to 3 of —F;

R$^{12}$ is —H, —CH$_2$OH, —CH$_2$OCH$_3$, or—C$_{1-3}$alkyl optionally substituted with 1 to 3 of —F;

or R$^{11}$ and R$^{12}$ are joined together to represent —CH$_2$—CH$_2$—, —CH$_2$—N(CH$_3$)—CH$_2$— or —CH$_2$OCH$_2$—;

R$^{13}$ is —H, —(CH$_2$)$_{0-2}$—C$_{3-6}$cycloalkyl, —(CH$_2$)$_{1-2}$—OC$_{3-6}$cycloalkyl, —(CH$_2$)$_{1-2}$—OC$_{1-3}$alkyl, —(CH$_2$)$_{1-2}$—CN, —C(O)OC$^{1-3}$alkyl, —SO$_2$CH$_3$ or —C$_{1-3}$alkyl optionally substituted with one to three of —F; and the dashed bond ("- - -") represents a single, double or aromatic bond, provided that
  (A) when n is 2, then the dashed bond is a single bond and m is 1; and
  (B) when n is 1 and
    (i) m is 1, or
    (ii) R$^{3a}$ is =O and m is zero,
  then the dashed bond is a single bond; and
  (C) when n is 1, m is zero, R$^2$ is not =O and R$^{3a}$ is not =O, then the dashed bond is a double bond to a patient in need thereof.

11. The method of claim 1 wherein the disorder is selected from hypertension or heart failure.

12. A method for causing diueresis, natriuresis or both, in a patient in need thereof by administering to the patient a therapeutically effective amount of a compound having structural Formula I

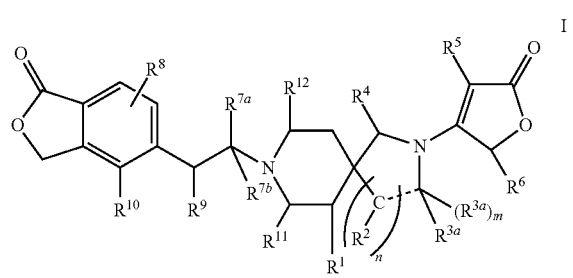

or a pharmaceutically acceptable salt thereof wherein:

R$^1$ is —H, halo, —OH, or —OC$_{1-3}$alkyl;

m is an integer selected from zero (R$^3$b is absent) and 1 (R$^3$b is present);

n is an integer selected from 1 or 2;

R$^2$ is independently selected at each occurrence from —H, =O (oxo), —OH, —C$_{1-3}$alkyl or —OC$_{1-3}$alkyl, provided that when n is 2, then at least one R$^2$ is —H;

R$^{3a}$ is —H, =O, —C$_{3-4}$ cycloalkyl or —C$_{1-3}$alkyl optionally substituted with —OCH$_3$ or 1 to 3 of —F, provided that only one of R$^2$ or R$^{3a}$ can be =O, R$^{3b}$ is —H or —C$_{1-3}$alkyl, or R$^{3b}$ is absent when R$^{3a}$ is =O or when the dashed bond is a double bond or an aromatic bond;

R$^4$ is —H or =O;

R$^5$ is (a) —H, (b) halo, (c) —C$_{1-3}$alkyl optionally substituted with —O—C$_{1-3}$alkyl, (d) —C$_{3-6}$cycloalkyl or (e) heterocycle optionally substituted with —C$_{1-3}$alkyl or halo;

R$^6$ is —H or —C$_{1-3}$alkyl;

R$^{7a}$ is —H or —C$_{1-3}$alkyl optionally substituted with —OH, —OCH$_3$ or 1 to 3 of —F;

R$^{7b}$ is —H or —C$_{1-3}$alkyl;

R$^8$ is —H, halo or —C$_{1-3}$alkyl;

R$^9$ is —H, —F, —OH, —OC$_{1-3}$alkyl, —CH$_2$OH, —NH—R$^{13}$ or

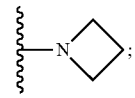

R$^{10}$ is —H, halo, —CN, —C$_{3-4}$cycloalkyl, or —C$_{1-3}$alkyl optionally substituted with 1 to 3 of —F;

or R$^9$ is —O— and is joined together with R$^{10}$ to represent —CH$_2$—CH$_2$—O—;

R$^{11}$ is —H, —CH$_{2OH,}$ —CH$_{2OCH3}$, or —C$_{1-3}$alkyl optionally substituted with 1 to 3 of —F;

R$^{12}$ is —H, —CH$_{2OH,}$ —CH$_{2OCH3}$, or —C$_{1-3}$alkyl optionally substituted with 1 to 3 of —F;

or R$^{11}$ and R$^{12}$ are joined together to represent —CH$_2$-CH$_2$—, —CH$_2$—N(CH$_3$)—CH$_2$— or —CH$_2$OCH$_2$—;

R$^{13}$ is —H, —(CH$_2$)$_{0-2}$—C$_{3-6}$cycloalkyl, —(CH$_2$)$_{1-2}$—O C$_{3-6}$cycloalkyl, —(CH$_2$)$_{1-2}$—OC$_{1-3}$alkyl, —(CH$_2$)$_{1-2}$—CN, —C(O)OC$_{1-3}$alkyl, —SO$_2$CH$_3$ or —C$_{1-3}$alkyl optionally substituted with one to three of —F; and the dashed bond ("- - -") represents a single, double or aromatic bond, provided that
  (A) when n is 2, then the dashed bond is a single bond and m is 1; and
  (B) when n is 1 and
    (i) m is 1, or
    (ii) R$^{3a}$ is =O and m is zero,
  then the dashed bond is a single bond; and
  (C) when n is 1, m is zero, R$^2$ is not =O and R$^{3a}$ is not =O, then the dashed bond is a double bond.

* * * * *